United States Patent
Margolin et al.

(10) Patent No.: US 6,541,606 B2
(45) Date of Patent: *Apr. 1, 2003

(54) STABILIZED PROTEIN CRYSTALS FORMULATIONS CONTAINING THEM AND METHODS OF MAKING THEM

(75) Inventors: Alexey L. Margolin, Newton, MA (US); Nazar K. Khalaf, Worcester, MA (US); Nancy L. St. Clair, Ann Arbor, MI (US); Scott L. Rakestraw, Newark, DE (US); Bhami C. Shenoy, Woburn, MA (US)

(73) Assignee: Altus Biologics Inc., Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/374,132

(22) Filed: Aug. 10, 1999

(65) Prior Publication Data

US 2002/0045582 A1 Apr. 18, 2002

Related U.S. Application Data

(63) Continuation of application No. PCT/US99/09099, filed on Apr. 27, 1999, which is a continuation-in-part of application No. 09/224,475, filed on Dec. 31, 1998, now abandoned.
(60) Provisional application No. 60/083,148, filed on Apr. 27, 1998, and provisional application No. 60/070,274, filed on Dec. 31, 1997.

(51) Int. Cl.$^7$ .................. C07K 17/00; C12N 11/00; C12N 9/00; A61K 38/43; A61K 9/50

(52) U.S. Cl. .................. 530/350; 530/402; 530/403; 530/813; 530/815; 424/501; 424/489; 424/94.1; 424/94.2; 424/94.5; 424/94.6; 435/39; 435/174; 435/178; 435/181; 435/183; 435/188; 514/2; 514/4

(58) Field of Search ................. 424/501, 489, 424/94.1, 94.2, 94.5, 94.6; 530/350, 402, 403, 813, 815; 435/39, 174, 178, 181, 183, 188; 514/2, 4

(56) References Cited

U.S. PATENT DOCUMENTS

| | | | |
|---|---|---|---|
| 4,606,909 A | 8/1986 | Bechgaard et al. ............ 424/21 |
| 5,120,650 A | 6/1992 | Visuri ........................ 435/176 |
| 5,270,194 A | 12/1993 | D'Alterio et al. ........... 435/188 |
| 5,385,959 A | 1/1995 | Tsaur et al. .................. 523/201 |
| 5,500,223 A | 3/1996 | Behan et al. ................ 424/451 |
| 5,593,697 A | 1/1997 | Barr et al. .................. 424/490 |
| 5,601,846 A * | 2/1997 | Milstein et al. ............ 424/499 |
| 5,603,956 A | 2/1997 | Mateescu et al. ........... 424/488 |
| 5,618,710 A * | 4/1997 | Navia et al. ................ 435/174 |
| 5,734,026 A * | 3/1998 | Florin-Robertsson et al. .......................... 530/399 |
| 5,811,406 A | 9/1998 | Szoka, Jr. et al. ............. 514/44 |
| 5,827,531 A * | 10/1998 | Morrison et al. ............ 424/450 |
| 5,898,028 A * | 4/1999 | Jensen et al. .................... 514/4 |
| 5,932,212 A * | 8/1999 | Khalaf ....................... 424/94.6 |
| 6,004,549 A | 12/1999 | Reichert et al. ............ 424/85.4 |
| 6,004,768 A | 12/1999 | Navia et al. .................. 435/18 |
| 6,140,475 A | 10/2000 | Margolin et al. ............ 530/402 |

FOREIGN PATENT DOCUMENTS

| | | |
|---|---|---|
| CA | 1196864 | 11/1985 |
| WO | WO 96/18417 | 6/1996 |
| WO | WO 96/41873 | 12/1996 |
| WO | WO 98/42749 | * 10/1998 |
| WO | WO 98/46732 | 10/1998 |

OTHER PUBLICATIONS

Margolin, IBTECH, vol. 14, pp. 223–230, Jul. 1996.*

Vilenchik et al., *J. Am. Chem. Soc.*, vol. 120, pp. 4290–4294, 1998.*

McPherson et al., *Methods of Biochemical Analysis*, vol. 23, pp. 249–345, 1976.*

(List continued on next page.)

*Primary Examiner*—Christopher S. F. Low
*Assistant Examiner*—Abdel A. Mohamed
(74) *Attorney, Agent, or Firm*—Fish & Neave; James F. Haley, Jr.; Margaret A. Pierri

(57) ABSTRACT

This invention relates to methods for the stabilization, storage and delivery of biologically active macromolecules, such as proteins, peptides and nucleic acids. In particular, this invention relates to protein or nucleic acid crystals, formulations and compositions comprising them. Methods are provided for the crystallization of proteins and nucleic acids and for the preparation of stabilized protein or nucleic acid crystals for use in dry or slurry formulations. The present invention is further directed to encapsulating proteins, glycoproteins, enzymes, antibodies, hormones and peptide crystals or crystal formulations into compositions for biological delivery to humans and animals. According to this invention, protein crystals or crystal formulations are encapsulated within a matrix comprising a polymeric carrier to form a composition. The formulations and compositions enhance preservation of the native biologically active tertiary structure of the proteins and create a reservoir which can slowly release active protein where and when it is needed. Methods are provided preparing stabilized formulations using pharmaceutical ingredients or excipients and optionally encapsulating them in a polymeric carrier to produce compositions and using such protein crystal formulations and compositions for biomedical applications, including delivery of therapeutic proteins and vaccines. Additional uses for the protein crystal formulations and compositions of this invention involve protein delivery in human food, agricultural feeds, veterinary compositions, diagnostics, cosmetics and personal care compositions.

22 Claims, 24 Drawing Sheets

OTHER PUBLICATIONS

Lalonde et al., *J. Am. Chem. Soc.*, vol. 117, pp. 6845–6852, 1995.*

D.C. Chan et al., "Core structure of gp41 from the HIV envelope glycoprotein." *Cell*, 89, 263–273 (1997).

D. Fass et al., "Structure of a murine leukemia virus receptor-binding glycoprotein at 2.0 angstrom resolution." *Science*, 277, 1662–1666 (1997).

M. Gajhede et al., "Crystal structure of horseradish peroxidase C at 2.15 Å resolution." *Nature Structural Biology*, 4, 1032–1038 (1997).

G.F. Gao et al., "Crystal structure of the complex between human CD8αα and HLA–A2." *Nature*, 387, 630–634 (1997).

F.J. Hoedemaeker et al., "A single chain Fv fragment of P–glycoprotein–specific monoclonal antibody C219: design, expression, and crystal structure at 2.4 Å resolution." *J. Biol. Chem.*, 272, 29784–29789.

N. Kamiya et al., "Surfactant–coated lipase suitable for the enzymatic resolution of menthol as a biocatalyst in organic media." *Biotechnol. Prog.*, 11, 270–275 (1995).

A.L. Margolin, "Novel crystalline catalysts." TIBTECH, 14, 223–230 (1996).

B.H. Shilton et al., "Crystallization of a soluble form of the Kex1p serine carboxypeptidase from *Saccharomyces cerevisiae*." *Protein Science*, 5, 395–397 (1996).

X. Wang et al., "The crystal structure of bovine bile salt activated lipase: insights into the bile salt activation mechanism." *Structure*, 5, 1209–1218 (1997).

* cited by examiner

STABILIZED PROTEIN CRYSTALS FORMULATIONS CONTAINING THEM AND METHODS OF MAKING THEM

CROSS-REFERENCE TO RELATED APPLICATIONS

This application is a continuation of co-pending International Application PCT/US99/09099, filed Apr. 27, 1999, which claims benefit under 35 U.S.C. § 119(e) of U.S. provisional application No. 60/083,148 filed on Apr. 27, 1998. This application is also a continuation-in-part of U.S. application 09/224,475, filed on Dec. 31, 1998, which now abandoned, which claims benefit under 35 U.S.C. § 119(e) of U.S. provisional application No. 60/070,274, filed on Dec. 31, 1997.

TECHNICAL FIELD OF THE INVENTION

This invention relates to methods for the stabilization, storage and delivery of biologically active macromolecules, such as proteins, peptides and nucleic acids. In particular, this invention relates to protein or nucleic acid crystals, formulations and compositions comprising them. Methods are provided for the crystallization of proteins and nucleic acids and for the preparation of stabilized protein or nucleic acid crystals for use in dry or slurry formulations. The crystals, crystal formulations and compositions of this invention can be reconstituted with a diluent for the parenteral administration of biologically active macromolecular components.

The methods of this invention are useful for preparing crystals of "naked" DNA and RNA sequences that code for therapeutic or immunogenic proteins and can be administered parenterally. The dissolving DNA and RNA molecules, subsequently taken up by the cells and used to express the protein with the proper glycosylation pattern, can be either therapeutic or immunogenic. Alternatively, the present invention is useful for preparing crystals, crystal formulations and compositions of sense and antisense polynucleotides of RNA or DNA.

The present invention is further directed to encapsulating proteins, glycoproteins, enzymes, antibodies, hormones and peptide crystals or crystal formulations into compositions for biological delivery to humans and animals. According to this invention, protein crystals or crystal formulations are encapsulated within a matrix comprising a polymeric carrier to form a composition. The formulations and compositions enhance preservation of the native biologically active tertiary structure of the proteins and create a reservoir which can slowly release active protein where and when it is needed. Such polymeric carriers include biocompatible and biodegradable polymers. The biologically active protein is subsequently released in a controlled manner over a period of time, as determined by the particular encapsulation technique, polymer formulation, crystal geometry, crystal solubility, crystal crosslinking and formulation conditions used. Methods are provided for crystallizing proteins, preparing stabilized formulations using pharmaceutical ingredients or excipients and optionally encapsulating them in a polymeric carrier to produce compositions and using such protein crystal formulations and compositions for biomedical applications, including delivery of therapeutic proteins and vaccines. Additional uses for the protein crystal formulations and compositions of this invention involve protein delivery in human food, agricultural feeds, veterinary compositions, diagnostics, cosmetics and personal care compositions.

BACKGROUND OF THE INVENTION

Proteins are used in a wide range of applications in the fields of pharmaceuticals, veterinary products, cosmetics and other consumer products, foods, feeds, diagnostics, industrial chemistry and decontamination. At times, such uses have been limited by constraints inherent in proteins themselves or imposed by the environment or media in which they are used. Such constraints may result in poor stability of the proteins, variability of performance or high cost.

It is imperative that the higher order three-dimensional architecture or tertiary structure of a protein be preserved until such time that the individual protein molecules are required to perform their unique function. To date, a limiting factor for use of proteins, particularly in therapeutic regimens, remains the sensitivity of protein structure to chemical and physical denaturation encountered during delivery.

Various approaches have been employed to overcome these barriers. However, these approaches often incur either loss of protein activity or the additional expense of protein stabilizing carriers or formulations.

One approach to overcoming barriers to the widespread use of proteins is crosslinked enzyme crystal ("CLEC™") technology [N. L. St. Clair and M. A. Navia, *J. Am. Chem. Soc.*, 114, pp. 4314–16 (1992)]. See also PCT patent application PCT/US91/05415. Crosslinked enzyme crystals retain their activity in environments that are normally incompatible with enzyme function. Such environments include prolonged exposure to proteases, organic solvents, high temperature or extremes of pH. In such environments, crosslinked enzyme crystals remain insoluble, stable and active.

Despite recent progress in protein technology generally, two problems which are discussed below continue to limit the use of biological macromolecules in industry and medicine. The first problem relates to molecular stability and sensitivity of higher order tertiary structures to chemical and physical denaturation during manufacturing and storage. Second, the field of biological delivery of therapeutic proteins requires that vehicles be provided which release native proteins, such as proteins, glycoproteins, enzymes, antibodies, hormones, nucleic acids and peptides at a rate that is consistent with the needs of the particular patient or the disease process.

Macromolecule Stability

Numerous factors differentiate biological macromolecules from conventional chemical entities, such as for example, their size, conformation and amphiphilic nature. Macromolecules are not only susceptible to chemical, but also physical degradation. They are sensitive to a variety of environmental factors, such as temperature, oxidizing agents, pH, freezing, shaking and shear stress [Cholewinski, M., Luckel, B. and Horn, H., *Acta Helv.*, 71, 405 (1996)]. In considering a macromolecule for drug development, stability factors must be considered when choosing a production process.

Maintenance of biological activity during the development and manufacture of pharmaceutical products depends on the inherent stability of the macromolecule, as well as the stabilization techniques employed. A range of protein stabilization techniques exist; including:

a) Addition of chemical "stabilizers" to the aqueous solution or suspension of protein. For example, U.S. Pat. Nos. 4,297,344 discloses stabilization of coagulation factors II and VIII, antithrombin III and plasminogen against heat by adding selected amino acids. U.S. Pat. No. 4,783,441 discloses a method for stabilizing proteins by adding surface-active substances. U.S. Pat. No. 4,812,557 discloses a method for stabilizing interleukin-2 using human serum albumin. The drawback of such methods is that each formulation is specific to the protein of interest and requires significant development efforts.

b) Freeze/thaw methods in which the preparation is mixed with a cryoprotectant and stored at very low temperatures. However, not all proteins will survive a freeze/thaw cycle.

c) Cold storage with cryoprotectant additive, normally glycerol.

d) Storage in the glass form, as described in U.S. Pat. No. 5,098,893. In this case, proteins are dissolved in water-soluble or water-swellable substances which are in amorphous or glassy state.

e) The most widely used method for the stabilization of proteins is freeze-drying or lyophilization [Carpenter, J. F., Pical, M. J., Chang, B. S. and Randolph, T. W., *Pharm. Res.*, 14:(8) 969 (1997)]. Whenever sufficient protein stability cannot be achieved in aqueous solution, lyophilization provides the most viable alternative. One disadvantage of lyophilization is that it requires sophisticated processing, is time consuming and expensive [Carpenter, J. F., Pical, M. J., Chang, B. S. and Randolph, T. W., *Pharm. Res.*, 14:(8) 969 (1997) and literature cited therein]. In addition, if lyophilization is not carried out carefully, most preparations are at least partially denatured by the freezing and dehydration steps of the technique. The result is frequently irreversible aggregation of a portion of protein molecules, rendering a formulation unacceptable for parenteral administration.

The vast majority of protein formulations produced by the above-described techniques require cold storage, sometimes as low as −20° C. Exposure to elevated temperatures during shipping or storage can result in significant activity losses. Thus, storage at elevated, or even ambient temperatures, is not possible for many proteins.

Proteins, peptides and nucleic acids are increasingly employed in the pharmaceutical, diagnostic, food, cosmetic, detergent and research industries. There is a great need for alternative stabilization procedures, which are fast, inexpensive and applicable to a broad range of biological macromolecules. In particular, stabilization procedures are needed that do not rely on the excessive use of excipients, which can interfere with the functions of those biological macromolecules.

The stability of small molecule crystalline drugs is such that they can withstand extreme forces during the formulation process (see U.S. Pat. No. 5,510,118). Forces associated with milling nanoparticles of crystalline material of relatively insoluble drugs include: shear stress, turbulent flow, high impact collisions, cavitation and grinding. Small molecular crystalline compounds have been recognized as being much more stable toward chemical degradation than the corresponding amorphous solid [Pical, M. J., Lukes, A. L., Lang, J. E. and Gaines, *J. Pharm. Sci.*, 67, 767 (1978)]. Unfortunately, crystals of macromolecules, such as proteins and nucleic acids, present additional problems and difficulties not associated with small molecules.

For most of this century, science and medicine have tried to solve the problem of providing insulin in a useful form to diabetics. Attempts have been made to solve some of the problems of stability and biological delivery of that protein. For example, U.S. Pat. No. 5,506,203 describes the use of amorphous insulin combined with an absorbtion enhancer. The solid state insulin was exclusively amorphous material, as shown by a polarized light microscope.

Jensen et al. co-precipitated insulin with an absorbtion enhancer for use in respiratory tract delivery of insulin (See PCT patent application Wo 98/42368). Here, the absorbtion enhancer was desribed as a surfactant, such as a salt of a fatty acid or a bile salt. Insulin crystals of less than 10 micrometers in diameter and lacking zinc were produced by S. Havelund (See PCT patent application Wo 98/42749). Similarly, crystals were also produced in the presence of surfactants to enhance pulmonary administration.

To date, those of skill in the art recognize that the greatly enhanced stability of the crystalline state observed for small molecules does not translate to biological macromolecules [Pical, M. J. and Rigsbee, D. R., *Pharm. Res.*, 14:1379 (1997)]. For example, aqueous suspensions of crystalline insulin are only slightly more stable (to the degree of a factor of two) than corresponding suspensions of amorphous phase [Brange, J., Langkjaer, L., Havelund, S. and Volund, A., *Pharm. Res.*, 9:715 (1992)]. In the solid state, lyophilized amorphous insulin is far more stable than lyophilized crystalline insulin under all conditions investigated [Pical, M. J. and Rigsbee, D. R., *Pharm. Res.*, 14:1379 (1997)].

Until now, formulations of crystalline proteins have been available only for very small proteins, e.g. proteins with molecular weights of less than 10,000 Daltons. Molecular weight has profound effect on all properties of macromolecules, including their macromolecular volume, hydration, viscosity, diffusion, mobility and stability. [Cantor, C. R and Schimmel, P. R, Biophysical Chemistry, W. H. Freeman and Co., New York, 1980].

SUMMARY OF THE INVENTION

We have found, surprisingly, that biological macromolecules which are not stable when held in solution at ambient or elevated temperatures can nevertheless be successfully stored in dry form for long periods of time at such temperatures in crystalline form. As a practical matter, five aspects of this discovery are particularly advantageous.

First, crystallinity of stored materials is very important, since large scale crystallization can be introduced as a final purification step and/or concentration step in clinical manufacturing processes, such as those for manufacturing therapeutics and vaccines. Moreover, large scale crystallization can replace some of the purification steps in the manufacturing process. For example, protein crystallization can streamline the production of protein formulations making it more affordable.

Second, macromolecular interactions which occur in solution are prevented or severely reduced in the crystalline state, due to considerable reduction of all reaction rates. Thus, the crystalline state is uniquely suited to the storage of mixtures of biological macromolecules.

Third, solid crystalline preparations can be easily reconstituted to generate ready to use parenteral formulations having very high protein concentration. Such protein concentrations are considered to be particularly useful where the formulation is intended for subcutaneous administration. (See PCT patent application Wo 97/04801). For subcutaneous administration, injection volumes of 1.5 ml or less are well tolerated. Thus, for proteins that are dosed at 1 mg/kg on a weekly basis a protein concentration of at least 50 mg/ml is required and 100–200 mg/ml is preferred. These concentrations are difficult to achieve in liquid formulations, due to the aggregation problems. They can easily be achieved in the crystalline formulations of this invention.

Fourth, protein crystals also constitute a particularly advantageous form for pharmaceutical dosage preparation. The crystals may be used as a basis for slow release formulations in vivo. As those of skill in the art will appreciate, particle size is of importance for the dissolution of crystals and release of activity. It is also known that the rate of release is more predictable if the crystals have substantially uniform particle size and do not contain amorphous precipitate (see European patent 0 265 214). Thus, protein crystals may be advantageously used (see PCT patent application WO 96/40049), on implantable devices. Implant reservoirs are generally on the order of 25–250 μl. With this volume restriction, a formulation of high concentration (greater than 10%) and a minimum amount of suspension vehicle is preferred. Protein crystals of this invention may be easily formulated in non-aqueous suspensions in such high concentrations.

Fifth, another advantage of crystals is that certain variables can be manipulated to modulate the release of macromolecules over time. For example, crystal size, shape, formulation with excipients that effect dissolution, crosslinking, level of crosslinking and encapsulation into a polymer matrix can all be manipulated to produce delivery vehicles for biological molecules.

The present invention overcomes the above-described obstacles by employing the most stable form of an active protein, the crystalline form and either (1) adding ingredients or excipients where necessary to stabilize dried crystals or (2) encapsulating the protein crystals or crystal formulations within a polymeric carrier to produce a composition that contains each crystal and subsequently allows the release of active protein molecules. Any form of protein, including glycoproteins, antibodies, enzymes, hormones or peptides, may be crystallized and stabilized or encapsulated into compositions according to the methods of this invention. In addition, the nucleic acids coding for such proteins may be similarly treated.

The crystal(s) may be encapsulated using a variety of polymeric carriers having unique properties suitable for delivery to different and specific environments or for effecting specific functions. The rate of dissolution of the compositions and, therefore, delivery of the active protein can be modulated by varying crystal size, polymer composition, polymer crosslinking, crystal crosslinking, polymer thickness, polymer hydrophobicity, polymer crystallinity or polymer solubility.

The addition of ingredients or excipients to the crystals of the present invention or the encapsulation of protein crystals or crystal formulations results in further stabilization of the protein constituent.

DETAILED DESCRIPTION OF THE INVENTION

Figure 1:
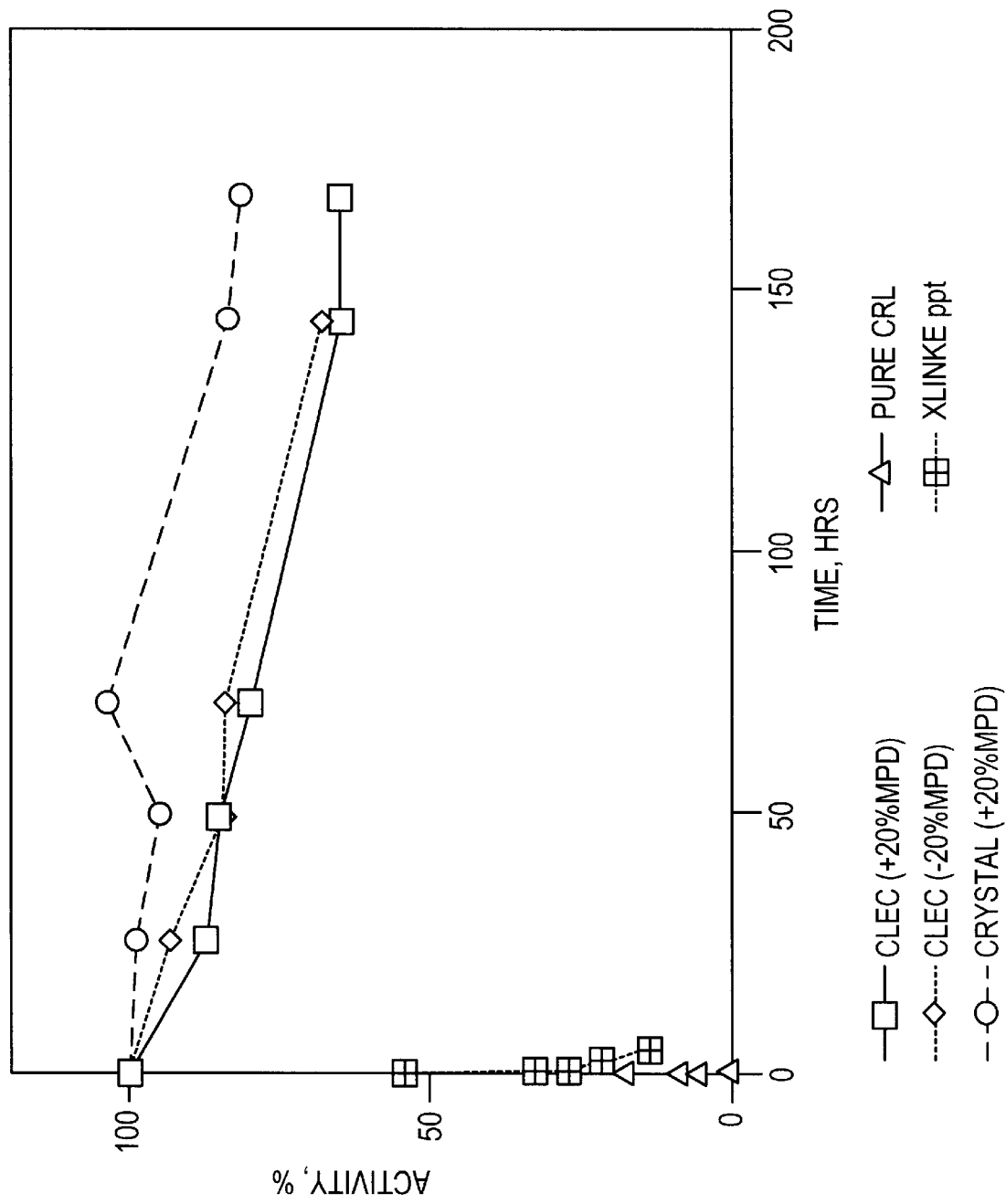
FIG. 1 depicts the relative stability of the following molecular states of *Candida rugosa* lipase: crosslinked amorphous, liquid, crystalline in 20% organic solvent, crosslinked crystalline in 20% organic solvent, crosslinked crystalline without organic solvent ("Xlinke ppt" denotes crosslinked precipitate).

In order that the invention herein described may be more fully understood, the following detailed description is set forth. In the description, the following terms are employed:

Amorphous solid—a non-crystalline solid form of protein, sometimes referred to as amorphous precipitate, which has no molecular lattice structure characteristic of the crystalline solid state.

Anti-sense polynucleotides—RNA or DNA which codes for RNA, which is complementary to the mRNA of a gene whose expression is intended to be inhibited.

Aqueous-organic solvent mixture—a mixture comprising n% organic solvent, where n is between 1 and 99 and m% aqueous, where m is 100-n.

Biocompatible polymers—polymers that are non-antigenic (when not used as an adjuvant), non-carcinogenic, non-toxic and which are not otherwise inherently incompatible with living organisms. Examples include: poly (acrylic acid), poly (cyanoacrylates), poly (amino acids), poly (anhydrides), poly (depsipeptide), poly (esters) such as poly (lactic acid) or PLA, poly (lactic-co-glycolic acid) or PLGA, poly (β-hydroxybutryate), poly (caprolactone) and poly (dioxanone); poly (ethylene glycol), poly ((hydroxypropyl) methacrylamide, poly [(organo)phosphazene], poly (ortho esters), poly (vinyl alcohol), poly (vinylpyrrolidone), maleic anhydride-alkyl vinyl ether copolymers, pluronic polyols, albumin, alginate, cellulose and cellulose derivatives, collagen, fibrin, gelatin, hyaluronic acid, oligosaccarides, glycaminoglycans, sulfated polysaccarides, blends and copolymers thereof.

Biodearadable Polymers—polymers that degrade by hydrolysis or solubilization. Degradation can be heterogenous—occurring primarily at the particle surface, or homogenous—degrading evenly throughout the polymer matrix, or a combination of such processes.

Biological macromolecule—biological polymers such as proteins, deoxyribonucleic acids (DNA) and ribonucleic acids (RNA). For the purposes of this application, biological macromolecules are also referred to as macromolecules.

Change in chemical composition—any change in the chemical components of the environment surrounding a protein or nucleic acid crystal or crystal formulation that affects the stability or rate of dissolution of the crystal component.

Change in shear force—any change in factors of the environment surrounding a protein or nucleic acid crystal or crystal formulation under conditions of use, such as, changes in mechanical pressure, both positive and negative, revolution stirring, centrifugation, tumbling, mechanical agitation and filtration pumping.

Composition—either uncrosslinked protein crystals, crosslinked protein crystals, nucleic acid crystals or formulations containing them, which have been encapsulated within a polymeric carrier to form coated particles. As used herein, composition always refers to encapsulated crystals or formulations.

Controlled dissolution—dissolution of a protein or nucleic acid crystal or crystal formulation or release of the crystalline constituent of said formulation that is controlled by a factor selected from the group consisting of the following: the surface area of said crystal; the size of said crystal; the shape of said crystal, the concentration of excipient component; the number and nature of excipient components; the molecular weight of the excipient components and combinations thereof.

Co-polymer—a polymer made with more than one monomer species.

Crystal—one form of the solid state of matter, which is distinct from a second form—the amorphous solid state. Crystals display characteristic features including a lattice structure, characteristic shapes and optical properties such as refractive index. A crystal consists of atoms arranged in a pattern that repeats periodically in three dimensions (C. S. Barrett, Structure of Metals, 2nd ed., McGraw-Hill, New York, 1952, p.1). The crystals of the present invention may be protein, glycoprotein, peptide, antibodies, therapeutic proteins, or DNA or RNA coding for such proteins.

Drying of Protein or Nucleic Acid Crystals—removal of water, organic solvent or liquid polymer by means including drying with $N_2$, air or inert gases, vacuum oven drying, lyophilization, washing with a volatile organic solvent followed by evaporation of the solvent, or evaporation in a fume hood. Typically, drying is achieved when the crystals become a free flowing powder. Drying may be carried out by passing a stream of gas over wet crystals. The gas may be selected from the group consisting of: nitrogen, argon, helium, carbon dioxide, air or combinations thereof.

Effective amount—an amount of a protein or nucleic acid crystal or crystal formulation or composition of this invention which is effective to treat, immunize, boost, protect, repair or detoxify the subject or area to which it is administered over some period of time.

Emulsifier—a surface active agent which reduces interfacial tension between polymer coated protein crystals and a solution.

Formulations or (Protein or nucleic acid crystal formulations)—a combination of the protein or nucleic acid crystals of this invention and one or more ingredients or excipients, including sugars and biocompatible polymers. Examples of excipients are described in the *Handbook of Pharmaceutical Excipients*, published jointly by the American Pharmaceutical Association and the Pharmaceutical Society of Great Britian. For the purposes of this application, "formulations" include "crystal formulations". Furthermore, "formulations" include "protein or nucleic acid crystal formulations".

Formulations for decontamination—formulations selected from the group consisting of: formulations for decontamination of chemical wastes, herbicides, insecticides, pesticides and environmental hazards.

Gene therapy—therapy using formulations and/or compositions of DNA coding for a protein which is defective, missing, or insufficiently expressed in an individual. The crystals are injected into non-proliferating tissue where the DNA is taken up into the cells and expressed for a period of one to six months. The expressed protein serves to temporarily replace or supplement the endogenous protein. Gene therapy can also serve to inhibit gene expression by providing transgenes with the gene orientation reversed relative to the promoter so that antisense mRNA is produced in vivo.

Glycoprotein—a protein or peptide covalently linked to a carbohydrate. The carbohydrate may be monomeric or composed of oligosaccharides.

Homo-polymer—a polymer made with a single monomer species.

Immunotherapeutic—a protein derived from a tumor cell, virus or bacteria having a protein activity of inducing protective immunity to said tumor cell, virus, or bacteria. An immunotherapeutic may be administered directly—as a protein or indirectly—by injecting DNA or RNA which codes for the protein.

Immunotherapeutics may also be protein or glycoprotein cytokines or immune cell co-stimulatory molecules which stimulate the immune system to reduce or eliminate said tumor cell, virus or bacteria.

Liquid Polymer—pure liquid phase synthetic polymers, such as poly-ethylene glycol (PEG), in the absence of aqueous or organic solvents.

Macromolecules—proteins, glycoproteins, peptides, therapeutic proteins, DNA or RNA molecules.

Method of Administration—protein or nucleic acid crystals or crystal formulations or compositions may be appropriate for a variety of modes of administration. These may include oral, parenteral, subcutaneous, intravenous, pulmonary, intralesional, or topical administration. Alternatively, nucleic acid crystals may be covalently attached to gold particles, or other carrier beads, for delivery to non-proliferating tissues such as muscles with a "DNA gun".

Naked DNA—a nonreplicating, nonintegrating polynucleotide which codes for a vaccine antigen, therapeutic protein, or immunotherapeutic protein, which may be operatively linked to a promoter and inserted into a replication competent plasmid. The DNA is free from association with transfection facilitating proteins, viral particles, liposomal formulations, lipids and calcium phosphate precipitating agents.

Naked DNA vaccine—crystals of DNA coding for a vaccine antigen or a vaccine antigen and an immunotherapeutic. The vaccine is injected into non-proliferating tissue where the DNA is taken up into the cells and expressed for a period of one to six months. The nucleic acid crystals may be covalently linked to gold particles to aid in delivery to the site of administration.

Organic solvents—any solvent of non-aqueous origin, including liquid polymers and mixtures thereof. Organic solvents suitable for the present invention include: acetone, methyl alcohol, methyl isobutyl ketone, chloroform, 1-propanol, isopropanol, 2-propanol, acetonitrile, 1-butanol, 2-butanol, ethyl alcohol, cyclohexane, dioxane, ethyl acetate, dimethylformamide, dichloroethane, hexane, isooctane, methylene chloride, tert-butyl alchohol, toluene, carbon tetrachloride, or combinations thereof Peptide—a polypeptide of small to intermediate molecular weight, usually 3 to 35 amino acid residues and frequently but not necessarily representing a fragment of a larger protein.

Pharmaceutically effective amount—an amount of a protein or nucleic acid crystal or crystal formulation or composition which is effective to treat a condition in an living organism to whom it is administered over some period of time.

Ingredients—any excipient or excipients, including pharmaceutical ingredients or excipients. Excipients include, for example, the following:

Acidifying Agents
  acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid Aerosol Propellants
  butane, dichlorodifluoromethane, dichlorotetrafluoroethane, isobutane, propane, trichloromonofluoromethane Air Displacements
  carbon dioxide, nitrogen Alcohol Denaturants
  denatonium benzoate, methyl isobutyl ketone, sucrose octacetate Alkalizing Agents
  strong ammonia solution, ammonium carbonate, diethanolamine, diisopropanolamine, potassium hydroxide, sodium bicarbonate, sodium borate, sodium carbonate, sodium hydroxide, trolamine Anticaking Agents (See Glidant)

Antifoaming Agents
  dimethicone, simethicone

Antimicrobial Preservatives
  benzalkonium chloride, benzalkonium chloride solution, benzelthonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol Antioxidants
  ascorbic acid, acorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sufur dioxide, tocopherol, tocopherols excipient Buffering Agents
  acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate Capsule Lubricants (See Tablet and Capsule Lubricant)

Chelating Agents
  edetate disodium, ethylenediaminetetraacetic acid and salts, edetic acid Coating Agents
  sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyethylene glycol, polyvinyl acetate phthalate, shellac, sucrose, titanium dioxide, carnauba wax, microcystalline wax, zein Colors
  caramel, red, yellow, black or blends, ferric oxide Complexing Agents
  ethylenediaminetetraacetic acid and salts (EDTA), edetic acid, gentisic acid ethanolmaide, oxyquinoline sulfate Desiccants
  calcium chloride, calcium sulfate, silicon dioxide Emulsifying and/or Solubilizing Agents
  acacia, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 caster oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, soritan monooleate, sorbitan monopalmitate, sorbitan monostearate, stearic acid, trolamine, emulsifying wax Filtering Aids
  powdered cellulose, purified siliceous earth Flavors and Perfumes
  anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin Glidant and/or Anticaking Agents
  calcium silicate, magnesium silicate, colloidal silicon dioxide, talc Humectants
  glycerin, hexylene glycol, propylene glycol, sorbitol Ointment Bases
  lanolin, anhydrous lanolin, hydrophilic ointment, white ointment, yellow ointment, polyethylene glycol ointment, petrolatum, hydrophilic petrolatum, white petrolatum, rose water ointment, squalane Plasticizers
  castor oil, diacetylated monoglycerides, diethyl phthalate, glycerin, mono- and di-acetylated monoglycerides, polyethylene glycol, propylene glycol, triacetin, triethyl citrate
Polymer Membranes
  cellulose acetate
Solvents
  acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, polyethylene glycol, propylene carbonate, propylene glycol, sesame oil, water for injection, sterile water for injection, sterile water for irrigation, purified water
Sorbents
  powdered cellulose, charcoal, purified siliceous earth
Carbon Dioxide Sorbents
  barium hydroxide lime, soda lime
Stiffening Agents
  hydrogenated castor oil, cetostearyl alcohol, cetyl alcohol, cetyl esters wax, hard fat, paraffin, polyethylene excipient, stearyl alcohol, emulsifying wax, white wax, yellow wax
Suppository Bases
  cocoa butter, hard fat, polyethylene glycol
Suspending and/or Viscosity-increasing Agents
  acacia, agar, alginic acid, aluminum monostearate, bentonite, purified bentonite, magma bentonite, carbomer 934p, carboxymethylcellulose calcium, carboxymethylcellulose sodium, carboxymethycellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, xanthan gum
Sweetening Agents
  aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup
Tablet Binders
  acacia, alginic acid, sodium carboxymethylcellulose, microcrystalline cellulose, dextrin, ethylcellulose, gelatin, liquid glucose, guar gum, hydroxypropyl methylcellulose, methycellulose, polyethylene oxide, povidone, pregelatinized starch, syrup
Tablet and/or Capsule Diluents
  calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar
Table Disintegrants
  alginic acid, microcrystalline cellulose, croscarmellose sodium, corspovidone, polacrilin potassium, sodium starch glycolate, starch, pregelatinized starch
Tablet and/or Capsule Lubricants
  calcium stearate, glyceryl behenate, magnesium stearate, light mineral oil, polyethylene glycol, sodium stearyl fumarate, stearic acid, purified stearic acid, talc, hydrogenated vegetable oil, zinc stearate
Tonicity Agent
  dextrose, glycerin, mannitol, potassium chloride, sodium chloride
Vehicle: Flavored and/or Sweetened
  aromatic elixir, compound benzaldehyde elixir, isoalcoholic elixir, peppermint water, sorbitol solution, syrup, tolu balsam syrup
Vehicle: oleaginous
  almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, seame oil, soybean oil, squalane
Vehicle: Solid Carrier
  sugar spheres
Vehicle: Sterile
  Bacteriostatic water for injection, bacteriostatic sodium chloride injection
Viscosity-increasing (see Suspending Agent)
Water Repelling Agent
  cyclomethicone, dimethicone, simethicone
Wetting and/or Solubilizing Agent
  benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaureate, sorbitan monooleate, sorbitan monopalmitate, sorbitan monostearate, tyloxapol Preferred ingredients or excipients include: Salts of 1) amino acids such as glycine, arginine, aspartic acid, glutamic acid, lysine, asparagine, glutamine, proline, 2) carbohydrates, e.g. monosaccharides such as glucose, fructose, galactose, Mannose, arabinose, xylose, ribose and 3) disaccharides, such as lactose, trehalose, maltose, sucrose and 4) polysaccharides, such as maltodextrins, dextrans, starch, glycogen and 5) alditols, such as mannitol, xylitol, lactitol, sorbitol 6) glucuronic acid, galacturonic acid, 7) cyclodextrins, such as methyl cyclodextrin, hydroxypropyl-β-cyclodextrin and alike 8) inorganic salts, such as sodium chloride, potassium chloride, magnesium chloride, phosphates of sodium and potassium, boric acid ammonium carbonate and ammonium phosphate, and 9) organic salts, such as acetates, citrate, ascorbate, lactate 10) emulsifying or solubilizing agents like acacia, diethanolamine, glyceryl monostearate, lecithin, monoethanolamine, oleic acid , oleyl alcohol, poloxamer, polysorbates, sodium lauryl sulfate, stearic acid, sorbitan monolaurate, sorbitan monostearate, and other sorbitan derivatives, polyoxyl derivatives, wax, polyoxyethylene derivatives, sorbitan derivatives 11) viscosity increasing reagents like, agar, alginic acid and its salts, guar gum, pectin, polyvinyl alcohol, polyethylene oxide, cellulose and its derivatives propylene carbonate, polyethylene glycol, hexylene glycol, tyloxapol. A further preferred group of excipients or ingredients includes sucrose, trehalose, lactose, sorbitol, lactitol, inositol, salts of sodium and potssium such as acetate, phosphates, citrates, borate, glycine, arginine, polyethylene oxide, polyvinyl alcohol, polyethylene glycol, hexylene glycol, methoxy polyethylene glycol, gelatin, hydroxypropyl-β-cyclodextrin.

Polymer—a large molecule built up by the repetition of small, simple chemical units. The repeating units may be linear or branched to form interconnected networks. The repeat unit is usually equivalent or nearly equivalent to the monomer.

Polymeric carriers—polymers used for encapsulation of protein crystals for delivery of proteins, including biological delivery. Such polymers include biocompatible and biodegradable polymers. The polymeric carrier may be a single polymer type or it may be composed of a mixture of polymer types. Polymers useful as the polymeric carrier, include for example, poly (acrylic acid), poly (cyanoacrylates), poly (amino acids), poly (anhydrides), poly (depsipeptide), poly (esters) such as poly (lactic acid) or PLA, poly (lactic-co-glycolic acid) or PLGA, poly (B-hydroxybutyrate), poly (caprolactone) and poly (dioxanone); poly (ethylene glycol), poly ((hydroxypropyl)methacrylamide, poly [(organo) phosphazene], poly (ortho esters), poly (vinyl alcohol), poly (vinylpyrrolidone), maleic anhydride-alkyl vinyl ether copolymers, pluronic polyols, albumin, natural and synthetic polypeptides, alginate, cellulose and cellulose derivatives, collagen, fibrin, gelatin, hyaluronic acid, oligosaccharides, glycaminoglycans, sulfated polysaccharides, or any conventional material that will encapsulate protein crystals.

Protein—a complex high polymer containing carbon, hydrogen, oxygen, nitrogen and usually sulfur and composed of chains of amino acids connected by peptide linkages. Proteins in this application refer to glycoproteins, antibodies, non-enzyme proteins, enzymes, hormones and peptides. The molecular weight range for proteins includes peptides of 1000 Daltons to glycoproteins of 600 to 1000 kiloDaltons. Small proteins, less than 10,000 Daltons, may be too small to be characterized by a highly organized tertiary structure, wherein said tertiary structure is organized around a hydrophobic core.

In one embodiment of this invention, such proteins have a molecular weight of greater than or equal to 10,000 Daltons. According to an alternate embodiment, that molecular weight is greater than or equal to 20,000 Daltons. According to another alternate embodiment, that molecular weight is greater than or equal to 30,000 Daltons. According to a further alternate embodiment, that molecular weight is greater than or equal to 40,000 Daltons. According to another alternate embodiment, that molecular weight is greater than or equal to 50,000 Daltons.

Protein activity—an activity selected from the group consisting of binding, catalysis, signaling, transport, or other activities which induce a functional response within the environment in which the protein is used, such as induction of immune response, enzymatic activity, or combinations thereof.

Protein activity release rate—the quantity of protein dissolved per unit time.

Protein crystal—protein molecules arranged in a crystal lattice. Protein crystals contain a pattern of specific protein—protein interactions that are repeated periodically in three dimensions. The protein crystals of this invention do not include amorphous solid forms or precipitates of proteins, such as those obtained by lyophilizing a protein solution.

Protein crystal formulation—a combination of protein crystals encapsulated within a polymeric carrier to form coated particles. The coated particles of the protein crystal formulation may have a spherical morphology and be microspheres of up to 500 micro meters in diameter or they may have some other morphology and be microparticulates. For the purposes of this application, "protein crystal formulations" are included in the term "compositions".

Protein delivery system—one or more of a protein crystal formulation or composition, a process for making the formulation or a method of administering the formulation to biological entities or means therefor.

Protein loading—the protein content of microspheres, as calculated as a percentage by weight of protein relative to the weight of the dry formulation. A typical range of protein loading is from 1–80%.

Protein release—the release of active protein from a polymeric carrier, as controlled by one or more of the following factors: (1) degradation of the polymer matrix; (2) rate of crystal dissolution within the polymer matrix; (3) diffusion of dissolved protein through the polymer matrix; (4) protein loading; and (5) diffusion of biological medium into the protein crystal/polymer matrix.

Prophylactically effective amount—an amount of a protein or nucleic acid crystal or crystal formulation or composition which is effective to prevent a condition in a living organism to whom it is administered over some period of time.

Reconstitution—dissolution of protein or nucleic acid crystals or crystal formulations or compositions in an appropriate buffer or pharmaceutical formulation.

Shelf stability—the loss of specific activity and/or changes in secondary structure from the native protein over time incubated under specified conditions.

Stability—the loss of specific activity and/or changes in secondary structure from the native protein over time while in solution under specified conditions.

Stabilization—the process of preventing the loss of specific activity and/or changes in secondary structure from the native proteins, by preparing formulations of protein crystals or DNA crystals or RNA crystals with excipients or ingredients.

Therapeutic protein—a protein as described above, which is administered to a living organism in a formulation or composition or a pharmaceutical formulation or composition. Therapeutic proteins include all of the protein types described herein.

Vaccine antigen—a protein derived from a pathogenic agent such as a virus, parasite, bacteria or tumor cell. The protein activity of such vaccine antigens is the induction of protective immune responses specific for a pathogenic agent or tumor.

Crystallinity

Crystallinity of macromolecules is of great value for their storage and delivery in vivo. However, few techniques exist for the preparation of large quantities of such crystalline macromolecules which are stable outside of the mother liquor. Crystals of proteins and nucleic acids must be handled with considerable care, since they are extremely fragile and contain a high proportion of solvent. It is well known in x-ray crystallography that the diffraction patterns from macromolecular crystals quickly degenerate upon dehydration in air. Normally, a crystal is carefully separated from its mother liquor and inserted into a capillary tube. The tube is sealed from the air using dental wax or silicone grease, along with a small amount of mother liquor inside to maintain hydration [McPherson, A., *Preparation and Analysis of Protein Crystals*, Robert E. Krieger Publishing, Malabar, p. 214 (1989)]. Another technique is to collect data from macromolecular crystals at cryogenic temperatures. The crystals are prepared and then rapidly cooled to prevent ice lattice formation in the aqueous medium. Instead of ice, a rigid glass forms, encasing the crystal with little damage. Crystals are then maintained at 100° K to prevent crystal disintegrations [Rodgers, D. W., in *Methods in Enzymology* (Eds., Carter, C. W. and Sweet, R. M.) Academic Press, v.276, p. 183 (1997)]. While this technique allows one to maintain crystals outside of their mother liquor, it cannot be used at temperatures higher than 100° K.

In principle, dried crystals can be prepared by lyophilization. However, this technique involves rapid cooling of the material and can be applied only to freeze stable products. The aqueous solution is first frozen to between −40 and −50°

C. Then, the ice is removed under vacuum. Ice formation is usually destructive to the protein crystal lattice, yielding a mixture of crystals and amorphous precipitate.

It is desirable to produce macromolecules, in the crystalline state, that are pure and stable under storage conditions at ambient temperatures. Such crystals constitute a particularly advantageous form of proteins or nucleic acids for dosage preparations of therapeutics and vaccines. The present invention provides formulations and compositions for storage of crystalline macromolecules as either solid particles or dispersed in a non-aqueous solvent. Furthermore, the invention may be applied to the storage of a single biological macromolecule or a mixture of macromolecules that do not interact with each other.

In another embodiment, this invention provides a method for rendering biological macromolecules suitable for storage in suspensions comprising replacing the mother liquor with a non-aqueous solvent. In yet another embodiment, the crystalline slurry can be rendered solid by spinning out the first solvent and washing the remaining crystalline solid using a second organic solvent to remove water, followed by evaporation of the non-aqueous solvent.

Non-aqueous slurries of crystalline therapeutic proteins are especially useful for subcutaneous delivery, while solid formulations are ideally suited for pulmonary administration. Pulmonary delivery is particularly useful for biological macromolecules which are difficult to deliver by other routes of administration. (See, for example, PCT patent applications Wo 96/32152, WO 95/24183 and WO 97/41833).

The proteins referred to below include protein crystals themselves, or nucleic acid crystals comprising DNA or RNA which encode those proteins upon cellular uptake.

This invention advantageously provides compositions and formulations of crystals of proteins or nucleic acids.

Stability of Encapsulated Crystals

Those of skill in the art will appreciate that protein stability is one of the most important obstacles to successful formulation of polymer microparticulate delivery systems that control the release of proteins. The stability of proteins encapsulated in polymeric carriers may be challenged at three separate stages: manufacture of the protein crystal composition, protein release from the resulting composition and in vivo stability after the protein release. During preparation of microparticles or microspheres containing soluble or amorphous proteins, the use of organic solvents and lyophilization are especially detrimental to protein stability. Subsequently, released proteins are susceptible to moisture-induced aggregation, thus resulting in permanent inactivation.

In order to achieve high protein stability during preparation of protein formulations and compositions according to the present invention, it is necessary to restrict the mobility of individual protein molecules—a result best achieved in the crystalline solid state. For the purpose of this application, solid state may be divided into two categories: amorphous and crystalline. The three-dimensional long-range order that normally exists in a crystalline material does not exist in the amorphous state. Furthermore, the position of molecules relative to one another is more random in the amorphous or liquid states, relative to the highly ordered crystalline state. Thus, amorphous proteins may be less stable than their crystalline counterparts.

FIG. 1 depicts the relative stability of the following molecular states of *Candida rugosa* lipase ("CRL"): crosslinked amorphous, liquid, crystalline in 20% organic solvent, crosslinked crystalline in 20% organic solvent, crosslinked crystalline without organic solvent. FIG. 1 shows that crystalline CRL retains 80% activity for more than 175 hours in 20% organic solvent. In contrast, both amorphous and soluble forms of the enzyme are completely inactivated within hours. The present invention advantageously utilizes the crystalline forms of proteins because of their superior stability characteristics.

Maintaining Crystallinity

In order to use protein crystals as the protein source for preparing protein formulations and compositions according to the present invention, the problem of protein crystal dissolution outside the crystallization solution ("mother liquor") had to be overcome. In order to maintain protein crystallinity and hence stability, in the production of the protein crystal formulations and compositions of this invention, several approaches may be used:

1. Crystals remain in the mother liquor in the course of producing protein crystals encapsulated with polymeric carriers. Many compounds used in protein crystallization, such as salts, PEG and organic solvents, are compatible with polymer processing conditions.

2. Kinetics of dissolution. The rate of crystal dissolution outside the mother liquor depends on conditions, such as pH, temperature, presence of metal ions, such as Zn, Cu and Ca and concentration of precipitants. By varying these conditions, one can slow down the dissolution of crystals for several hours. At the same time, the process of microparticulate formation is very fast and normally takes seconds to minutes to complete.

3. Dried protein crystals. The mother liquor can be removed by filtration and the remaining crystalline paste can be dried by air, under vacuum, by washing with water miscible organic solvents and/or by lyophilization.

4. Protein crystals can be chemically crosslinked to form non-dissolvable or slowly dissolvable crystals.

5. The crystal size and shape can be manipulated and controlled in the course of crystallization.

Thus, a range of crystal morphologies, each having different dissolution kinetics and subsequently different sustained release profiles compared to amorphous proteins, is available.

Protein Constituents

The protein constituents of the formulations and compositions of this invention may be those which are naturally or synthetically modified. They may be glycoproteins, phosphoproteins, sulphoproteins, iodoproteins, methylated proteins, unmodified proteins or contain other modifications. Such protein constituents may be any protein, including, for example, therapeutic proteins, prophylactic proteins, including antibodies, cleaning agent proteins, including detergent proteins, personal care proteins, including cosmetic proteins, veterinary proteins, food proteins, feed proteins, diagnostic proteins and decontamination proteins.

In one embodiment of this invention, such proteins have a molecular weight of greater than or equal to 10,000 Daltons. According to an alternate embodiment, that molecular weight is greater than or equal to 20,000 Daltons. According to another alternate embodiment, that molecular weight is greater than or equal to 30,000 Daltons. According to a further alternate embodiment, that molecular weight is greater than or equal to 40,000 Daltons. According to another alternate embodiment, that molecular weight is greater than or equal to 50,000 Daltons.

Included among such proteins are enzymes, such as, for example, hydrolases, isomerases, lyases, ligases, adenylate cyclases, transferases and oxidoreductases. Examples of hydrolases include elastase, esterase, lipase, nitrilase, amylase, pectinase, hydantoinase, asparaginase, urease, subtilisin, thermolysin and other proteases and lysozyme. Examples of lyases include aldolases and hydroxynitrile lyase. Examples of oxidoreductases include peroxidase, laccase, glucose oxidase, alcohol dehydrogenase and other dehydrogenases. Other enzymes include cellulases and oxidases.

Examples of therapeutic or prophylactic proteins include hormones such as insulin, glucogon-like peptide 1 and parathyroid hormone, antibodies, inhibitors, growth factors, postridical hormones, nerve growth hormones, blood clotting factors, adhesion molecules, bone morphogenic proteins and lectins trophic factors, cytokines such as TGF-β, IL-2, IL-4, α-IFN, β-IFN, γ-IFN, TNF, IL-6, IL-8, lymphotoxin, IL-5, Migration inhibition factor, GMCSF, IL-7, IL-3, monocyte-macrophage colony stimulating factors, granulocyte colony stimulating factors, multidrug resistance proteins, other lymphokines, toxoids, erythropoietin, Factor VIII, amylin, TPA, dornase-α,α-1-antitripsin, human growth hormones, nerve growth hormones, bone morphogenic proteins, urease, toxoids, fertility hormones, FSH and LSH.

Therapeutic proteins, such as the following, are also included:

leukocyte markers, such as CD2, CD3, CD4, CD5, CD6, CD7, CD8, CD11a, CD11b, CD11c, CD13, CD14, CD18, CD19, CE20, CD22, CD23, CD27 and its ligand, CD28 and its ligands B7.1, B7.2, B7.3, CD29 and its ligands, CD30 and its ligand, CD40 and its ligand gp39, CD44, CD45 and isoforms, Cdw52 (Campath antigen), CD56, CD58, CD69, CD72, CTLA-4, LFA-1 and TCR histocompatibility antigens, such as MHC class I or II antigens, the Lewis Y antigens, SLex, SLey, SLea and SLeb;

integrins, such as VLA-1, VLA-2, VLA-3, VLA-4, VLA-5, VLA-6 and LFA-1;

adhesion molecules, such as Mac-1 and p150,95;

selectins, such as L-selectin, P-selectin and E-selectin and their counterreceptors VCAM-1, ICAM-1, ICAM-2 and LFA-3;

interleukins, such as IL-1, IL-2, IL-3, IL-4, IL-5, IL-6, IL-7, IL-8, IL-10, IL-11, IL-12, IL-13, IL-14 and IL-15;

interleukin receptors, such as IL-1R, IL-2R, IL-4R, IL-5R, IL-6R, IL-7R, IL-8R, IL-10R, IL-11R, IL-12R, IL-13R, IL-14R and IL-15R;

chemokines, such as PF4, RANTES, MIP1α, MCP1, NAP-2, Groα, Groβ and IL-8;

growth factors, such as TNFalpha, TGFbeta, TSH, VEGF/VPF, PTHrP, EGF family, EGF, PDGF family, endothelin and gastrin releasing peptide (GRP);

growth factor receptors, such as TNFalphaR, RGFbetaR, TSHR, VEGFR/VPFR, FGFR, EGFR, PTHrPR, PDGFR family, EPO-R; GCSF-R and other hematopoietic receptors;

interferon receptors, such as IFNαR, IFNβR and IFNγR;

Igs and their receptors, such as IgE, FceRI and FceRII;

blood factors, such as complement C3b, complement C5a, complement C5b-9, Rh factor, fibrinogen, fibrin and myelin associated growth inhibitor.

The protein constituent of the formulations and compositions of this invention may be any natural, synthetic or recombinant protein antigen including, for example, tetanus toxoid, diptheria toxoid, viral surface proteins, such as CMV glycoproteins B, H and gCIII, HIV-1 envelope glycoproteins, RSV envelope glycoproteins, HSV envelope glycoproteins, EBV envelope glycoproteins, VZV envelope glycoproteins, HPV envelope glycoproteins, Influenza virus glycoproteins, Hepatitis family surface antigens; viral structural proteins, viral enzymes, parasite proteins, parasite glycoproteins, parasite enzymes and bacterial proteins.

Also included are tumor antigens, such as her2-neu, mucin, CEA and endosialin. Allergens, such as house dust mite antigen, lol p1 (grass) antigens and urushiol are included.

Toxins, such as pseudomonas endotoxin and osteopontin/uropontin, snake venom and bee venom are included.

Also included are glycoprotein tumor-associated antigens, for example, carcinoembryonic antigen (CEA), human mucins, her-2/neu and prostate-specific antigen (PSA) [R. A. Henderson and O. J. Finn, *Advances in Immunology*, 62, pp. 217–56 (1996)].

Administration and Biological Delivery

To date, therapeutic proteins have generally been administered by frequent injection, due to their characteristic negligible oral bioavailability and short plasma life. The protein crystal formulations and compositions of the present invention, which include microparticulate-based sustained release systems for protein drugs, advantageously permit improved patient compliance and convenience, more stable blood levels and potential dose reduction. The slow and constant release capabilities of the present invention advantageously permit reduced dosages, due to more efficient delivery of active protein. Significant cost savings may be achieved by using the protein formulations and compositions described herein.

Formulations and compositions comprising protein crystals in polymeric delivery carriers according to this invention may also comprise any conventional carrier or adjuvant used in vaccines, pharmaceuticals, personal care formulations and compositions, veterinary formulations, or oral enzyme supplementation. These carriers and adjuvants include, for example, Freund's adjuvant, ion exchangers, alumina, aluminum stearate, lecithin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, sodium chloride, zinc salts, colloidal silica, magnesium, trisilicate, cellulose-based substances and polyethylene glycol. Adjuvants for topical or gel base forms may include, for example, sodium carboxymethylcellulose, polyacrylates, polyoxyethylene-polyoxypropylene-block polymers, polyethylene glycol and wood wax alcohols.

According to one embodiment of this invention, protein crystals may be combined with any conventional materials used for controlled release administration, including pharmaceutical controlled release administration. Such materials include, for example, coatings, shells and films, such as enteric coatings and polymer coatings and films.

Protein formulations in polymeric delivery carriers and compositions (compositions) according to this invention, which may be devices, such as implantable devices and may be microparticulate protein delivery systems.

In one embodiment of this invention, the macromolecule crystals have a longest dimension between about 0.01 $\mu$m and about 500 $\mu$m, alternatively between about 0.1 $\mu$m and about 100 $\mu$m. The most preferred embodiment is that the protein crystal of protein crystal formulation components are between about 50 $\mu$m and about 100 $\mu$m in their longest dimension. Such crystals may have a shape selected from the group consisting of: spheres, needles, rods, plates, such as hexagons and squares, rhomboids, cubes, bipyramids and prisms.

According to the present invention, encapsulation of protein crystals or protein crystal formulations in polymeric carriers to make compositions may be carried out on protein crystals which are crosslinked or uncrosslinked. Such protein crystals may be obtained commercially or produced as illustrated herein.

Protein or nucleic acid crystals or crystal formulations and compositions according to this invention may be used as ingredients in personal care compositions, including cosmetics, such as creams, lotions, emulsions, foams, washes, compacts, gels, mousses, slurries, powders, sprays, pastes, ointments, salves, balms, drops, shampoos and sunscreens. In topical creams and lotions, for example, they may be used as humectants or for skin protection, softening, bleaching, cleaning, deproteinization, lipid removal, moisturizing, decoloration, coloration or detoxification. They may also be used as anti-oxidants in cosmetics.

According to this invention, any individual, including humans, animals and plants, may be treated in a pharmaceutically acceptable manner with a pharmaceutically effective amount of protein or nucleic acid crystals or a crystal formulation or composition for a period of time sufficient to treat a condition in the individual to whom they are administered over some period of time. Alternatively, individuals may receive a prophylactically effective amount of protein or nucleic acid crystals or crystal formulation or composition of this invention which is effective to prevent a condition in the individual to whom they are administered over some period of time.

Protein or nucleic acid crystals or crystal formulations or compositions may be administered alone, as part of a pharmaceutical, personal care or veterinary preparation, or as part of a prophylactic preparation, such as a vaccine, with or without adjuvant. They may be administered by parenteral or oral routes. For example, they may be administered by oral, pulmonary, nasal, aural, anal, dermal, ocular, intravenous, intramuscular, intraarterial, intraperitoneal, mucosal, sublingual, subcutaneous, or intracranial route. In either pharmaceutical, personal care or veterinary applications, protein or nucleic acid crystal or crystal formulations or compositions may be topically administered to any epithelial surface. Such epithelial surfaces include oral, ocular, aural, anal and nasal surfaces, which may be treated, protected, repaired or detoxified by application of protein or nucleic acid crystals or crystal formulations or compositions.

Pharmaceutical, personal care, veterinary or prophylactic formulations and compositions comprising protein or nucleic acid crystal or crystal formulations or compositions according to this invention may also be selected from the group consisting of tablets, liposomes, granules, spheres, microparticles, microspheres and capsules.

For such uses, as well as other uses according to this invention, protein or nucleic acid crystals or crystal formulations and compositions may be formulated into tablets. Such tablets constitute a liquid-free, dust-free form for storage of protein or nucleic acid crystal or crystal formulations or compositions which are easily handled and retain acceptable levels of activity or potency.

Alternatively, protein or nucleic acid crystals or crystal formulations or compositions may be in a variety of conventional depot forms employed for administration to provide reactive compositions. These include, for example, solid, semi-solid and liquid dosage forms, such as liquid solutions or suspensions, slurries, gels, creams, balms, emulsions, lotions, powders, sprays, foams, pastes, ointments, salves, balms and drops.

Protein or nucleic acid crystals on formulations or compositions according to this invention may also comprise any conventional carrier or adjuvant used in pharmaceuticals, personal care compositions or veterinary formulations. These carriers and adjuvants include, for example, Freund's adjuvant, ion exchangers, alumina, aluminum stearate, lecithin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, sodium chloride, zinc salts, colloidal silica, magnesium, trisilicate, cellulose-based substances and polyethylene glycol. Adjuvants for topical or gel base forms may include, for example, sodium carboxymethylcellulose, polyacrylates, polyoxyethylene-polyoxypropylene-block polymers, polyethylene glycol and wood wax alcohols.

The most effective mode of administration and dosage regimen of the protein or nucleic acid crystals or crystal formulations or compositions of this invention will depend on the effect desired, previous therapy, if any, the individual's health status or status of the condition itself and response to the protein or nucleic acid crystals or crystal formulations or compositions and the judgment of the treating physician or clinician. The protein or nucleic acid crystals or crystal formulations or compositions may be administered in any dosage form acceptable for pharmaceuticals, vaccinations, gene therapy, immunotherapy, personal care compositions or veterinary formulations, at one time or over a series of treatments.

The amount of the protein or nucleic acid crystals or crystal formulations or compositions which provides a single dosage will vary depending upon the particular mode of administration, formulation, dose level or dose frequency. A typical preparation will contain between about 0.01% and about 99%, preferably between about 1% and about 50%, protein or nucleic acid crystals (w/w). Alternatively, a preparation will contain between about 0.01% and about 80% protein crystals, preferably between about 1% and about 50%, protein crystals (w/w). Alternatively, a preparation will contain between about 0.01% and about 80% protein crystal formulation, preferably between about 1% and about 50%, protein crystal formulation(w/w).

Upon improvement of the individual's condition, a maintenance dose of protein or nucleic acid crystals or crystal formulations or compositions may be administered, if necessary. Subsequently, the dosage or frequency of administration, or both, may be reduced as a function of the symptoms, to a level at which the improved condition is retained. When the condition has been alleviated to the desired level, treatment should cease. Individuals may, however, require intermittent treatment on a long-term basis upon any recurrence of the condition or symptoms thereof.

Production of Crystals, Crystal Formulations and Compositions:

According to the one embodiment of this invention, crystals, crystal formulations and compositions are prepared by the following process: first, the protein or nucleic acid is crystallized. Next, excipients or ingredients selected from sugars, sugar alcohols, viscosity increasing agents, wetting or solubilizing agents, buffer salts, emulsifying agents, antimicrobial agents, antioxidants, and coating agents are added directly to the mother liquor. Alternatively, the crystals are suspended in an excipient solution, after the mother liquor is removed, for a minimum of 1 hour to a maximum of 24 hours. The excipient concentration is typically between about 0.01 to 30% W/W, which corresponds to a crystal concentration of 99.99 to 70% W/W, respectively. Most preferably, the excipient concentration is between about 0.1 to 10%, which corresponds to a crystal concentration of 99.9 to 90% W/W, respectively. The ingredient concentration is between about 0.01 to 90%. The crystal concentration is between about 0.01 to 95%. The mother liquor is then removed from the crystal slurry either by filtration or by centrifugation. Subsequently, the crystals are washed optionally with solutions of 50 to 100% one or more organic solvents such as, for example, ethanol, methanol, isopropanol or ethyl acetate, either at room temperature or at temperatures between −20°C to 25°C. The crystals are the dried either by passing a stream of nitrogen, air, or inert gas over the crystals. Alternatively, the crystals are dried by air drying or by lyophilization or by vacuum drying. The drying is carried out for a minimum 1 hour to a maximum of 72 hours after washing, until the moisture content of the final product is below 10% by weight, most preferably below 5%. Finally, micronizing of the crystals can be performed if necessary.

According to one embodiment of this invention, when preparing protein crystals, protein crystal formulations or compositions, enhancers, such as surfactants are not added during crystallization. Excipients or ingredients are added to the mother liquor after crystallization, at a concentration of between about 1–10% W/W, alternatively at a concentration of between about 0.1–25% W/W, alternatively at a concentration of between about 0.1–50% W/W. These concentrations correspond to crystal concentrations of 99–90% W/W, 99.9–75% W/W and 99.9–50% W/W, respectively. The excipient or ingredient is incubated with the crystals in the mother liquor for about 0.1–3 hrs, alternatively the incubation is carried out for 0.1–12 hrs, alternatively the incubation is carried out for 0.1–24 hrs.

In another embodiment of this invention, the ingredient or excipient is dissolved in a solution other than the mother liquor, and the protein crystals are removed from the mother liquor and suspended in the excipient or ingredient solution. The ingredient or excipient concentrations and the incubation times are the same as those described above.

Slow Release Forms and Vaccines

In another embodiment of this invention, encapsulation of lipases in polymeric carriers provide compositions useful to treat patients suffering from intestinal lipase deficiency. Such patients include those with pancreatic steatorrhea, due to advanced pancreatic insufficiency require oral lipase supplementation. Unfortunately, current therapeutic methods may not be flexible enough to protect the active lipase during transit through the gastro-intestinal tract and to release the enzyme activity where it is critically needed in the small bowel (See L. Guarner et al., "Fate of oral enzymes in pancreatic insufficiency," *Gut*, vol. 34, pp. 708–712, (1993)). The flexibility of the present invention in preparing slowly available active lipase solves the present problems often associated with lipase supplementation. According to one embodiment of this invention, the combination of encapsulated lipase crystals (compositions) and unencapsulated crosslinked lipase crystals or formulations provides a drug therapy regime in which enzyme activity is available early on from the unencapsulated crosslinked lipase. As this material undergoes proteolytic degradation, the encapsulated enzyme (composition) begins to release enzyme activity into the more distal bowel. A similar strategy may be used to solve other enzyme or therapeutic protein supplementation problems.

The present invention may also utilize other slow release methodologies, such as silicon based rings or rods which have been preloaded with encapsulated protein crystals containing hormones, antibodies or enzymes or compositions containing them. The purpose of this technique is to provide a constant level of protein to the bloodstream over a period of weeks or months. Such implants can be inserted intradermally and can be safely replaced and removed when needed.

Other formulations and compositions according to this invention include vaccine formulations and compositions comprising protein (antigen) crystals, adjuvant and encapsulating polymer(s). The protein antigen may be a viral glycoprotein, viral structural protein, viral enzyme, bacterial protein, or some engineered homolog of a viral or bacterial protein, or any immunopotentiating protein, such as a cytokine. One embodiment of such formulations or compositions involves a single vaccine injection containing microspheres having three or more different release profiles. In this way, antigen formulations or composition may be released over a sustained period sufficient to generate lasting immunity. By virtue of this formulation or composition, multiple antigen boosts may be in single unit form. The faster degrading preparation (composition) may contain an immunogenic adjuvant to enhance the immune response. One advantage of such a system is that by using protein crystals, the native three-dimensional structures of the epitopes are maintained and presented to the immune system in their native form.

Once the immune system is primed, there may be less need for an adjuvant effect. Therefore, in the slower degrading inoculations, a less immunogenic adjuvant may be included and possibly no adjuvant may be required in the slowest degrading microspheres of the formulations and compositions . In this way, patient populations in remote areas will not have to be treated multiple times in order to provide protection against infectious diseases. One of skill in the art of biological delivery of proteins will appreciate that many variations on this theme are feasible. Accordingly, the examples provided here are not intended to limit the invention.

In another embodiment of this invention, a combination vaccine could be produced, whereby immunity to multiple diseases is induced in a single injection. As discussed above, microspheres having different release profiles may be combined alone or in formulations and compositions and may include microspheres containing antigens from multiple infectious agents to produce a combination vaccine (formulations and compositions). For example, microspheres having multiple release profiles and containing antigen crystals of measles, mumps, rubella, polio and hepatitis B agents could be combined and administered to children. Alternatively, microspheres having multiple release profiles and containing crystals of different isolates of HIV gp120 could be combined to produce a vaccine for HIV-1 or HIV-2.

Another advantage of the present invention is that the protein crystals encapsulated within polymeric carriers and forming a composition comprising microspheres can be dried by lyophilization. Lyophilization, or freeze-drying allows water to be separated from the composition. The protein crystal composition is first frozen and then placed in a high vacuum. In a vacuum, the crystalline $H_2O$ sublimes, leaving the protein crystal composition behind containing only the tightly bound water. Such processing further stabilizes the composition and allows for easier storage and transportation at typically encountered ambient temperatures.

This feature is especially desirable for therapeutic proteins and vaccines which can be dispensed into single dose sterile containers ("ampules") or alternatively, any desired increment of a single dose as a slurry, in a formulation or a composition. The ampules containing the dispensed slurries, formulations or compositions can then be capped, batch frozen and lyophilized under sterile conditions. Such sterile containers can be transported throughout the world and stored at ambient temperatures. Such a system would be useful for providing sterile vaccines and therapeutic proteins to remote and undeveloped parts of the world. At the point of use, the ampule is rehydrated with the sterile solvent or buffer of choice and dispensed. Under this scenario, minimal or no refrigeration is required.

Protein Crystallization

Protein crystals are grown by controlled crystallization of protein from aqueous solutions or aqueous solutions containing organic solvents. Solution conditions that may be controlled include, for example, the rate of evaporation of solvent, organic solvents, the presence of appropriate co-solutes and buffers, pH and temperature. A comprehensive review of the various factors affecting the crystallization of proteins has been published by McPherson, *Methods Enzymol.*, 114, pp. 112–20 (1985).

McPherson and Gilliland, *J. Crystal Growth*, 90, pp. 51–59 (1988) have compiled comprehensive lists of proteins and nucleic acids that have been crystallized, as well as the conditions under which they were crystallized. A compendium of crystals and crystallization recipes, as well as a repository of coordinates of solved protein and nucleic acid structures, is maintained by the Protein Data Bank at the Brookhaven National Laboratory [http//www. pdb.bnl.gov; Bernstein et al., *J. Mol. Biol.*, 112, pp. 535–42 (1977)]. These references can be used to determine the conditions necessary for crystallization of a protein, as a prelude to the formation of appropriate protein crystals and can guide the crystallization strategy for other proteins. Alternatively, an intelligent trial and error search strategy can, in most instances, produce suitable crystallization conditions for many proteins, provided that an acceptable level of purity can be achieved for them [see, e.g., C. W. Carter, Jr. and C. W. Carter, *J. Biol. Chem.*, 254, pp. 12219–23 (1979)].

In general, crystals are produced by combining the protein to be crystallized with an appropriate aqueous solvent or aqueous solvent containing appropriate crystallization agents, such as salts or organic solvents. The solvent is combined with the protein and may be subjected to agitation at a temperature determined experimentally to be appropriate for the induction of crystallization and acceptable for the maintenance of protein activity and stability. The solvent can optionally include co-solutes, such as divalent cations, co-factors or chaotropes, as well as buffer species to control pH. The need for co-solutes and their concentrations are determined experimentally to facilitate crystallization.

It is critical to differentiate between amorphous precipitates and crystalline material. Crystalline material is a form of the solid state of matter, which is distinct from the amorphous solid state. Crystals display characteristic features including a lattice structure, characteristic shapes and optical properties such as refractive index and birefringence. A crystal consists of atoms arranged in a pattern that repeats periodically in three dimensions. In contrast, amorphous material is a non-crystalline solid form of matter, sometimes referred to as an amorphous precipitate. Such precipitates have no molecular lattice structure characteristic of the crystalline solid state and do not display birefringence or other spectroscopic characteristics typical of the crystalline forms of matter.

In an industrial-scale process, the controlled precipitation leading to crystallization can best be carried out by the simple combination of protein, precipitant, co-solutes and, optionally, buffers in a batch process. As another option, proteins may be crystallized by using protein precipitates as the starting material. In this case, protein precipitates are added to a crystallization solution and incubated until crystals form. Alternative laboratory crystallization methods, such as dialysis or vapor diffusion, can also be adopted. McPherson, supra and Gilliland, supra, include a comprehensive list of suitable conditions in their reviews of the crystallization literature.

Occasionally, in cases in which the crystallized protein is to be crosslinked, incompatibility between an intended crosslinking agent and the crystallization medium might require exchanging the crystals into a more suitable solvent system.

Many of the proteins for which crystallization conditions have already been described, may be used to prepare protein crystals according to this invention. It should be noted, however, that the conditions reported in most of the above-cited references have been optimized to yield, in most instances, a few large, diffraction quality crystals. Accordingly, it will be appreciated by those of skill in the art that some degree of adjustment of these conditions to provide a high yielding process for the large scale production of the smaller crystals used in making protein crystals the present invention may be necessary.

Crosslinking of Protein Crystals

According to one embodiment of this invention, for example, the release rate of the protein from the polymeric carrier (composition) may be slowed and controlled by using protein crystals that have been chemically crosslinked using a crosslinker, such as for example, a biocompatible crosslinker. Thus, once protein crystals have been grown in a suitable medium they may be crosslinked.

Crosslinking may be carried out using reversible crosslinkers, in parallel or in sequence. The resulting crosslinked protein crystals are characterized by a reactive multi-functional linker, into which a trigger is incorporated as a separate group. The reactive functionality is involved in linking together reactive amino acid side chains in a protein and the trigger consists of a bond that can be broken by altering one or more conditions in the surrounding environment (e.g., pH, temperature, or thermodynamic water activity). This is illustrated diagrammatically as:

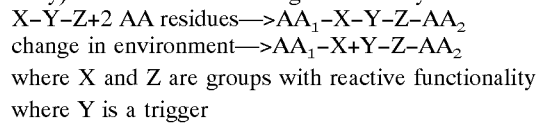

where X and Z are groups with reactive functionality where Y is a trigger where $AA_1$ and $AA_2$ represent reactive amino acid residues on the same protein or on two different proteins. The bond between the crosslinking agent and the protein may be a covalent or ionic bond, or a hydrogen bond. The change in surrounding environment results in breaking of the trigger bond and dissolution of the protein. Thus, when the crosslinks within protein crystals crosslinked with such reversible crosslinking agents break, dissolution of protein crystal begins and therefore the release of activity.

Alternatively, the reactive functionality of the crosslinker and the trigger may be the same, as in:

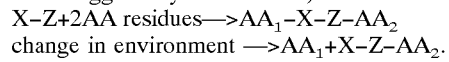

The crosslinker may be homofunctional (X=Y) or heterofunctional (X is not equal to Y). The reactive functionality X and Y may be, but not limited to the following functional groups (where R, R', R" and R''' may be alkyl, aryl or hydrogen groups):

I. Reactive acyl donors are exemplified by: carboxylate esters RCOOR', amides RCONHR', Acyl azides RCON$_3$, carbodiimides R–N=C=N–R', N-hydroxyimide esters, RCO—O—NR', imidoesters R—C=NH2$^+$(OR'), anhydrides RCO—O—COR', carbonates RO—CO—O—R', urethanes RNHCONHR', acid halides RCOHal (where Hal=a halogen), acyl hydrazides RCONNR'R", O-acylisoureas RCO—O—C=NR' (—NR"R'''), II. Reactive carbonyl groups are exemplified by: aldehydes RCHO and ketones RCOR', acetals RCO(H$_2$)R', ketals RR'CO$_2$R'R". Reactive carbonyl containing functional groups known to those well skilled in the art of protein immobilization and crosslinking are described in the literature [*Pierce Catalog and Handbook*, Pierce Chemical Company, Rockford, Ill. (1994); S. S. Wong, *Chemistry of Protein Conjugation and Cross-Linking*, CRC Press, Boca Raton, Fla. (1991)].

III. Alkyl or aryl donors are exemplified by: alkyl or aryl halides R-Hal, azides R—N$_3$, sulfate esters RSO$_3$R', phosphate esters RPO(OR'$_3$), alkyloxonium salts R$_3$O+, sulfonium R$_3$S+, nitrate esters RONO$_2$, Michael acceptors RCR'=CR'''COR", aryl fluorides ArF, isonitriles RN+≡C–, haloamines R$_2$N-Hal, alkenes and alkynes.

IV. Sulfur containing groups are exemplified by disulfides RSSR', sulfhydryls RSH, epoxides R$_2$C—$^O$CR'$_2$.

V. Salts are exemplified by alkyl or aryl ammonium salts R$_4$N+, carboxylate RCOO—, sulfate ROSO$_3$—, phosphate ROPO$_3$" and amines R$_3$N.

Table 1 below includes examples of triggers, organized by release mechanism. In Table 1, R= is a multifunctional crosslinking agent that can be an alkyl, aryl, or other chains with activating groups that can react with the protein to be crosslinked. Those reactive groups can be any variety of groups such as those susceptible to nucleophilic, free radical or electrophilic displacement including halides, aldehydes, carbonates, urethanes, xanthanes, epoxides among others.

TABLE 1

| Trigger | Examples | Release Conditions |
| --- | --- | --- |
| 1. Acid Labile Linkers | R-O-R e.g. Thp, MOM, Acetal, ketal Aldol, Michael adducts, esters | H$^+$ or Lewis Acidic catalysts |
| 2. Base Labile Linkers | R'OCO2-R' Carbonates R'O-CONR$_2$ Carbamates R$_2$'NCONR$_2$ Urethanes Aldol, Michael adducts, esters | Variety of basic media |
| 3. Fluoride Labile Linkers | R-OSiR$_3$ Various Si containing linkers | Aqueous F$^-$ |
| 4. Enzyme Labile Linkers | RCOOR, RCONR$_2$' | Free lipases, amidases, esterases |
| 5. Reduction Labile Linkers | Disulfide linkers that cleave via Hydrogenolysis Reductive Elimination R'-S-S-R | H$_2$ catalyst; Hydrides |

TABLE 1-continued

| Trigger | Examples | Release Conditions |
| --- | --- | --- |
| 6. Oxidation Labile Linkers | R-OSiR$_3$ Glycols R-CH(OH)—CH(OH)—R' | Oxidizing agents: e.g. H$_2$O$_2$, NaOCl, IO$_4^-$ Metal based oxidizers, other hypervalent oxidents |
| 7. Thio-labile linkers | R'-S-S-R | Thiols, e.g., Cys, DTT, mercaptoethanol |
| 8. Heavy Metal Labile Linkers | Various Allyl Ethers ROCH$_2$CH=CHR Alkyl, Acyl Allyl ester | Transition metal based reagents (Pd, Ir, Hg, Ag, Cu, Tb Rh) Pd (0) catalysts |
| 9. Photolabile Linkers DESYL groups in linker | O-nitrobenzyl (ONB) | light (hv) |
| 10. Free Radical Labile Linkers | Thiohydroxamate ester (Barton ester) | Free radical initiator |
| 11. Metal-chelate linked | Iron (III) diphenanthroline | Metal removal e.g. by chelation or precipitation |
| 12. Thermally Labile Linkers | Peroxides R-OO-R | Increase in temperature |
| 13. "Safety Catch" Labile Linkers | Methylthio-ethyl (Mte) Dithianes | Base; amines, others |

Additional examples of reversible crosslinkers are described in T. W. Green, *Protective Groups in Organic Synthesis*, John Wiley & Sons (Eds.) (1981). Any variety of strategies used for reversible protecting groups can be incorporated into a crosslinker suitable for producing crosslinked protein crystals capable of reversible, controlled solubilization. Various approaches are listed, in Waldmann's review of this subject, in *Angewante Chemie Inl. Ed. Engl.*, 35, p. 2056 (1996).

Other types of reversible crosslinkers are disulfide bond-containing crosslinkers. The trigger breaking crosslinks formed by such crosslinkers is the addition of reducing agent, such as cysteine, to the environment of the crosslinked protein crystals.

Disulfide crosslinkers are described in the *Pierce Catalog and Handbook* (1994–1995) and more recently in "Bioconjugate Techniques", By G. T. Hermanson, (1996), Academic Press, Division of Harcourt Brace & Company, 525 B Street, Suite 1900, San Diego, Calif. 92101-4495.
Examples of Such Crosslinkers Include:
Homobifunctional (Symmetric)
DSS—Dithiobis(succinimidylpropionate), also know as Lomant's Reagent
DTSSP—3-3'-Dithiobis(sulfosuccinimidylpropionate), water soluble version of DSP
DTBP—Dimethyl 3,3'-dithiobispropionimidate.HCl
BASED—Bis-(β-[4-azidosalicylamido]ethyl)disulfide
DPDPB—1,4-Di-(3'-[2'-pyridyldithio]-propionamido) butane.
Heterobifunctional (Asymmetric)
SPDP—N-Succinimidyl-3-(2-pyridyldithio)propionate
LC-SPDP—Succinimidyl-6-(3-[2-pyridyldithio] propionate)hexanoate
Sulfo-LC-SPDP—Sulfosuccinimidyl-6-(3-[2-pyridyldlthio] propionate)hexanoate, water soluble version of LC-SPDP APDP—N-(4-[p-azidosalicylamido]butyl)-3'-(2'-pyridyldithio) propionamide
SADP—N-Succinimidyl(4-azidophenyl)1,3'-dithiopropionate
Sulfo-SADP—Sulfosuccinimidyl(4-azidophenyl) 1,3'-dithiopropionate, water soluble version of SADP
SAED—Sulfosuccinimidyl-2-(7-azido-4-methycoumarin-3-acetamide)ethyl-1,3'dithiopropionate
SAND—Sulfosuccinimidyl-2-(m-azido-o-nitrobenzamido) ethyl -1,3'-dithiopropionate
SASD—Sulfosuccinimidyl-2-(p-azidosalicylamido)ethyl -1,3'-dithiopropionate
SMPB—Succinimidyl-4-(p-maleimidophenyl)butyrate
Sulfo-SMPB—Sulfosuccinimidyl-4-(p-maleimidophenyl) butyrate
SMPT—4-Succinimidyloxycarbonyl-methyl-α-(2-pyridylthio) toluene
Sulfo-LC-SMPT—Sulfosuccinimidyl-6-(α-methyl-α-(2-pyridylthio)toluamido)hexanoate.

In particular, see Part II, Chapters 3–5 on Zero-length Cross-linkers, Homobifunctional Cross-linkers and Heterobifunctional Cross-linkers in "Bioconjugate Techniques", By G. T. Hermanson, (1996), Academic Press, Division of Harcourt Brace & Company, 525 B Street, Suite 1900, San Diego, Calif. 92101-4495.

Crosslinked protein crystals useful in the protein formulations of the present invention may also be prepared according to the methods set forth in PCT patent application PCT/US91/05415.

Encapsulation of Protein Crystals in Polymeric Carriers

According to one embodiment of this invention, compositions are produced when protein crystals are encapsulated in at least one polymeric carrier to form microspheres by virtue of encapsulation within the matrix of the polymeric carrier to preserve their native and biologically active tertiary structure. The crystals can be encapsulated using various biocompatible and/or biodegradable polymers having unique properties which are suitable for delivery to different biological environments or for effecting specific functions. The rate of dissolution and, therefore, delivery of active protein is determined by the particular encapsulation technique, polymer composition, polymer crosslinking, polymer thickness, polymer solubility, protein crystal geometry and degree and, if any, of protein crystal crosslinking Protein crystals or formulations to be encapsulated are suspended in a polymeric carrier which is dissolved in an organic solvent. The polymer solution must be concentrated enough to completely coat the protein crystals or formulations after they are added to the solution. Such an amount is one which provides a weight ratio of protein crystals to polymer between about 0.02 and about 20, preferably between about 0.1 and about 2. The protein crystals are contacted with polymer in solution for a period of time between about 0.5 minutes and about 30 minutes, preferably between about 1 minutes and about 3 minutes. The crystals should be kept suspended and not allowed to aggregate as they are coated by contact with the polymer.

Following that contact, the crystals become coated and are referred to as nascent microspheres. The nascent microspheres increase in size while coating occurs. In a preferred embodiment of the invention, the suspended coated crystals or nascent microspheres along with the polymeric carrier and organic solvent are transferred to a larger volume of an aqueous solution containing a surface active agent, known as an emulsifier. In the aqueous solution, the suspended nascent microspheres are immersed in the aqueous phase, where the organic solvent evaporates or diffuses away from the polymer. Eventually, a point is reached where the polymer is no longer soluble and forms a precipitated phase encapsulating the protein crystals or formulations to form a composition. This aspect of the process is referred to as hardening of the polymeric carrier or polymer. The emulsifier helps to reduce the interfacial surface tension between the various phases of matter in the system during the hardening phase of the process. Alternatively, if the coating polymer has some inherent surface activity, there may be no need for addition of a separate surface active agent.

Emulsifiers useful to prepare encapsulated protein crystals according to this invention include poly(vinyl alcohol) as exemplified herein, surfactants and other surface active agents which can reduce the surface tension between the polymer coated protein crystals or polymer coated crystal formulations and the solution.

Organic solvents useful to prepare the microspheres of the present invention include methylene chloride, ethyl acetate, chloroform and other non-toxic solvents which will depend on the properties of the polymer. Solvents should be chosen that solubilize the polymer and are ultimately non-toxic.

A preferred embodiment of this invention is that the crystallinity of the protein crystals is maintained during the encapsulation process. The crystallinity is maintained during the coating process by using an organic solvent in which the crystals are not soluble. Subsequently, once the coated crystals are transferred to the aqueous solvent, rapid hardening of the polymeric carrier and sufficient coating of the crystals in the previous step shields the crystalline material from dissolution. In another embodiment, the use of crosslinked protein crystals facilitates maintenance of crystallinity in both the aqueous and organic solvents.

The polymers used as polymeric carriers to coat the protein crystals can be either homo-polymers or co-polymers. The rate of hydrolysis of the microspheres is largely determined by the hydrolysis rate of the individual polymer species. In general, the rate of hydrolysis decreases as follows: polycarbonates>polyesters>polyurethanes>polyorthoesters>polyamides. For a review of biodegradable and biocompatible polymers, see W. R. Gombotz and D. K. Pettit, "Biodegradable polymers for protein and peptide drug delivery", Bioconjugate Chemistry, vol. 6, pp. 332–351 (1995).

In a preferred embodiment, the polymeric carrier is composed of a single polymer type such as PLGA. In a next preferred embodiment, the polymeric carrier can be a mixture of polymers such as 50% PLGA and 50% albumin.

Other polymers useful as polymeric carriers to prepare encapsulated protein crystals according to this invention include biocompatinie/biodegradable polymers selected from the group consisting of poly (acrylic acid), poly (cyanoacrylates), poly (amino acids), poly (anhydrides), poly (depsipeptide), poly (esters), such as poly (lactic acid) or PLA, poly (b-hydroxybutryate), poly (caprolactone) and poly (dioxanone); poly (ethylene glycol), poly (hydroxypropyl)methacrylamide, poly [(organo) phosphazene], poly (ortho esters), poly (vinyl alcohol), poly (vinylpyrrolidone), maleic anhydride-alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polysaccharides, blends and copolymers thereof. Other useful polymers are described in J. Heller and R. W. Balar, "Theory and Practice of Controlled Drug Delivery from Biodegradable Polymers," Academic Press, New York, N.Y., (1980); K. O. R. Lehman and D. K. Dreher, Pharmaceutical Technology, vol. 3, pp. 5-__, (1979); E. M. Ramadan, A.

El-Helw and Y. El-Said, Journal of Microencapsulation, vol. 5, p. 125 (1988). The preferred polymer will depend upon the particular protein component of the protein crystals used and the intended use of the encapsulated crystals (formulations and compositions). Alternatively, the solvent evaporation technique may be used for encapsulating protein crystals (see D. Babay, A. Hoffmann and S. Benita, Biomaterials vol. 9, pp. 482–488 (1988).

In a preferred embodiment of this invention, protein crystals are encapsulated in at least one polymeric carrier using a double emulsion method, as illustrated herein, using a polymer, such as polylactic-co-glycolyic acid. In a most preferred embodiment of this invention, the polymer is Polylactic-co-glycolyic acid ("PLGA" ). PLGA is a co-polymer prepared by polycondensation reactions with lactic acid ("L") and glycolic acid ("G" ). Various ratios of L and G can be used to modulate the crystallinity and hydrophobicity of the PLGA polymer. Higher crystallinity of the polymer results in slower dissolution. PLGA polymers with 20–70% G content tend to be amorphous solids, while high level of either G or L result in good polymer crystallinity. For more information on preparing PLGA, see D. K. Gilding and A. M. Reed, "Biodegradable polymers for use in surgery-poly(glycolic)/poly(lactic acid) homo and copolymers: 1., *Polymer* vol. 20, pp. 1459–1464 (1981). PLGA degrades after exposure to water by hydrolysis of the ester bond linkage to yield non-toxic monomers of lactic acid and glycolic acid.

In another embodiment, double-walled polymer coated microspheres may be advantageous. Double-walled polymer coated microspheres may be produced by preparing two separate polymer solutions in methylene chloride or other solvent which can dissolve the polymers. The protein crystals are added to one of the solutions and dispersed. Here, the protein crystals become coated with the first polymer. Then, the solution containing the first polymer coated protein crystals is combined with the second polymer solution. [See Pekarek, K. J.; Jacob, J. S. and Mathiowitz, E. Double-walled polymer microspheres for controlled drug release, Nature, 367, 258–260]. Now, the second polymer encapsulates the first polymer which is encapsulating the protein crystal. Ideally, this solution is then dripped into a larger volume of an aqueous solution containing a surface active agent or emulsifier. In the aqueous solution, the solvent evaporates from the two polymer solutions and the polymers are precipitated.

The above process can be performed using either protein crystals, DNA or RNA crystals, of formulations of any of these to produce compositions.

Formulations according to this invention comprise a protein crystal, and, at least one ingredient. Such formulations are characterized by at least a 60 fold greater shelf life when stored at 50° C. than the soluble form of said protein in solution at 50° C., as measured by $T_{1/2}$. Alternatively, they are characterized by at least a 59 fold greater shelf life when stored at 40° C. and 75% humidity than the nonformulated form of said protein crystal when stored at 40° C and 75% humidity, as measured by $T_{1/2}$. Alternatively, they are characterized by at least a 60% greater shelf life when stored at 50° C. than the nonformulated form of said protein crystal when stored at 50° C, as measured by $T_{1/2}$. Alternatively, they are characterized by the loss of less than 20% α-helical structural content of the protein after storage for 4 days at 50° C., wherein the soluble form of said protein loses more than 50% of its a-helical structural content after storage for 6 hours at 50° C, as measured by FTIR. Alternatively, they are characterized by the loss of less than 20% α-helical structural content of the protein after storage for 4 days at 50° C, wherein the soluble form of said protein loses more than 50% of its α-helical structural content after storage for 6 hours at 50° C, as measured by FTIR, and wherein said formulation is characterized by at least a 60 fold greater shelf life when stored at 50° C than the soluble form of said protein in solution at 50° C., as measured by $T_{1/2}$.

Compositions according to this invention comprise one of the above described protein crystal formulations, and, at least one polymeric carrier, wherein said formulation is encapsulated within a matix of said polymeric carrier.

Alternatively, compositions according to this invention comprise formulations of a protein crystal and at least one ingredient. Such compositions may be characterized by at least a 60 fold greater shelf life when stored at 50° C. than the soluble form of said protein in solution at 50° C., as measured by $T_{1/2}$. Alternatively, they are characterized by at least a 59 fold greater shelf life when stored at 40° C. and 75% humidity than the nonformulated form of said protein crystal when stored at 40° C. and 75% humidity, as measured by $T_{1/2}$. Alternatively, they are characterized by at least a 60% greater shelf life when stored at 50° C. than the nonformulated form of said protein crystal when stored at 50° C, as measured by $T_{1/2}$. Alternatively they are characterized by the loss of less than 20% α-helical structural content of the protein after storage for 4 days at 50° C., wherein the soluble form of said protein loses more than 50% of its α-helical structural content after storage for 6 hours at 50° C., as measured by FTIR. Alternatively, they are characterized by the loss of less than 20% α-helical structural content of the protein after storage for 4 days at 50° C., wherein the soluble form of said protein loses more than 50% of its a-helical structural content after storage for 6 hours at 50° C., as measured by FTIR, and wherein said formulation is characterized by at least a 60 fold greater shelf life when stored at 50° C. than the soluble form of said protein in solution at 50° C., as measured by $T_{1/2}$.

In order that this invention may be better understood, the following examples are set forth. These examples are for the purpose of illustration only and are not to be construed as limiting the scope of the invention in any manner.

EXAMPLES

Example 1

Lipase

*Candida rugosa* Lipase Crystallization:

Materials:

A—*Candida rugosa* lipase powder

B—Celite powder (diatomite earth)

C—MPD (2-Methyl-2,4-Pentanediol)

D—5 mM Ca acetate buffer pH 4.6

E—Deionized water

Procedure:

A 1 kg aliquot of lipase powder was mixed well with 1 kg of celite and then 22 L of distilled water was added. The mixture was stirred to dissolve the lipase powder. After dissolution was complete, the pH was adjusted to 4.8 using acetic acid. Next, the solution was filtered to remove celite and undissolved materials. Then, the filtrate was pumped through a 30 k cut-off hollow fiber to remove all the proteins that were less than 30 kD molecular weight. Distilled water was added and the lipase filtrate was pumped through the hollow fiber until the retentate conductivity was equal to the conductivity of the distilled water. At this point, the addition of distilled water was stopped and 5 mm Ca-acetate buffer was added. Next, Ca-acetate buffer was delivered by pumping through the hollow fiber until the conductivity of the retentate was equal to the conductivity of the Ca-acetate buffer. At that point, addition of the buffer was stopped. The lipase solution was concentrated to 30 mg/ml solution. The crystallization was initiated by pumping MPD slowly into the lipase solution while stirring. Addition of MPD was continued until a 20% vol/vol of MPD was reached. The mixture was stirred for 24 hr or until 90% of the protein had crystallized. The resulting crystals were washed with crystallization buffer to remove all the soluble material from the crystals. Then, the crystals were suspended in fresh crystallization buffer to achieve a protein concentration of 42 mg/ml.

Example 2

Formulation of Lipase Crystals Using Sucrose as Excipient:

In order to enhance the stability of lipase crystals during drying and storage the crystals were formulated with excipients. In this example, lipase crystals were formulated in the slurry form in the presence of mother liquor before drying. Sucrose (Sigma Chemical Co., St. Louis, Mo.) was added to lipase crystals in mother liquor as an excipient. Sufficient sucrose was added to lipase crystals at a protein concentration of 20 mgs/ml in mother liquor (10 mM sodium acetate buffer, pH 4.8 containing 10 mM Calcium chloride and 20% MPD) to reach a final concentration of 10%. The resulting suspension was tumbled at room temperature for 3 hr. After treatment with sucrose, the crystals were separated from the liquid by centrifugation as described in Example 6, method 4 or 5.

Example 3

Formulation of Lipase Crystals Using Trehalose as Excipient:

The lipase crystals were formulated as in Example 2, by adding trehalose, instead of sucrose, (Sigma Chemical Co., St. Louis, Mo.), to a final concentration of 10% in mother liquor. The resulting suspension was tumbled at room temperature for 3 hr and the crystals were separated from the liquid by centrifugation as described in Example 6, method 4 or 5.

Example 4

Formulation of Lipase Crystals Using Polyethylene Oxide (PEO) as Excipient:

Lipase crystals were formulated using 0.1% polyethylene oxide in water as follows. The crystals, in the mother liquor at 20 mg/ml were separated from the mother liquor by centrifugation at 1000 rpm in a Beckman GS-6R bench top centrifuge equipped with swinging bucket rotor. Next, the crystals were suspended in 0.1% polyethylene oxide for 3 hrs (Sigma Chemical Co., St. Louis, Mo.) and then separated by centrifugation, as described in Example 6, method 4 or 5.

Example 5

Formulation of Lipase Crystals Using Methoxypolyethylene Glycol (MOPEG) as Excipient:

Lipase crystals were formulated as in Example 2, by adding 10% methoxypoly ethylene glycol, instead of sucrose, (final concentration) (Sigma Chemical Co., St. Louis, Mo.) in mother liquor and separating after 3 hrs by centrifugation, as in Example 6, method 4 or 5.

Example 6

Methods of Drying Crystal Formulations:

Method 1. $N_2$ Gas Drying at Room Temperature

Crystals as prepared in Examples 1, 10, 14 and 21 were separated from the mother liquor containing excipient by centrifugation at 1000 rpm in a Beckman GS-6R bench top centrifuge equipped with swinging bucket rotor in a 50 ml Fisher brand Disposable centrifuge tube (Polypropylene). The crystals were then dried by passing a stream of nitrogen at approximately 10 psi pressure into the tube overnight.

Method 2. Vacuum Oven Drying

Crystals as prepared in Examples 1, 10, 14 and 21 were first separated from the mother liquor/excipient solution using centrifugation at 1000 rpm in a Beckman GS-6R bench top centrifuge equipped with swinging bucket rotor in a 50 ml Fisher brand Disposable polypropylene centrifuge tube. The wet crystals were then placed in a vacuum oven at 25 in Hg (VWR Scientific Products) at room temperature and dried for at least 12 hours.

Method 3. Lyophilization

Crystals as prepared in Examples 1, 10, 14 and 21 were first separated from the mother liquor/excipient solution using centrifugation at 1000 rpm in a Beckman GS-6R bench top centrifuge equipped with swinging bucket rotor in a 50 ml Fisher brand Disposable polypropylene centrifuge tube. The wet crystals were then freeze dried using a Virtis Lyophilizer Model 24 in semistoppered vials. The shelf temperature was slowly reduced to −40° C. during the freezing step. This temperature was held for 16 hrs. Secondary drying was then carried out for another 8 hrs.

Method 4. Organic Solvent and Air Drying

Crystals as prepared in Examples 1, 10, 14 and 21 were first separated from the mother liquor/excipient solution using centrifugation at 1000 rpm in a Beckman GS-6R bench top centrifuge equipped with swinging bucket rotor in a 50 ml Fisher brand Disposable polypropylene centrifuge tube. The crystals were then suspended in an organic solvent like ethanol or isopropanol or ethyl acetate or other suitable solvents, centrifuged, the supernatant was decanted and air dried at room temperature in the fume hood for two days.

Method 5. Air Drying at Room Temperature

Crystals as prepared in Examples 1, 10, 14 and 21 were separated from the mother liquor containing excipient by centrifugation at 1000 rpm in a Beckman GS-6R bench top centrifuge equipped with swinging bucket rotor in a 50 ml Fisher brand Disposable centrifuge tube (Polypropylene). Subsequently, the crystals were allowed to air dry in the fume hood for two days.

Example 7

Soluble Lipase Sample Preparation:

For comparison, a sample of soluble lipase was prepared by dissolving lipase crystals to 20 mg/ml in phosphate buffered saline, pH 7.4.

Figure 2:
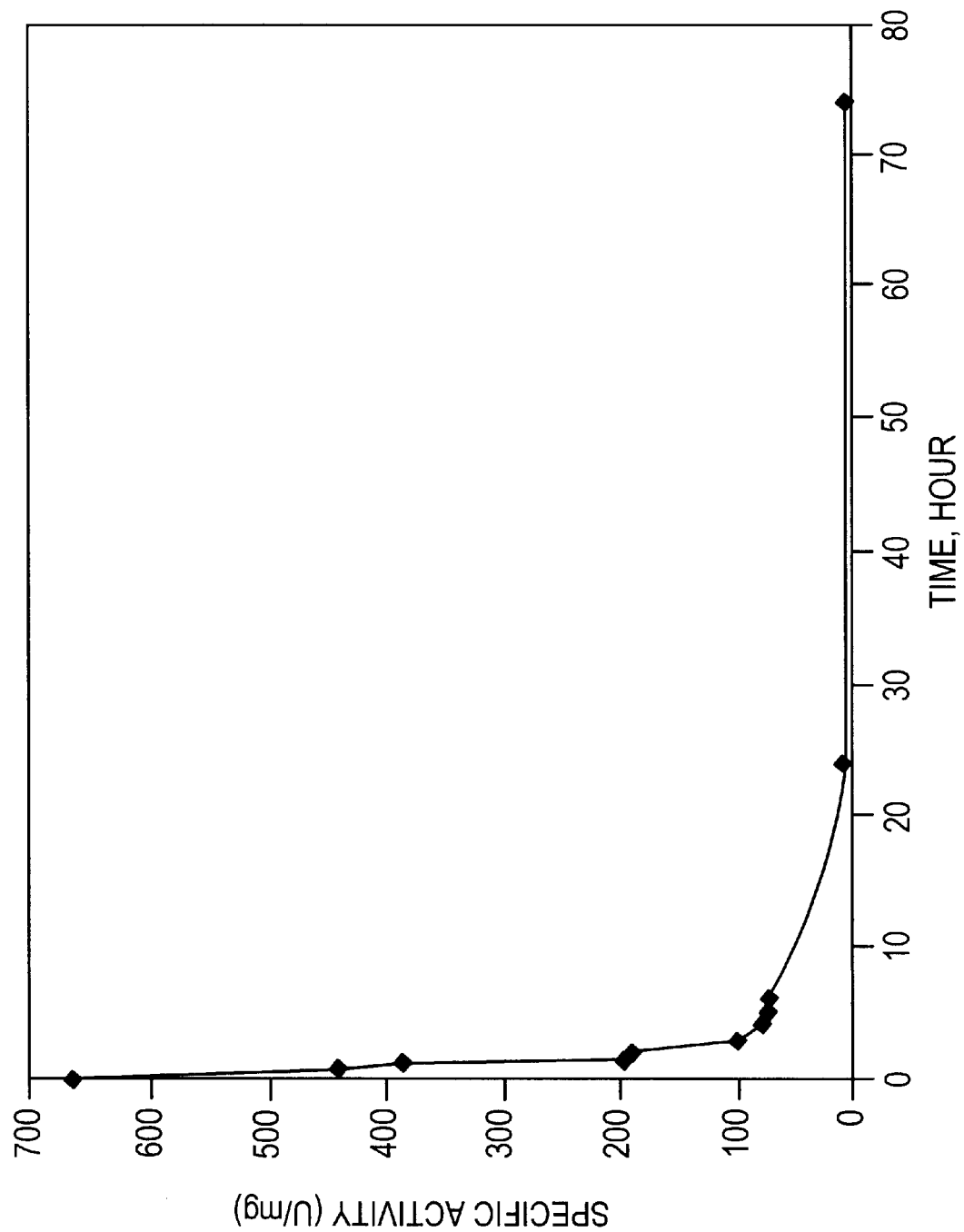
FIG. 2 depicts the specific activity of soluble lipase over time at 40° C.

FIG. 2 shows the stability for soluble lipase. Specific activity decreases extremely rapidly with time. Within 2–3 hours, the specific activity decreases from about 660 μmoles/min/mg protein to about 100 μmoles/min/mg protein or an approximate 85% decrease. The $T_{1/2}$ for soluble lipase was calculated to be 1.12 hours.

Example 8

Olive Oil Assay for Measuring Lipase Activity:

Lipase crystals from Examples 1–7 were assessed for activity against olive oil in pH 7.7 buffer. The assay was carried out titrimetrically using slight modifications to the procedure described in *Pharmaceutical Enzymes—Properties and Assay Methods*, R. Ruyssen and A. Lauwers, (Eds.), Scientific Publishing Company, Ghent, Belgium (1978).

Reagents:
1. Olive oil emulsion:
   16.5 gm of gum arabic (Sigma) was dissolved in 180 ml of water, 20 ml of olive oil (Sigma) and emulsified using a Quick Prep mixer for 3 minutes.
2. Titrant : 0.05 M NaOH
3. Solution A: 3.0 M NaCl
4. Solution B: 75 mM $CaCl_2 \cdot 2H_2O$
5. Mix: 40 ml of Solution A was combined with 20 ml of Solution B and 100 ml of $H_2O$.
6. 0.5% Albumin:
7. Lipase Substrate Solution (solution 7) was prepared by adding 50 ml of olive oil emulsion (solution 1) to 40 ml of Mix (solution 5) and 10 ml of 0.5% albumin (solution 6).

Assay Procedure

The lipase substrate solution (solution 7) was warmed to 37° C. in a water bath. First, 20 ml of substrate was added to a reaction vessel and the pH was adjusted to 7.7 using 0.05 M NaOH (solution 2) and equilibrated to 37° C. with stirring. The reaction was initiated by adding enzyme. The reaction progress was monitored by titrating the mixture of enzyme and substrate with 0.05 M NaOH to maintain the pH at 7.7.

The specific activity ($\mu$moles/min/mg protein) was equal to the initial rate×1000×concentration of the titrant/the amount of enzyme. The zero point was determined by running the reaction without enzyme, i.e., using buffer in the place of enzyme in the reaction mixture.

Example 9

Activity:

The shelf activity of the dried crystals from Examples 1–5 was measured using the olive oil assay as described in Example 8. Dried crystals (5 mg) were dissolved in 1 ml of phosphate buffered saline ("PBS"), pH 7.4 and the activity was measured using olive oil as substrate.

Shelf Stability:

The shelf stability of dried crystalline lipase formulations from Examples 2–5 was carried out in a humidity chamber controlled at 75% relative humidity and 40° C. temperature (HOTPACK). The activity of the crystals was measured by dissolving 5 mg of the dried samples in PBS buffer, pH 7.4, measuring the activity in the olive oil assay and then comparing with the initial results.

Crystal Formulations Dried by Method 5

Figure 3:
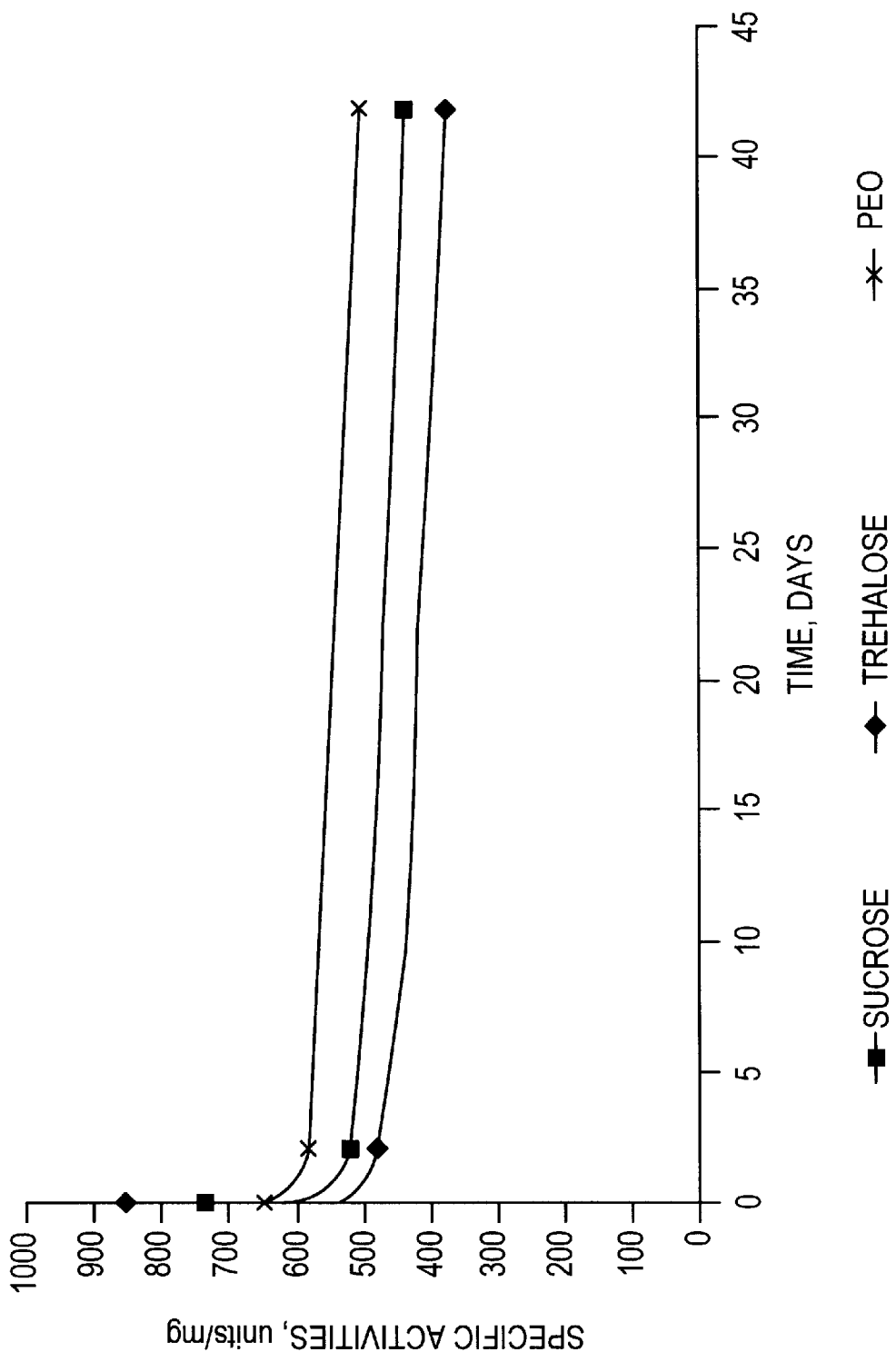
FIG. 3 depicts the shelf stabilities of lipase crystal formulations dried by method 1 at 40° C. and 75% humidity.

FIG. 3 shows the shelf stability profile of lipase crystals formulated with sucrose, trehalose and PEO. When dried by method 5, PEO was the most protective excipient, followed by sucrose and then trehalose.

Crystal Formulations Dried by Method 4

Figure 4:
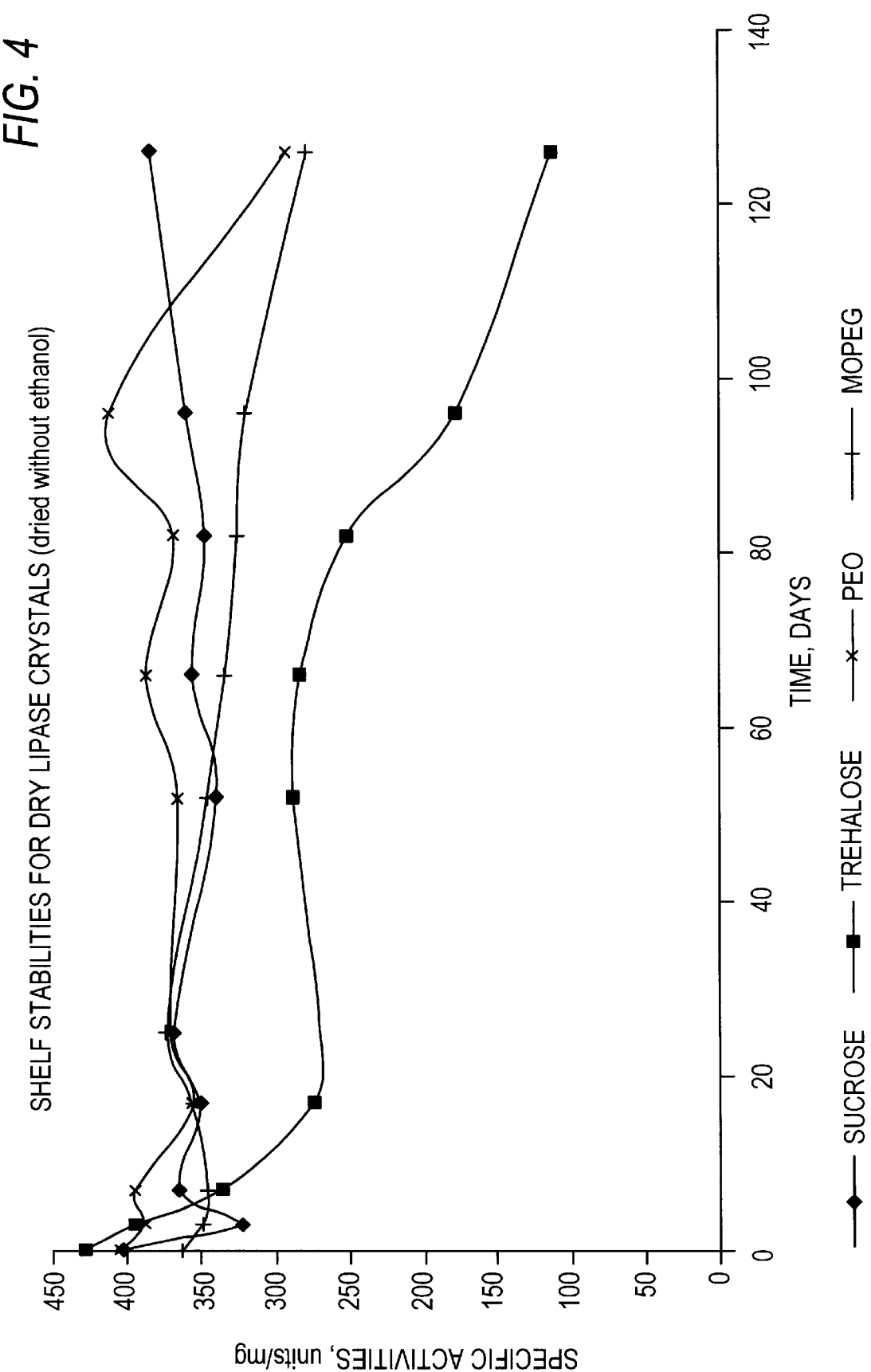
FIG. 4 depicts the shelf stabilities of lipase crystal formulations dried by method 4 at 40° C. and 75% humidity.

FIG. 4 shows the shelf stability profile of lipase crystals formulated with sucrose, trehalose, PEO and MOPEG. When dried by method 4, the excipients PEO, sucrose and MOPEG were similar in their ability to preserve enzyme activity as measured by their effect on the $T_{1/2}$. Trehalose was less protective of lipase activity than the other excipients.

Shelf Stability

The time required for the specific activity of the enzyme to decrease by 50% is known as the $T_{1/2}$. Table 2 shows the effect on the $T_{1/2}$ of the specific activity for formulations of dried lipase crystals. For lipase, sucrose was the most protective excipient, followed by polyethylene oxide (PEO), methoxypoly ethylene glycol (MOPEG) and finally trehalose. Sucrose was more than 10-fold more protective, as measured by its effect on $T_{1/2}$ of specific activity.

TABLE 2

Lipase at 40° C. and 75% humidity
Dried Lipase Crystals

| Excipients | $T_{1/2}$(days) |
|---|---|
| none | 1.52 |
| Sucrose | 1092 |
| Trehalose | 90 |
| PEO | 835 |
| MOPEG | 434 |
| Soluble lipase | 0.0468 (1.124 hrs) |

The $T_{1/2}$ was calculated from the shelf life data by non-linear regression analysis using the Sigma Plot program. Table 2 shows that formulations of lipase were 1,923 fold more stable than soluble when PEO was used as the excipient. In addition, formulations of lipase were 23,300 fold more stable than soluble lipase when sucrose was used as the excipient (Table 2). Formulations using MOPEG and PEO as excipients with lipase crystals were 9,270 and 17,800 fold more stable than soluble lipase (Table 2).

The stability of the formulated crystals relative to the non-formulated crystals was greatly enhanced, as shown in Table 2. For example, crystals formulated with trehalose were 59 fold more stable than non-formulated lipase crystals made without an excipient at 40° C., as shown in Table 2. Similarly, crystals formulated with MOPEG were 286 fold more stable than non-formulated crystals and crystals formulated with PEO were 549 fold more stable than non-formulated lipase crystals made without an excipient at 40° C., as shown in Table 2. Finally, crystals formulated with sucrose were 718 fold more stable than non-formulated lipase crystals made without an excipient at 40° C., as shown in Table 2.

Moisture Content:

Moisture content was determined by the Karl Fischer method according to manufacturer's instructions using a Mitsubishi CA-06 Moisture Meter equipped with a VA-06 Vaporizer (Mitsubishi Chemical Corporation, Tokyo, Japan).

TABLE 3

Moisture content lipase crystal formulations

| | % Moisture | | | |
|---|---|---|---|---|
| TIME, DAYS | SUCROSE | TREHALOSE | PEO | MOPEG |
| 0 | 7.23 | 5.58 | 8.56 | 7.03 |
| 129 | 11.11 | 10.45 | 10.43 | 10.01 |

Crystallinity:

The crystal integrity of the formulations were measured by quantitative microscopic observations. In order to visualize whether the crystals were maintained their shape after drying, the dried crystals were examined under an Olympus BX60 microscope equipped with DXC-970MD 3CCD Color Video Camera with Camera Adapter (CMA D2) with Image ProPlus software. Samples of dried crystals were covered with a glass coverslip, mounted and examined under 10× magnification, using an Olympus microscope with an Olympus UPLAN F1 objective lens 10×/0.30 PH1 (phase contrast).

Figure 5:
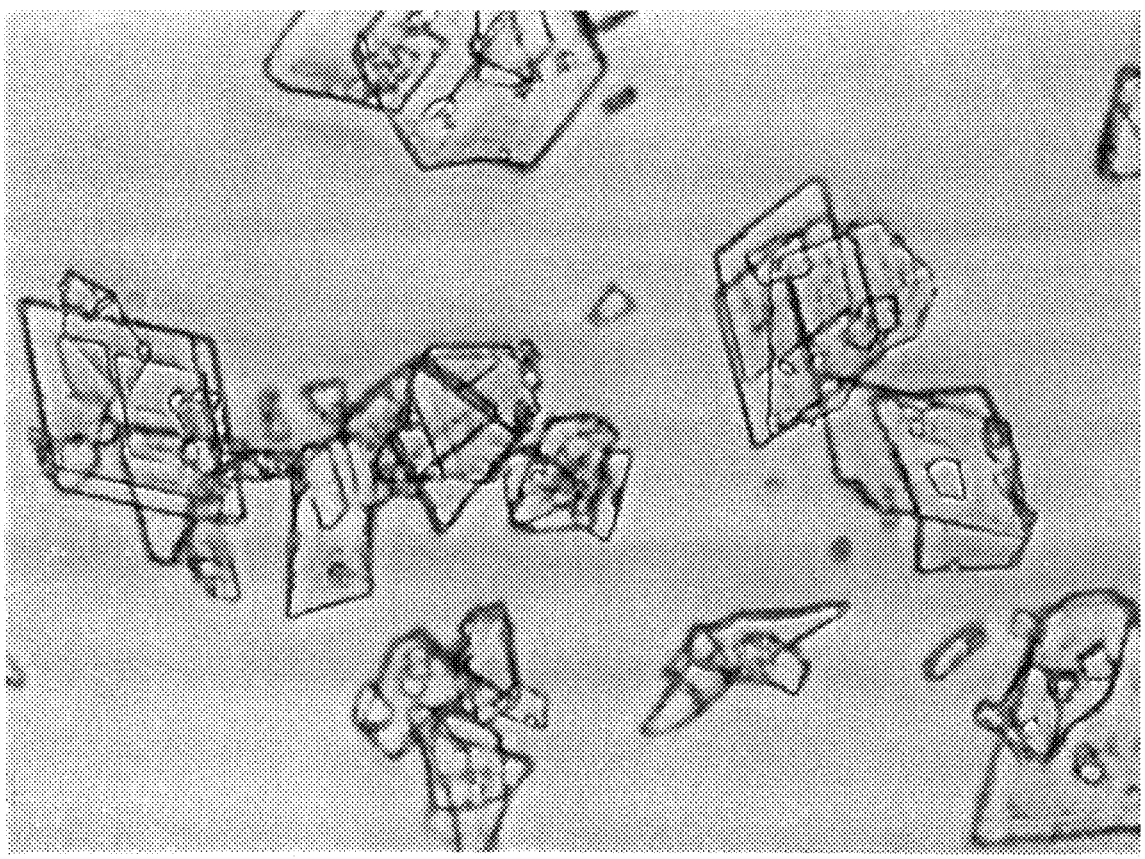
FIG. 5 depicts lipase crystals formulated with polyethylene oxide at initial time 0.
Figure 6:
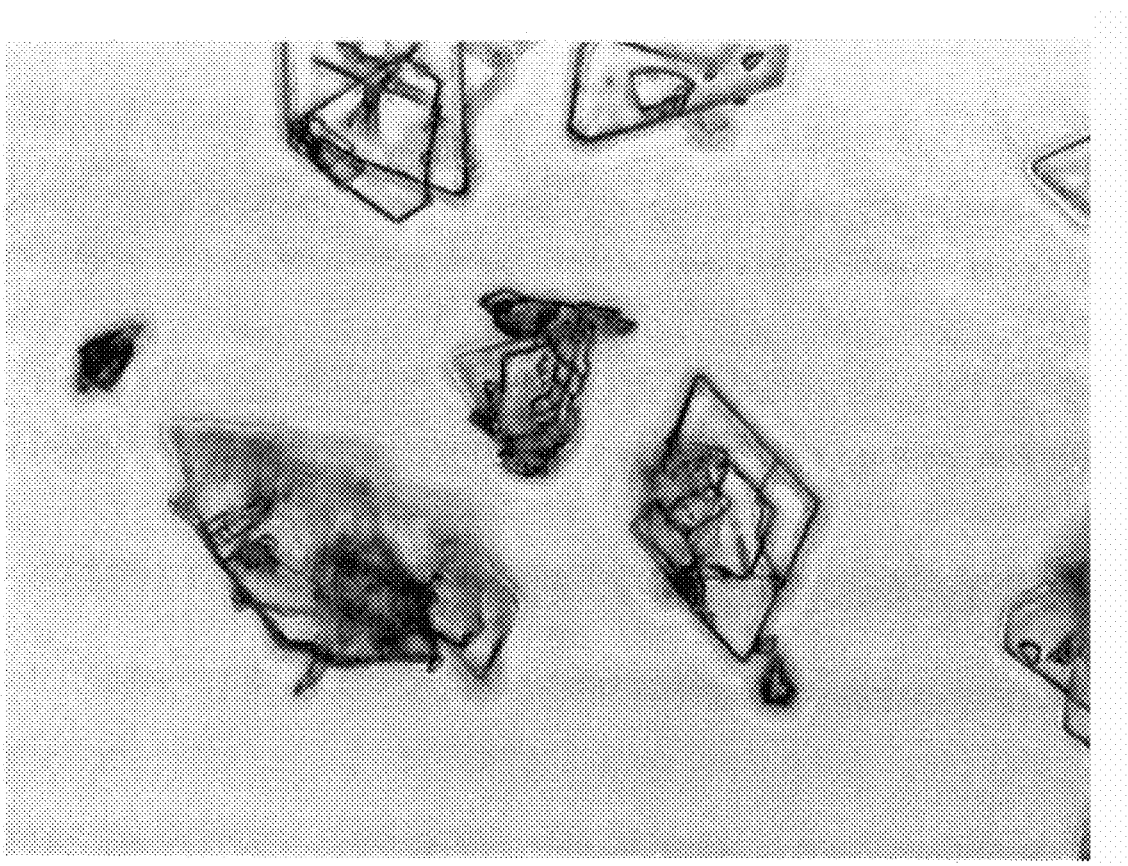
FIG. 6 depicts lipase crystals formulated with polyethylene oxide after incubation for 129 days at 40° C. and 75% humidity.

In this analysis, the crystals originally formulated with sucrose, trehalose, PEO and MOPEG were readily visualized after 129 days at 40° C. and 75% humidity. FIG. 5 shows that crystals formulated with PEO were present at the initial time. A similar microscopic observation taken 129 days later and shown in FIG. 6 demonstrates that crystallinity was maintained for the entire time period. Similar data was obtained for crystals formulated with sucrose, MOPEG and trehalose (data not shown).

Secondary Structure Characterization by FTIR:

The fourier transform infrared ("FTIR") spectra were collected on a Nicolet model 550 Magna series spectrometer as described by Dong et al. [Dong, A., Caughey, B., Caughey, W. S., Bhat, K. S. and Coe, J. E. *Biochemistry,* 1992; 31:9364–9370; Dong, A. Prestrelski, S. J., Allison, S. D. and Carpenter, J. F. *J.Pharm. Sci.,* 1995; 84: 415–424.] For the solid samples, 1 to 2 mg of the protein was lightly ground with 350 mg of KBr powder and filled into small cups used for diffuse reflectance accessory. The spectra were collected and then processed using Grams 32 from Galactic software for the determination of relative areas of the individual components of secondary structure using second derivative and curve-fitting program under amide I region (1600–1700 cm$^{-1}$).

For comparison, a soluble lipase sample was prepared by dissolving lipase crystals in phosphate buffered saline and analyzed for stability by FTIR.

Secondary structure was determined as follows: FTIR spectra were collected on a Nicolet model 550 Magna series spectrometer. A 1 ml sample of soluble lipase was placed on a Zinc selenide crystal of ARK ESP. The spectra were collected at initial (0) time and after the loss of most of the activity or, near-zero activity. The acquired data was then processed using Grams 32 software from Galactic Software for the determination of relative areas of the individual components of secondary structure using second derivative and curve-fitting program under amide I region (1600–1700 cmt$^{-1}$).

TABLE 4

Lipase at 40° C. and 75% Humidity

| Sample | α-Helix | β-Sheets | β-Turn | Extended coil | Random |
|---|---|---|---|---|---|
| Soluble Lipase initial time | 25.08 | 59.89 | 4.57 | 3.21 | 7.25 |
| After 3 days at 40° C. | 13.14 | 16.11 | 13.59 | 6.74 | 50.42 |
| Lipase - Sucrose initial time | 19.46 | 49.94 | 0.00 | 30.60 | 0.00 |
| After 66 days at 40° C. and 75% Humidity | 17.70 | 60.70 | 0.00 | 21.60 | 0.00 |
| Lipase - Trehalose initial time | 23.30 | 52.33 | 0.00 | 23.17 | 1.20 |
| After 66 days at 40° C. and 75% Humidity | 18.38 | 55.51 | 0.00 | 26.11 | 0.00 |
| Lipase-PEO initial time | 23.22 | 48.33 | 0.00 | 24.53 | 3.92 |
| After 66 days at 40° C. and 75% Humidity | 21.79 | 54.90 | 1.65 | 21.66 | 0.00 |
| Lipase - MOPEG initial time | 24.66 | 49.37 | 0.00 | 19.20 | 6.77 |
| After 66 days at 40° C. and 75% Humidity | 26.59 | 51.09 | 0.00 | 22.32 | 0.00 |

Conclusion:

Table 4 shows that for soluble lipase, approximately 50% and 75% of the α-helix and β-sheet structure content was lost over three days. There was a corresponding increase in the content of random structure.

In contrast, Table 4 shows that crystals which were formulated and dried were much more stable than the soluble enzyme. Such crystals showed a loss of a-helical structure which ranged from 6.1% to 21.1% after 66 days at 40° C. and 75% humidity. At the same time, random coil in solution increased from 7–50% over 3 days, while crystallinity showed minimum random coil content even after 66 days.

The data in Table 4, obtained using FTIR to monitor changes in secondary structure, correlated with the activity data shown in FIG. 4. In particular, lipase formulated with sucrose, PEO and MOPEG showed significantly less loss of α-helical structure and maintained a higher specific activity over the 66 day time period at elevated temperature and humidity than crystals formulated with trehalose, which showed a 21% loss of α-helical structure and had the lowest activity profile.

Example 10

Human Serum Albumin

Crystallization of Human Serum Albumin

Ten grams of powdered human serum albumin was added to a 75 ml stirred solution of 100 mM phosphate buffer (pH 5.5) at 4° C. Final protein concentration was 120 mg/ml, estimated from the OD$_{280}$ value of the solution. First, a saturated ammonium sulfate solution (767 g/l), prepared in deionized water, was added to the protein solution to a final concentration of 350 g/l or 50% saturation. Next, the crystallization solution was "seeded" with 1 ml of 50 mg/ml albumin crystals in 50% ammonium sulfate at pH 5.5. Seed crystals were prepared by washing a sample of crystals free of precipitate with a solution of 50% saturated ammonium sulfate in 100 mM phosphate buffer at pH 5.5. The seeded crystallization solution was incubated overnight at 4° C. on a vigorously rotating platform. Crystals in the shape of rods (20 μm) appeared in the solution overnight after approximately 16 hr.

Example 11

Formulation of HSA Crystals Using Gelatin as Excipient:

In order to enhance the stability of human serum albumin (HSA) crystals during drying and storage the crystals were formulated with excipients. In this example, HSA crystals were formulated in the slurry form in the presence of mother liquor before drying. Gelatin (Sigma Chemical Co., St. Louis, Mo.) was added to lipase crystals in mother liquor as an excipient. Sufficient gelatin was added to lipase crystals at a protein concentration 20 mgs/ml in mother liquor (2.5M ammonium sulfate in 100 mM phosphate buffer, pH 5.5) to reach a final concentration of 10%. The resulting suspension was tumbled at room temperature for 3 hr. After treatment with gelatin, the crystals were separated from the liquid by centrifugation as described in Example 6, method 1.

Drying of HSA Crystals

The HSA crystals were then dried by the four methods described in Example 6. The crystals were suspended in cold (4° C.) ethanol as the organic solvent of method 4.

Example 12

Soluble Human Serum Albumin Preparation:

For comparison, the soluble HSA sample was prepared by dissolving HSA crystals at 20 mg/ml in water.

Example 13

Shelf Stability:

Shelf stability of HSA dried crystal formulations were carried out in a waterbath at 50° C. temperature. The stability of the crystals was monitored by following structural degradation by FTIR analysis.

Moisture Content:

Moisture content was determined by the Karl Fischer method according to manufacturer's instructions using a Mitsubishi CA-06 Moisture Meter equipped with a VA-06 Vaporizer (Mitsubishi Chemical Corporation, Tokyo, Japan).

TABLE 5

Moisture content HSA crystals

| TIME, DAYS | % Moisture Gelatin |
|---|---|
| 0 | 5.0464 |
| 12 | 6.3841 |

Figure 7:
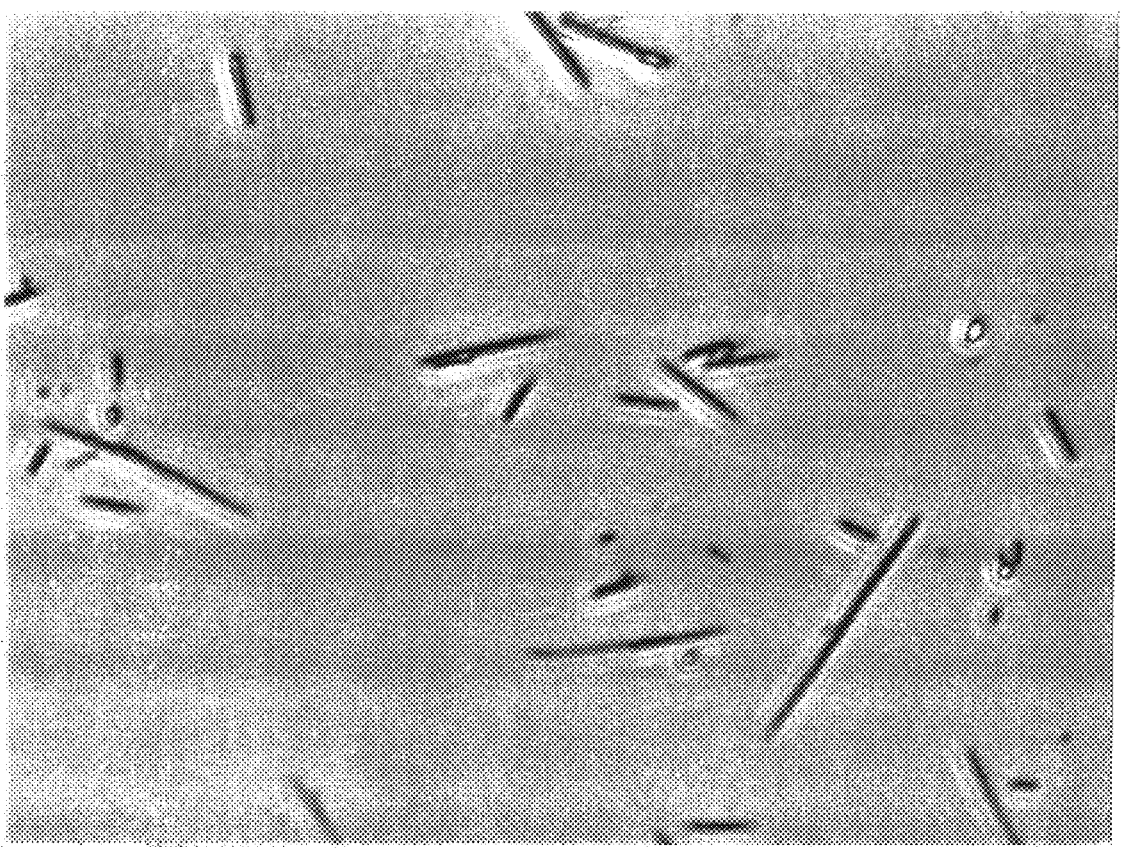
FIG. 7 depicts human serum albumin crystals formulated with gelatin at initial time 0.
Figure 8:
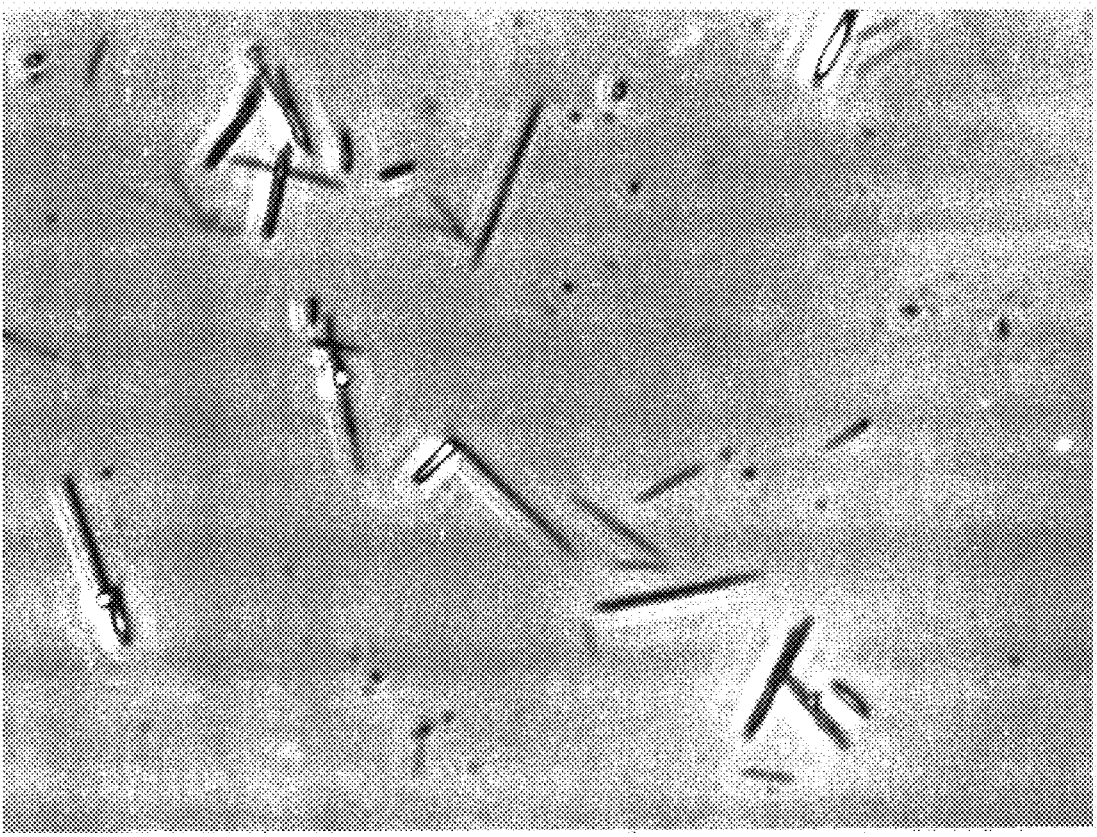
FIG. 8 depicts human serum albumin crystals formulated with gelatin after incubation for 4 days at 50° C.

Crystallinity:

The crystal integrity of the formulations was measured by quantitative microscopic observations, as described in Example 9. FIG. 7 shows that HSA crystals were readily visualized immediately after preparing the formulation with gelatin. FIG. 8 shows that crystallinity was maintained after four days at 50° C.

Secondary Structure Characterization by FTIR:

The FTIR spectra were collected on a Nicolet model 550 Magna series spectrometer as described by Dong et al. [Dong, A., Caughey, B., Caughey, W. S., Bhat, K. S. and Coe, J. E. *Biochemistry*, 1992; 31:9364–9370; Dong, A. Prestrelski, S. J., Allison, S. D. and Carpenter, J. F. *J.Pharm. Sci.*, 1995; 84: 415–424]. For the solid samples, 1 to 2 mg of the protein was lightly ground with 350 mg of KBr powder and filled into small cups used for diffuse reflectance accessory. The spectra were collected and processed using Grams 32 from Galactic software for the determination of relative areas of the individual components of secondary structure using a second derivative and curve-fitting program under amide I region (1600–1700 cm$^{-1}$).

For comparison, the soluble HSA sample was prepared by dissolving HSA crystals in water and tested for stability by FTIR. The secondary structure was determined as in Example 9.

TABLE 6

Secondary Structure content of HSA

| Sample | α-Helix | β-Sheets | β-Turn | Extended coil | Random |
|---|---|---|---|---|---|
| HSA-Soluble | 45.47 | 6.83 | 6.79 | 40.91 | 0.00 |
| HSA-Sol. 15 min | 28.71 | 30.39 | 8.59 | 28.07 | 4.24 |
| HSA-Sol. 30 min | 19.15 | 34.69 | 8.16 | 27.91 | 10.09 |
| HSA-Sol. 60 min | 10.04 | 15.82 | 0.00 | 42.83 | 31.31 |
| HSA crystals | | | | | |
| HSA Gelatin | 49.08 | 24.77 | 0.00 | 26.15 | 0.00 |
| HSA Gelatin After 12 days at 50° C. | 40.93 | 7.65 | 7.48 | 43.94 | 0.00 |

Conclusion:

Soluble HSA showed a rapid 78% decrease in α-helical content after 1 hour in solution and a corresponding increase in random coil structure.

Dry formulated crystals showed an approximately 16% decrease in α-helical content, a large decrease in β-sheet content and no increase in the content of random structure.

Example 14

Penicillin Acylase

Crystallization of Penicillin Acylase

An ammonium sulfate suspension of Penicillin acylase from Boehringer Mannheim was the raw material. The suspension of Penicillin acylase was diluted 1:3 with deionized water. This solution was concentrated by diafiltration using a 30K membrane to a final concentration of 200 OD at $A_{280nm}$/ml. The enzyme solution was then diluted with 4 M $NaH_2PO_4.H_2O$ to 150 OD $A_{280nm}$/ml.

A biphasic solution of 4 M and 1 M sufficient $NaH_2PO_4.H_2O$ to yield a final solution concentration of 1.9 M $NaPO_4$, was prepared. In this case, 280 ml of 1 M $NaH_2PO_4.H_2O$ was carefully overlaid on top of to the top of 549 ml of 4 M $NaH_2PO_4.H_2O$. The enzyme solution was poured gently into the side of the container to form a layer above the 1 M layer. An overhead stirrer was set up with a marine impeller. The agitator was placed into the container with the blades just below the 4M/1M interface. The speed was adjusted to a setting of 8.0, or 600 rpm. The agitator was switched on and stopped after 10 minutes. The impeller was removed from the container. The volume of seed crystals was measured with a graduated pipette using between 0.5 and 0.1% by volume and added to the 20 L sterile polycarbonate container. The seed was not allowed to be static for more than 10 seconds before addition. The solution was mixed by hand using a flat-blade impeller for about 1 minute. The crystallization mixture was allowed to stand for 24 hours.

After 24 hours, the container was opened and the solution was mixed by hand for 30 seconds. The solution was allowed to sit for an additional 24 hours. After a total of 48 hours, a 10 ml sample was taken of the supernatant. The sample was filtered with a 0.2 micron Acrodisc. The $A_{280nm}$ of the supernatant was measured. When supernatant $A_{280nm}$ was greater than 1.0 mg/ml, the crystallization was allowed to continue for 24 more hours. When the supernatant concentration was less than 1.0 mg/ml, the $A_{280nm}$ Of crystal slurry and supernatant directly were determined.

Example 15

Penicillin G Assay for PA Crystals

The basis of the activity assay for Penicillin acylase involves a titrimetric assay which measures the enzymatic hydrolysis of benzyl penicillin by the enzyme. The enzyme catalyzes cleavage of a phenyl acetyl group from penicillin G thus causing a decrease in pH. This activity was followed by measuring the volume of 50 mM NaOH needed (to maintain a pH of 8 at 28° C.) per minute of reaction. The assay uses a substrate buffer made with potassium chloride and Tris and was reported in U/mg.

Penicillin Acylase Assay:

Chemicals and Solutions Used in the Assay:

1. Penicillin-G, Sigma, Potassium salt
2. 0.05 N Sodium hydroxide
3. 1.0 M KCl, 20 mM Tris buffer, pH 8.0
4. 10 mM Tris, 10 mM $CaCl_2$ buffer, pH 8.0
5. 0.01 M PBS buffer, pH 7.5

Preparation of Substrate Solution 1 g of penicillin-G was added to 10 ml of 1.0 M KCl, 20 mM Tris buffer, pH 8.0 solution and about 70 ml of DI water, 1 ml of 10 mM Tris, 10 mM $CaCl_2$. Then the pH of the solution was adjusted to 8.0 using 0.05 N NaOH. Next, final solution volume was adjusted to 100 ml. The solution was prepared fresh before each use and used within five hours of preparation.

Preparation of PA Sample Solution

A sample of Penicillin acylase was dissolved in PBS buffer, pH 7.4. Typically, 2 to 4 mg (dry weight) of protein were used for each assay.

Assay for Hydrolysis of Penicillin G 20 ml of penicillin acylase substrate solution was added to a titration vessel and equilibrated to 28° C. After adding the enzyme solution to the reaction vessel, the hydrolysis of penicillin-G was monitored by titrating the reaction mixture with 0.05 N NaOH to maintain the pH at 8.0.

Example 16

Formulation of PA Crystals Using Hydroxypropyl-β-cyclodextrin (HPCD) as Excipient:

In order to enhance the stability of PA crystals during drying and storage, the crystals were formulated with excipients. In this example, PA crystals were formulated in the slurry form in the presence of mother liquor before drying. Hydroxypropyl-β-cyclodextrin (HPCD) (Sigma Chemical Co., St. Louis, Mo.) was added to PA crystals in mother liquor as an excipient. Sufficient HPCD was added to lipase crystals at a protein concentration 20 mgs/m in mother liquor (1.9M $NaH_2PO_4$, pH 6.6), to reach a final concentration of 10%. The resulting suspension was tumbled at room temperature for 3 hr. After treatment with HPCD, the crystals were separated from the liquid by centrifugation as described in Example 6, method 1.

Example 17

Formulation of PA Crystals Using Mother Liquor Itself as Excipient:

The PA crystals were formulated using mother liquor (1.9M $NaH_2PO_4$, pH 6.6). The crystals were separated by centrifugation as in Example 16.

Example 18

Drying PA

The PA crystals from Examples 15–17 were then dried according to the methods 1, 3 or 4 of Example 6. The organic solvent used for method 4 of Example 6 was ethyl acetate.

Example 19

Soluble PA Preparation:

As a standard of comparison, a sample of soluble PA was prepared by dissolving PA crystals in water at 20 mg/ml.

Figure 9:
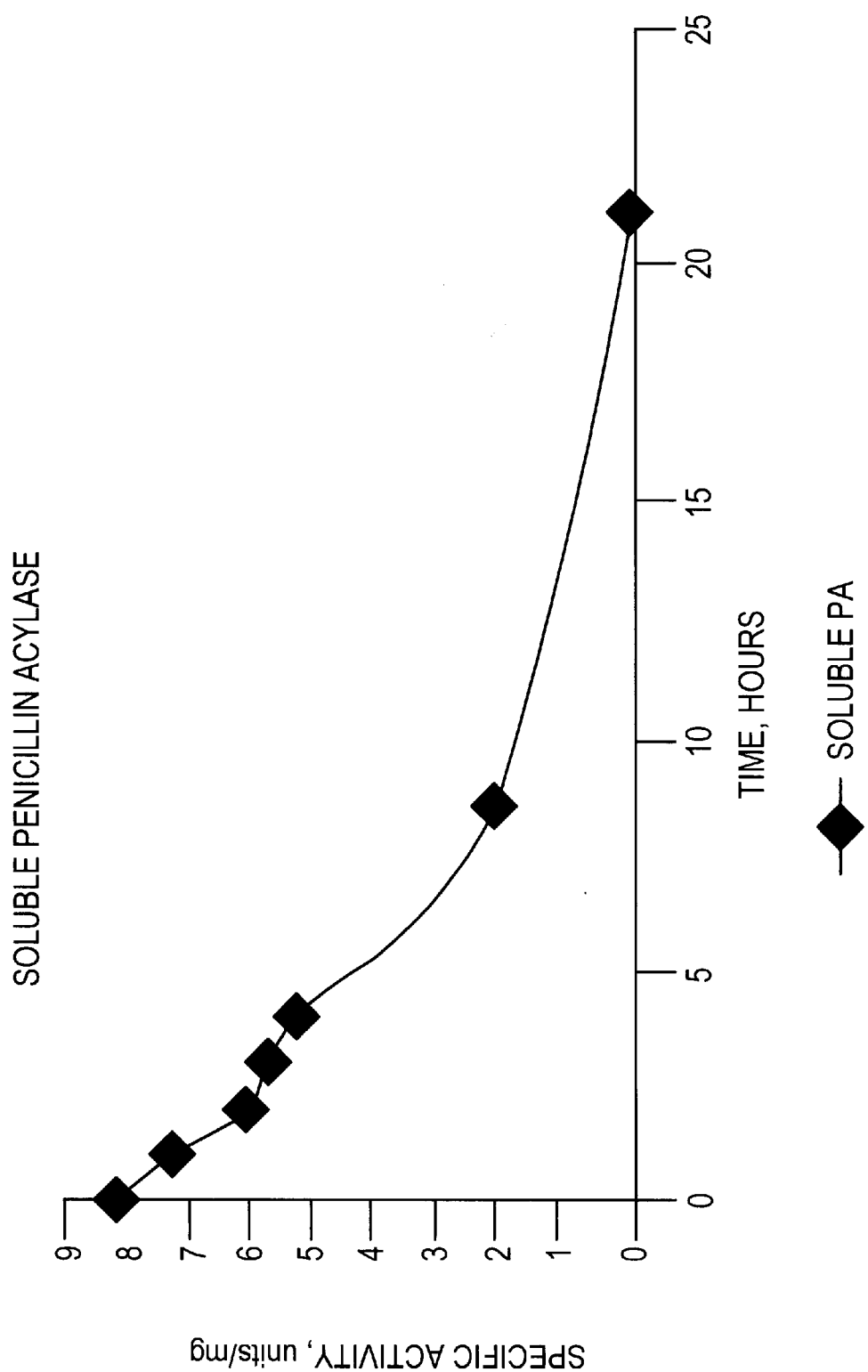
FIG. 9 depicts the specific activity of soluble Penicillin acylase over time at 55° C.

The stability of soluble PA was measured over time and a plot specific activity at 55° C. versus time is shown in FIG. 9. PA enzyme activity in solution decayed rapidly and was undetectable after approximately 20 hours.

Example 20

Figure 10:
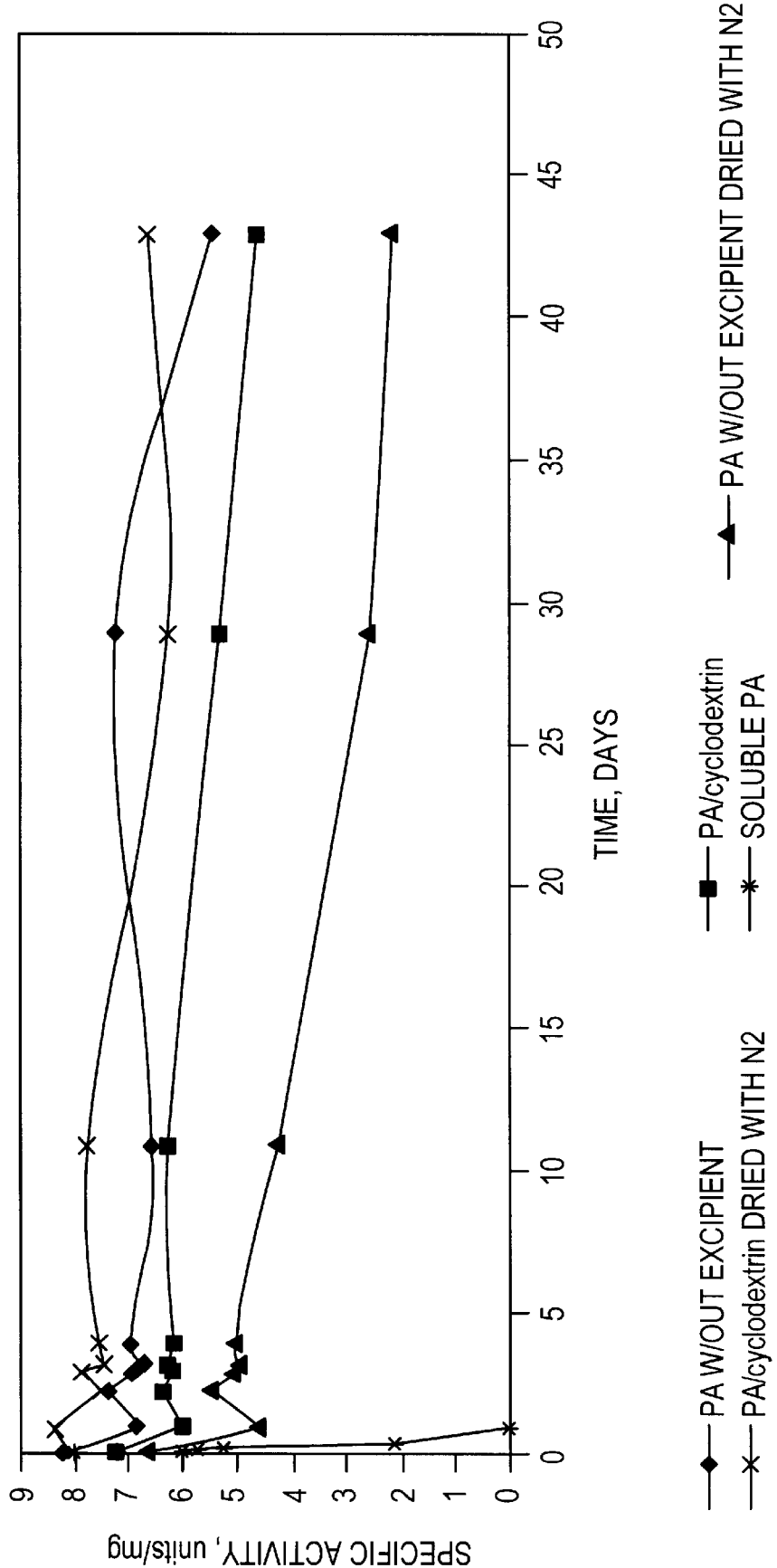
FIG. 10 depicts the shelf stabilities of various dried Penicillin acylase crystal formulations at 55° C.

Activity of the Dried Crystals:

The activity of the dried crystals from Example 18 was tested in the Pen G assay as described in Example 15. The dried crystals (5 mg) were dissolved in 1 ml of water and the activity was measured using Pen G as substrate Shelf Stability:

The shelf stability of PA dried crystal formulations was determined using a Reactive-Therm III—Heating/Stirring module by Pierce at 55° C. temperature. Activities were measured by dissolving 5 mg of the dried sample in water and measuring the enzyme activity in the Pen G assay described in Example 15 and compared with the initial results. FIG. 10 depicts the shelf stability profiles of PA crystals with and without excipient. FIG. 10 also depicts shelf stability profiles of PA crystal formulations dried with nitrogen (method 1) or air dried (method 4).

TABLE 7

| Penicillin acylase activity at 55° C. | |
|---|---|
| Dry Crystals-Penicillin acylase | T½days |
| Penicillin acylase - crystals dried by lyophilization | 123.25 |
| Penicillin acylase - HPCD dried by lyophilization | 99.24 |
| Penicillin acylase - dried using nitrogen | 24.85 |

TABLE 7-continued

Penicillin acylase activity at 55° C.

| Dry Crystals-Penicillin acylase | T½days |
|---|---|
| Penicillin acylase - HPCD dried by nitrogen | 87.91 |
| Soluble Penicillin acylase | 0.21 (4.92 hrs) |

The $T_{1/2}$ was calculated from the shelf life data by non-linear regression analysis using the Sigma Plot program. The stability of the formulated crystals relative to the non-formulated crystals was enhanced, as shown in Table 7. For example, crystals formulated with HPCD were 418 fold more stable soluble PA at 55° C. (Table 7). Crystals formulated with HPCD were 3.5 fold more stable at 55° C. than non-formulated PA crystals made without an excipient, as shown in Table 7.

Moisture Content:

Moisture content was determined by the Karl Fischer method according to manufacturer's instructions using a Mitsubishi CA-06 Moisture Meter equipped with a VA-06 Vaporizer (Mitsubishi Chemical Corporation, Tokyo, Japan).

TABLE 8

Moisture content of PA crystals

| | % Moisture | |
|---|---|---|
| DAYS | PA | HPCD |
| 0 | 2.6198 | 1.5722 |
| 43 | 2.1792 | 3.1963 |

Crystallinity:

The crystal integrity of the formulations was measured by quantitative microscopic observations as described in Example 9. Crystallinity was maintained through out the process as indicated by the crystals, which were readily visible (data not shown).

Secondary Structure Characterization by FTIR:

Stability was assessed by quantifying the secondary stucture content of the dried and formulated PA crystals by FTIR as described in Example 9. Soluble PA was used for comparative purposes.

TABLE 9

Secondary Structure of PA at 55° C.

| Sample | α-Helix | β-Sheets | β-Turn | Extended coil | Random |
|---|---|---|---|---|---|
| Soluble PA Init. time | 37.74 | 33.53 | 11.57 | 17.16 | 0.00 |
| After 2 hrs at 55° C. | 25.27 | 35.32 | 7.29 | 21.93 | 10.19 |
| After 24 hrs at 55° C. | 9.29 | 50.66 | 0.00 | 26.77 | 13.28 |
| PA - dried by lyoph. init. time | 33.83 | 27.99 | 5.32 | 13.66 | 0.00 |
| After 43 days at 55° C. | 22.53 | 18.9 | 17.03 | 18.42 | 23.12 |
| PA - HPCD dried by lyoph. init. time | 35.9 | 36.96 | 0.00 | 27.14 | 0.00 |
| After 43 days at 55° C. | 19.05 | 16.77 | 23.11 | 16.65 | 24.42 |
| PA - dried by N2 init. time no excipient | 25.73 | 34.93 | 6.68 | 28.73 | 3.93 |
| After 43 days at 55° C. | 11.88 | 34.73 | 10.22 | 30.07 | 13.10 |
| PA - HPCD dried by nitrogen init. time | 31.26 | 35.78 | 12.24 | 20.72 | 0.00 |
| After 43 days at 55° C. | 22.17 | 25.31 | 0.00 | 42.23 | 10.29 |

Conclusion:

The loss of α-helical content was 76% after 1 day for soluble Penicillin acylase. In contrast, when HPCD was used as an excipient and the formulation was dried by method 1 of Example 6, only 31% of the α-helical content was lost after 43 days at 55° C. temperature.

Example 21

Glucose Oxidase

Preparation of Glucose Oxidase Crystals

We prepared crystals of glucose oxidase as follows. First, the glycoprotein was purified by anion exchange chromatography and then the crystallization parameters were optimized (data not shown).

As a result of these studies, we found that the conditions for crystallization of glucose oxidase fall generally in the range of 7 to 17% PEG 4000 or 6000, 8 to 20% 2-propanol or ethanol and buffer to adjust the pH to between 3 and 6. It should be understood, however, that many sets of experimental conditions within and near this range can produce satisfactory results for the crystallization of glucose oxidase and other glycoproteins. Those of skill in the art will appreciate that the precise conditions which efficiently produce crystals of the desired size and quality, will vary due to differences in experimental conditions, such as protein and reagent purity, rates of stirring, shear force effects and carbohydrate content.

Large Scale Crystallization of Glucose Oxidase

We determined preferred conditions for preparative scale crystallization of glucose oxidase. Preparative scale crystallization generally involves 100 to 900 mls of glycoprotein.

A. Crystallization at Constant pH Without Seed

Glucose oxidase was diafiltered in water and concentrated to an $A_{280}$ of between 5 and 15. The glucose oxidase concentrate was mixed (1:1) with one volume of the crystallizing reagent containing 18% PEG 6000, 32% 2-propanol in 0.2 M Na-Acetate at pH 5.0. After mixing, the solution was cooled to 6° C. The glucose oxidase crystallization solution was stirred for 24 hours at 100 rpm with a propeller stirrer. During this time, the crystals formed gradually.

Example 22

Formulation of Glucose Oxidase Crystals Using Trehalose as Excipient:

In order to enhance the stability of glucose oxidase (GOD) crystals during drying and storage, the crystals were formulated with excipients. In this example, GOD crystals were formulated in the slurry form in the presence of mother liquor before drying. Trehalose (Sigma Chemical Co., St. Louis, Mo.) was added to GOD crystals in mother liquor as an excipient. Sufficient trehalose was added to GOD crystals at a protein concentration 20 mgs/ml in mother liquor (100 mM sodium acetate buffer, pH 5.5 containing 32% isopropanol and 9% PEG 6000) to reach a final concentration of 10%. The resulting suspension was tumbled at room temperature for 3 hr. After treatment with trehalose, the crystals were separated from the liquid by centrifugation as described in Example 6, method 1.

Example 23

Formulation of Glucose Oxidase Crystals Using Lactitol as Excipient:

Glucose oxidase crystals were formulated as in Example 22 by adding lactitol (Sigma Chemical Co. St. Louis, Mo.), (instead of trehalose) to a final concentration of 10% to the mother liquor. The crystals were separated from the mother liquor/lactitol solution after three hours by centrifugation.

Example 24

Formulation of Glucose Oxidase Crystals Using Hydroxypropyl-β-cyclodextrin (HPCD) as Excipient:

Glucose oxidase crystals were formulated using hydroxypropyl-β-cyclodextrin (HPCD) as in Example 22 (instead of trehalose) by adding HPCD to a final concentration of 10% in mother liquor and incubated for 3 hrs (Sigma Chemical Co. St. Louis, Mo.). The crystals were then separated from the mother liquor/HPCD solution after 3 hr. by centrifugation as described in Example 6, method 1.

Example 25

Formulation of Glucose Oxidase Crystals Using Gelatin as Excipient:

Glucose oxidase crystals were formulated as in Example 22 by adding gelatin to a final concentration of 10% (Sigma Chemical Co. St. Louis, Mo.) in mother liquor (instead of trehalose). The crystals were separated from the mother liquor/gelatin solution after three hours by centrifugation.

Example 26

Formulation of Glucose Oxidase Crystals Using Methoxypolyethylene Glycol as Excipient:

The glucose oxidase crystals were formulated as in Example 22 by adding methoxypoly ethylene glycol to a final concentration of 10% (Sigma Chemical Co. St. Louis, Mo.) in mother liquor. The crystals were separated from the mother liquor/methoxypoly ethylene glycol solution after 3 hrs by centrifugation as described in Example 6, method 1.

Example 27

Formulation of Glucose Oxidase Crystals Using Sucrose as Excipient:

Glucose oxidase crystals were formulated as in Example 22 by adding sucrose to a final concentration of 10% (Sigma Chemical Co., St. Louis, Mo.) in the mother liquor. The crystals were separated from the mother liquor/sucrose solution after three hours by centrifugation.

Example 28

Drying Glucose Oxidase Formulations

The glucose oxidase crystal formulations described above were dried according to the methods described in Example 6. Method 4 utilized cold (4° C.) isopropanol as the organic solvent.

Example 29

Soluble Glucose Oxidase Preparation:

For comparison, the soluble glucose oxidase sample was prepared by dissolving glucose oxidase crystals at 20 mg/ml in 50 mM citrate buffer, pH 6.0.

Figure 11:
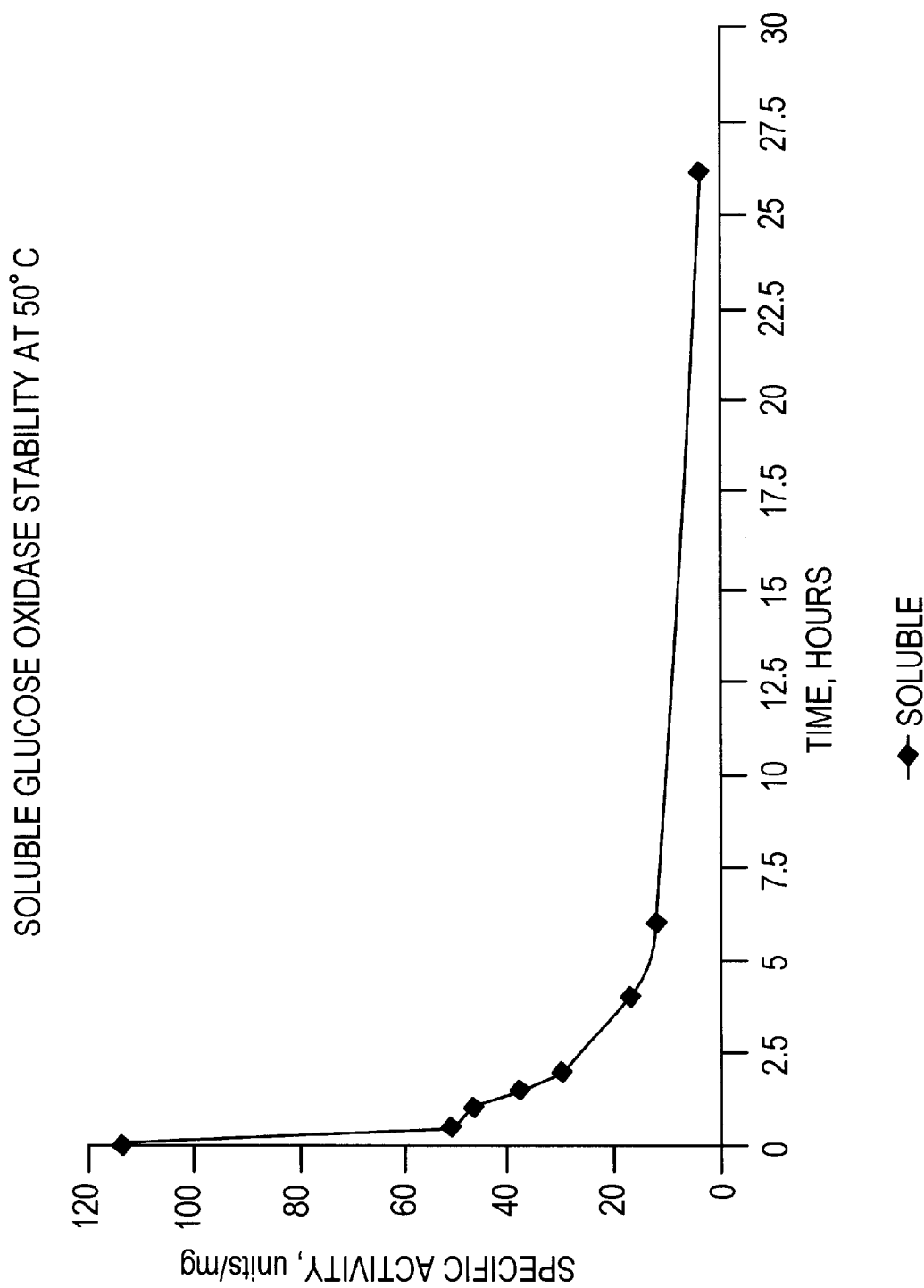
FIG. 11 depicts the specific activity of soluble glucose oxidase over time.

FIG. 11 shows the stability of the soluble glucose oxidase over time at 50° C. The specific activity declines rapidly with time. After 24 hours, the specific activity decreases by more than 90%. The $T_{1/2}$ for soluble glucose oxidase was calculated to be 0.91 hours.

Example 30

Glucose Oxidase Activity Assay:

The following protocol was used to determine the activity of dried glucose oxidase crystals and crystal formulations.

Chemicals and solutions:

1. Phosphate buffer (20 mM, pH 7.3), NaCl (0.1 M) solution,
2. 21 mM O-Dianisidine dihydrochloride stock solution, diluted to 0.21 mM as working solution before use,
3. 2 M glucose solution,
4. Peroxide solution (2 mg/ml),
5. 50 mM citrate buffer, pH 6.0

Sample Preparation:

1. Add 2 mg of glucose oxidase to 1 ml of 50 mM citrate buffer, pH 6.0 and vortexed well for about 2 min. The solution was mixed by tumbling at room temperature for 1 hour to reconstitute.
2. Prepare a dilute enzyme solution by mixing 0.1 ml of the above enzyme solution with 4.9 ml of the same citrate buffer.

Assay Procedure for Enzyme Activity Measurement:

1. The assay was monitored by a UV-Vis spectrophotometer. Use the kinetic mode and set wavelength at 460 nm and temperature at 25° C.
2. Warm up the 0-dianisidine/phosphate working solution in the 25° C. water bath and bubble the solution with oxygen for at least 20 min. before use.
3. Measure the blank using the reagent solution without the enzyme solution added.
4. Pipette 2.4 ml of oxygenated O-dianisidine/phosphate working solution, 0.4 ml of 2 M glucose solution and 0.1 ml of peroxidase into a disposable cuvette.
5. Add 10 ml of the enzyme sample on the cuvette wall (tilt the cuvette to prevent the sample from mixing with the reagent at this step) and cover with a piece of parafilm. Mix quickly by inverting the cuvette twice, insert the cuvette into the spectrophotometer's cell compartment and start to collect data.

Calculate the enzyme specific activity using the following formula

Specific activity=$A*B*C/D*E*F$

Where:
A=The changed in units of absorbance at 460 nm per minute
B=Reaction mixture volume (ml)
C=Dilution factor
D=11.3 (a constant)
E=Weight (mg) of the enzyme used
F=Sample volume (ml)

Example 31

Activity of the Dried Crystals:

The activity of the dried crystal formulations of glucose oxidase was measured as described in Example 30.

Shelf Stability:

A study of the shelf stability of formulations of glucose oxidase crystals was performed. In this case, the formulations were dried by method 4 of Example 6 and were stored in a 2 ml screw cap Eppendorf tube in a waterbath at 50° C. temperature for 13 days. Activities at specific time points were obtained by dissolving 2 mg of the dried sample in 50 mM citrate buffer, pH 6.0 and then measuring the activity according to Example 30.

Figure 12:
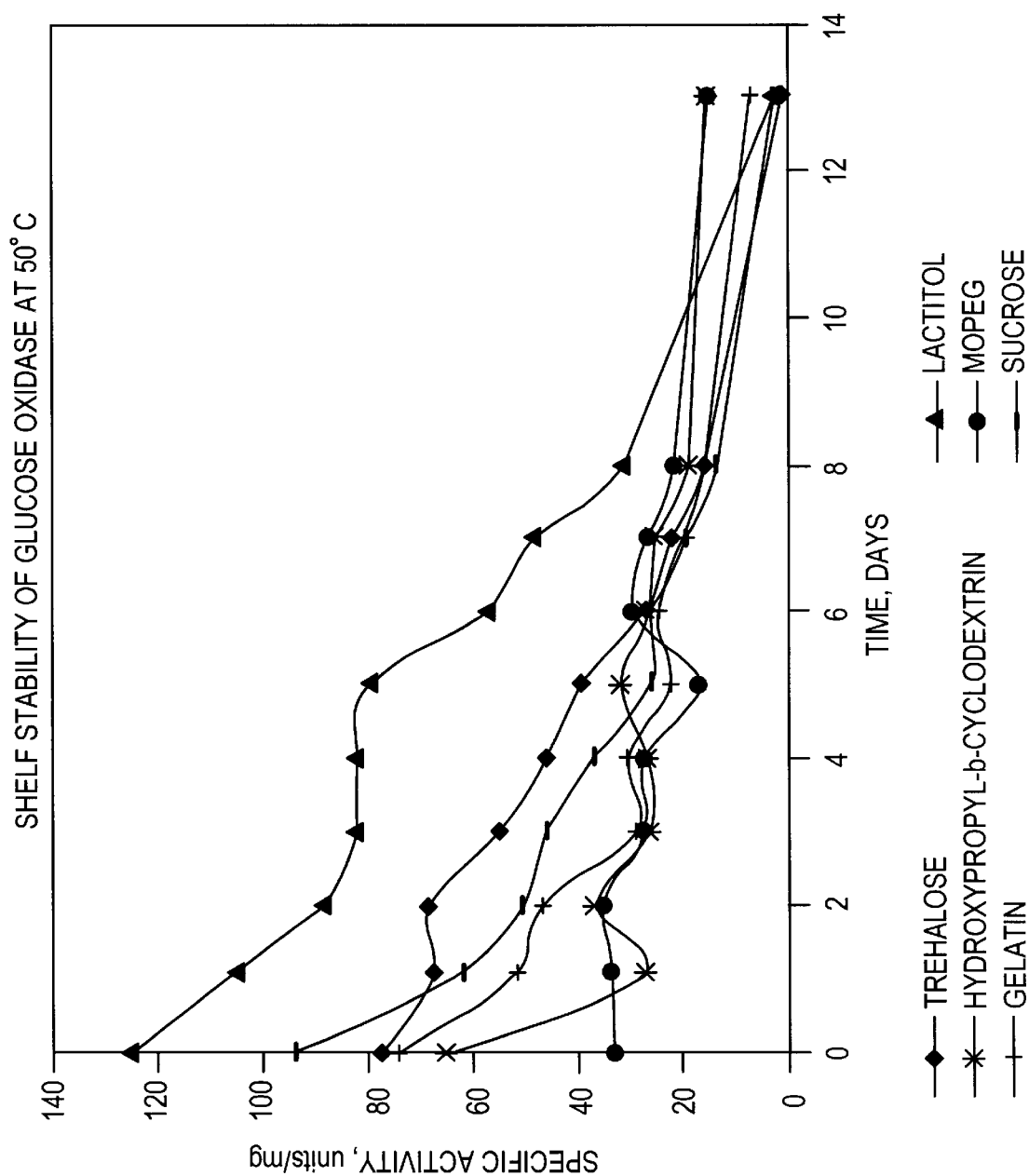
FIG. 12 depicts the shelf stabilities of various dried glucose oxidase crystal formulations at 50° C.

The shelf stabilities of the various glucose oxidase formulations stored at 50° C. were determined. The data are presented in FIG. 12. Lactitol was the most effective excipient at preserving glucose oxidase specific activity over time at elevated temperature.

TABLE 10

Glucose Oxidase at 50° C.
Dried glucose oxidase crystals

| Excipient | T½ days |
|---|---|
| none | 1.52 |
| Trehalose | 3.8 |
| Lactitol | 4.85 |
| HPCD | 2.4 |
| MOPEG | 13.1 |
| Gelatin | 3.95 |
| Sucrose | 3.27 |
| Soluble GOD | 0.04 (0.91 hrs) |

The $T_{1/2}$ was calculated from the shelf life data by non-linear regression analysis using the Sigma Plot program. Table 10 shows that formulations of glucose oxidase were 95 fold more stable than soluble when trehalose was used as the excipient. In addition, formulations of glucose oxidase were 121 fold more stable than soluble when lactitol was used as the excipient (Table 10). Formulations using HPCD or MOPEG as excipients with glucose oxidase crystals were 60 and 325 fold more stable than soluble glucose oxidase, respectively(Table 10). Finally, formulations using gelatin or sucrose as excipients with glucose oxidase crystals were 99 and 82 fold more stable than soluble, respectively (Table 10).

Formulations made with either trehalose, lactitol, HPCD, MOPEG, gelatin or sucrose, as excipients with glucose oxidase crystals were 2.5 fold, 3.2 fold, 1.6 fold, 8.6 fold, 2.6 fold, or 2.2 fold more stable than glucose oxidase crystals made without an excipient at 50° C., as measured by $T_{1/2}$, as shown in Table 10.

Moisture Content:

Moisture content was determined by the Karl Fischer method according to manufacturer's instructions using a Mitsubishi CA-06 Moisture Meter equipped with a VA-06 Vaporizer (Mitsubishi Chemical Corporation, Tokyo, Japan).

TABLE 11

Moisture content of GOD crystal formulations

| TIME | % Moisture | | | | | |
|---|---|---|---|---|---|---|
| DAYS | Trehalose | Lactitol | HPCD | MOPEG | Gelatin | Sucrose |
| 0 | 4.3819 | 4.5274 | 8.3817 | 4.2008 | 4.7090 | 4.2083 |
| 13 | 8.7292 | 11.4808 | 8.7582 | 8.0763 | 13.7541 | 9.8284 |

Crystallinity:

The crystal integrity of the GOD formulations was measured by quantitative microscopic observations as described in Example 9. In this example, the crystals were readily visualized, indicating that crystallinity was maintained throughout the process.

Figure 13:
FIG. 13 depicts glucose oxidase crystals formulated with lactitol at initial time 0.
Figure 14:
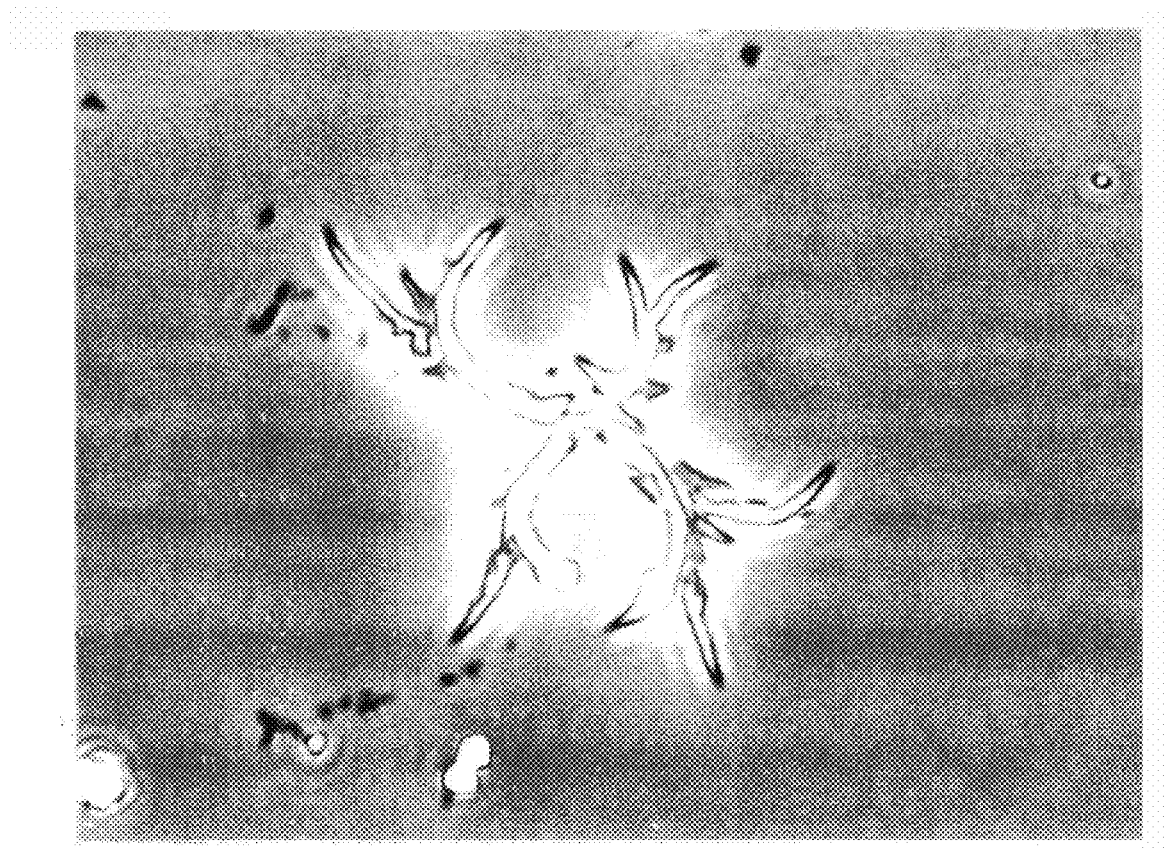
FIG. 14 depicts glucose oxidase crystals formulated with lactitol after incubation for 13 days at 50° C.
Figure 15:
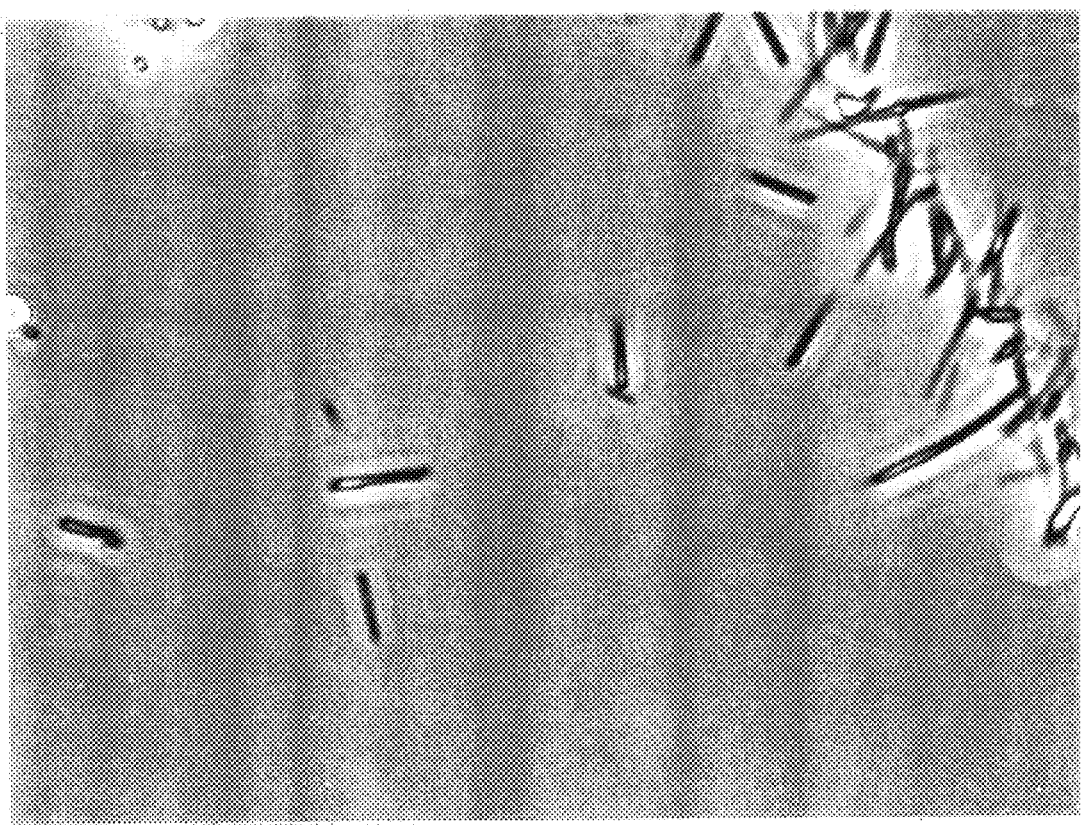
FIG. 15 depicts glucose oxidase crystals formulated with trehalose at initial time 0.
Figure 16:
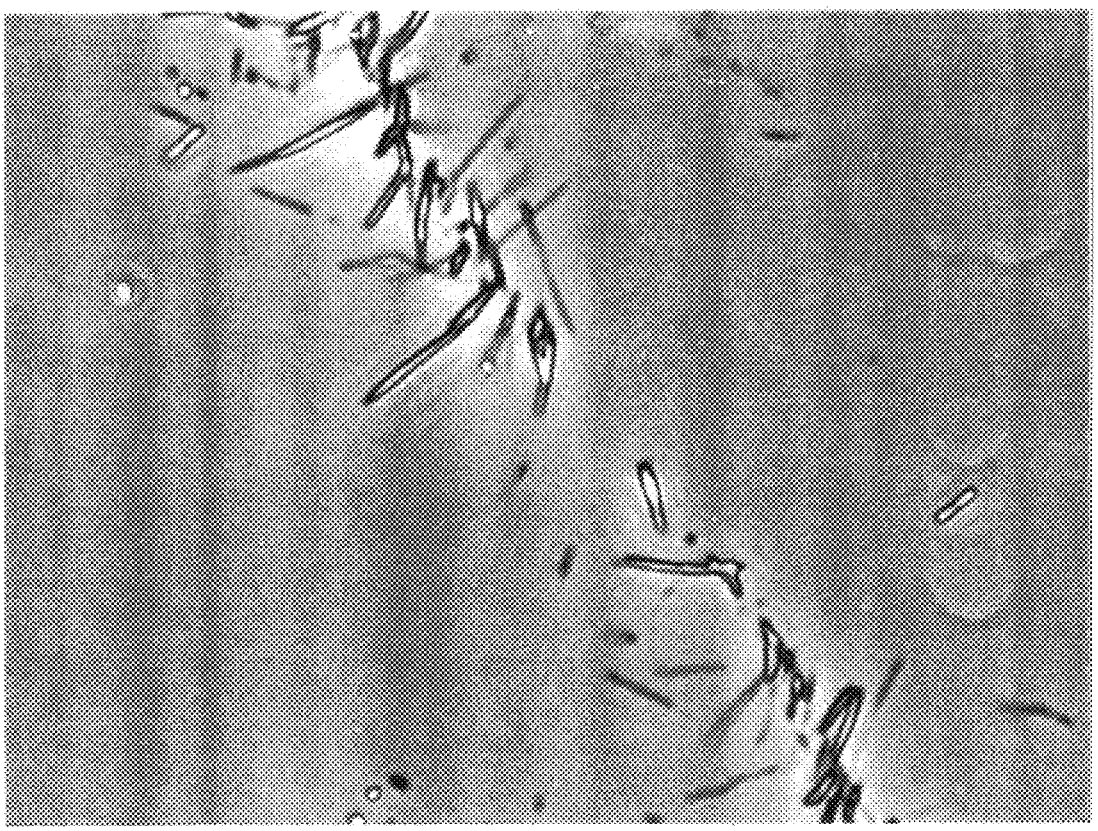
FIG. 16 depicts glucose oxidase crystals formulated with trehalose after incubation for 13 days at 50° C.

FIG. 13 show that glucose oxidase crystals were readily visualized immediately after preparing the lactitol formulation. FIG. 14 demonstrates that crystallinity was maintained after 13 days at 50° C. Crystalline material was also readily visualized after formulating glucose oxidase with trehalose, as depicted in FIG. 15. Likewise, crystalline material remained readily visualized after after 13 days at 50° C., as shown in FIG. 16.

Secondary Structure Characterization by FTIR:

Stability was assessed by quantifying the secondary stucture content of the dried and formulated GOD crystals by FTIR as described in Example 9. For comparison, a soluble glucose oxidase sample was prepared by dissolving glucose oxidase crystals in 50 mM citrate buffer at pH 6.0 and placing about 1 ml on a Zinc selenide crystal of ARK ESP, which then analyzed for stability by FTIR.

TABLE 12

Soluble Glucose Oxidase at 50° C.

| Sample | α-Helix | β-Sheets | β-Turn | Extended coil | Random |
|---|---|---|---|---|---|
| Soluble GOD init. time | 35.65 | 29.14 | 14.02 | 8.32 | 12.87 |
| After 1 hr at 50° C. | 23.05 | 34.78 | 6.17 | 18.56 | 17.44 |
| After 6 hr at 50° C. | 9.92 | 25.45 | 8.44 | 32.04 | 24.15 |
| GOD-Trehalose init. time | 30.34 | 29.10 | 8.28 | 23.13 | 9.15 |
| After 4 days at 50° C. | 24.63 | 33.32 | 5.78 | 27.17 | 9.10 |
| GOD-Lactitol init. time | 33.82 | 25.88 | 8.82 | 20.41 | 11.07 |
| After 4 days at 50° C. | 27.24 | 27.53 | 8.56 | 19.82 | 16.85 |
| GOD-HPCD init. time | 29.81 | 25.75 | 8.46 | 23.10 | 12.88 |
| After 4 days at 50° C. | 17.15 | 15.75 | 6.12 | 31.67 | 29.31 |
| GOD-MOPEG init. time | 25.45 | 28.23 | 9.62 | 22.52 | 14.18 |
| After 4 days at 50° C. | 15.87 | 30.91 | 8.91 | 28.68 | 15.63 |
| GOD-gelatin init. time | 31.05 | 34.05 | 7.05 | 23.13 | 4.72 |

TABLE 12-continued

Soluble Glucose Oxidase at 50° C.

| Sample | α-Helix | β-Sheets | β-Turn | Extended coil | Random |
|---|---|---|---|---|---|
| After 4 days at 50° C. | 23.49 | 26.2 | 8.58 | 16.24 | 25.49 |
| GOD-Sucrose init. time | 30.12 | 29.68 | 11.03 | 19.75 | 9.42 |
| After 4 days at 50° C. | 24.68 | 23.75 | 9.58 | 31.53 | 10.46 |

Conclusion:

Soluble glucose oxidase lost 75% of its α-helical content within only 6 hours at 50° C.

The sugars lactitol, sucrose and trehalose were the most effective excipients in preventing loss of α-helical content upon storage at an elevated temperature. Glucose oxidase crystals formulated in lactitol, sucrose and trehalose and dried by method 4 showed only an 18.1–19.4 % loss of α-helical structural content after 4 days at 50° C.

Example 32

Drying of Candida Rugosa Lipase Crystals:

Materials:

A—*Candida rugosa* lipase (Example 1)

B—Poly(ethylene glycol), 100% PEG 200, 300, 400, or 600

C—acetone

Procedure:

A 4 ml aliquot of crystal suspension (140 mg) is added to four 15 ml tubes. Next, the suspension is centrifuged at between 1000 to 3000 RPM for between 1 to 5 minutes or until the crystallization buffer is removed. Then, 4 ml of liquid polymer (any PEG between 200 to 600 is suitable) is added to each tube and the contents are mixed until homogeneous. The suspension is centrifuged at between 1000 to 3000 RPM for between 1 to 5 minutes or until the liquid polymer is removed. Next, 4 ml of acetone (isopropanol, butanol and other solvents are also suitable) is added to each tube and mixed well. The crystal/organic solvent suspensions are transferred to 0.8 cm×4 cm BIO-RAD poly-prep chromatography columns (spin columns). The columns are centrifuged at 1000 RPM for 1 to 5 minutes to remove the organic solvent. Finally, nitrogen gas is passed through the column to dry the crystals until a free flowing powder results.

Example 33

Purafect (protease) 4000 L Crystallization:

Materials:

A—crude purafect 4000 L

B—15% $NaSO_4$ solution

Procedure:

One volume of crude purafect enzyme solution is mixed with two volumes of 15% $Na_2SO_4$ solution. The mixture is stirred for 24 hr at room temperature or until the crystallization is completed. The crystals are washed with 15% $Na_2SO_4$ solution to eliminate the soluble enzyme. The crystals are suspended in fresh 15% $Na_2SO_4$ solution to yield a protein concentration of 27 mg/ml.

Example 34

Drying of Purafect Crystals:

Materials:

A—purafect crystals suspension

B—Poly(ethylene glycol), 100% PEG 200, 300, 400, or 600

C—organic solution

Procedure:

A 4 ml aliquot of crystal suspension (140 mg) is added to four 15 ml tubes. Next, the suspension is centrifuged at between 1000 to 3000 RPM for between 1 to 5 minutes or until the crystallization buffer is removed. Then, 4 ml of liquid polymer (any PEG between 200 to 600 is suitable) is added to each tube and the contents are mixed until homogeneous. The suspension is centrifuged at between 1000 to 3000 RPM for between 1 to 5 minutes or until the liquid polymer is removed. Next, 4 ml of acetone (isopropanol, butanol and other solvents are also suitable) is added to each tube and mixed well. The crystal/organic solvent suspensions are transferred to 0.8 cm×4 cm BIO-RAD poly-prep chromatography columns (spin columns). The columns are centrifuged at 1000 RPM for 1 to 5 minutes to remove the organic solvent. Finally, nitrogen gas is passed through the column to dry the crystals until a free flowing powder results.

Example 35

Producing DNA for Crystallization

Plasmids derived from pUC plasmids, such as pSP64, may be used to produce either DNA or mRNA for crystallization. In this example, plasmid pSP64 (available from Promega Biological Research Products) is used to generate DNA for crystallization. The cDNA coding for the protein of interest is inserted into any of a number restriction sites available in the multiple cloning site. The recombinant plasmid is then used to transform *E. coli* bacteria. Next, large amounts of plasmid are obtained by growth of the bacteria in ampicillin containing medium. The techniques for producing the recombinant plasmid, transforming *E. coli* cells and for bacterial growth and plasmid DNA preparation are described in detail in "Molecular Cloning, 2nd Edition" (1989) Sambrook, J., Fritsch, E. F. and T. Maniatis.

Plasmid DNA is subsequently purified from the bacterial cultures by first lysing the cells and then separating the plasmid DNA from the genomic DNA, RNA and other cellular materials using CsCl gradients. These techniques are well known in the art and are discussed in detail in Sambrook et al. The gradient purified DNA is extracted with Tris-EDTA buffer saturated N-butanol and finally ethanol. Next, plasmid DNA is subjected to either linearization of the plasmid, for use in the generation of mRNA for RNA crystallization (Example 36) or excision of the gene of interest for DNA crystallization (Example 37).

Example 36

Producing mRNA for Crystallization

The SP64 plasmid in combination with SP6 RNA Polymerase (available from Promega Biological Research Products) are used for the generation of milligram quantities of 5' capped RNA transcripts. The plasmid prepared in Example 35, prior to excision of the gene, is linearized with a restriction enzyme downstream of the poly A tail. The linear plasmid is purified by 2 phenol/chloroform and 2 chloroform extractions. DNA is next precipitated with NaOAc (0.3M) and 2 volumes of EtOH. Next, the pellet is resuspended at approximately 1 mg/ml in DEPC-treated distilled and deionized water.

Transcription is carried out in a buffer composed of 400 mM Tris HCl (pH 8.0), 80 mM MgCl$_2$, 50 mM DTT and 40 mM spermidine. The subsequent reagents are added in order to one volume of DEPC-treated water at room temperature: 1 volume SP6 RNA polymerase transcription buffer; rATP, rCTP and rUTP to 1 mM concentration; rGTP to 0.5 mM concentration; 7meG(5')ppp(5')G cap analog (New England Biolabs, Beverly, Mass., 01951) to 0.5 mM concentration; the linearized DNA template prepared above to 0.5 mg/ml concentration; RNAs in (Promega, Madison, Wis.) to 2000 U/ml concentration; and SP6 RNA polymerase (Promega, Madison, Wis.) to 3000 U/ml concentration. The transcription mixture is incubated for 1 hour at 37° C.

The DNA template is then digested by adding 2 U RQ1 DNAse (Promega) per microgram of DNA template used. The digestion reaction is carried out for 15 minutes. The transcribed RNA is extracted twice with chloroform/phenol and twice with chloroform. The supernatant solution is precipitated with 0.3M NaOAc in 2 volumes of EtOH and the pellet is resuspended in 100 ml DEPC-treated deionized water per 500 ml transcription product. Finally, the supernatant solution is passed over an RNAse-free Sephadex G50 column (Boehringer Mannheim # 100 411). The resultant mRNA is sufficiently pure to be used crystallization.

Example 37

DNA Crystallization

Materials:

A—Purified plasmid DNA (Example 35)

B—spermine

C—MPD (2-Methyl-2,4-Pentanediol)

D—5mM Ca Acetate buffer pH 7.0

E—Deionized water

Procedure:

The amplified DNA (Example 35) is removed from the plasmid by restriction digestion. The inserted gene is purified from the plasmid vehicle by agarose gel electrophoresis and extraction of the gene of interest from the gel band of the appropriate molecular weight.

Using the hanging drop technique, DNA at 5 mg/ml in 5 mM Ca Acetate/20% MPD/1 mM spermine buffer at pH 7.0 is incubated at room temperature until 90% of the DNA has crystallized. The resulting crystals are washed with crystallization buffer to remove all the soluble material from the crystals. Then, the crystals are resuspended in fresh crystallization buffer to achieve a DNA concentration of 5 mg/ml.

Example 38

RNA Crystallization

Materials:

A—Purified mRNA (Example 36)

B—spermine

C—MPD (2-Methyl-2,4-Pentanediol)

D—5mM Ca Acetate buffer pH 7.0

E—Deionized water

Procedure:

Using the hanging drop technique, RNA (Example 36) at 5 mg/ml in 5 mM Ca Acetate/20% MPD/1 mM spermine buffer at pH 7.0 is incubated at room temperature until 90% of the RNA has crystallized. The resulting crystals are washed with crystallization buffer to remove all the soluble material from the crystals. Then the crystals are resuspended in fresh crystallization buffer to achieve RNA concentration of 5 mg/ml.

Example 39

Induction of an Immune Response to HIV gp120 Using DNA Crystals

DNA, coding for HIV gp160, is prepared according to the methods of Examples 36 and 37. Crystals of HIV gp160 are then used for immunization of mice. Many genetic clones of both primary and laboratory isolates of HIV are available from the Aids Research and Reagent Program, National Institutes of Allergy and Infectious Diseases, Rockville Md. 20852, for designing vaccines which induce broad neutralizing immunity.

The DNA crystals are maintained in the crystallization buffer and 200 μl/mouse is injected into the rear hind leg. The development of an immune response to gp120 is determined by measuring serum antibodies to the corresponding V3 loop peptide in ELISA on a monthly basis.

Example 40

Induction of an Immune Response to HIV gp120 Using mRNA Crystals

RNA coding HIV gp160 is prepared according to the methods of Examples 35, 36 and 38. Crystals of HIV gp160 mRNA are used for the immunization of mice. Various primary and laboratory isolates of HIV are available from the Aids Research and Reagent Program, National Institutes of Allergy and Infectious Diseases, Rockville Md. 20852, for designing vaccines which induce broad neutralizing immunity.

The RNA crystals are maintained in the crystallization buffer and 200 μl/mouse is injected into the rear hind leg. The development of an immune response to gp120 is determined by measuring serum antibodies to the corresponding V3 loop peptide in ELISA on a monthly basis.

Example 41

Oligo DNA Crystallization

Materials:

A—Synthetic Oligo DNA

B—spermine

C—MPD (2-Methyl-2,4-Pentanediol)

D—5mM Ca Acetate buffer pH 7.0

E—Deionized water

Procedure:

Using the hanging drop technique, synthetic oligo DNA at 5 mg/ml in 5 mM Mg Acetate/30% MPD/1 mM spermine buffer at pH 7.0 is incubated at room temperature until 90% of the DNA has crystallized. The resulting crystals are washed with crystallization buffer to remove all the soluble material from the crystals. Then, the crystals are resuspended in fresh crystallization buffer to achieve a DNA concentration of 5 mg/ml.

Example 42

Antisense DNA Administration For Inhibition of Gene Expression

Oligo DNA crystals coding for DNA sequences which are complementary to the sense strand of an mRNA species which is to be suppressed are generated as in Example 41. Next, the crystals or a formulation containing the crystals is administered to the site where gene expression is intended to be inhibited. Subsequently, cells will take up the DNA crystals or dissolved DNA and the oligo DNA and host mRNA will form complementary base pairs and gene expression will be inhibited for a time.

Encapsulated Protein Crystals

Example 43

Large Scale Crystallization of *Pseudomonas cepacia* Lipase

A slurry of 15 kg crude *Pseudomonas cepacia* lipase (PS 30 lipase-Amano) ("LPS") was dissolved in 100 L distilled deionized water and the volume brought to 200 L with additional distilled deionized water. The suspension was mixed in an Air Drive Lightning mixer for 2 hours at room temperature and then filtered through a 0.5 $\mu$m filter to remove celite. The mixture was then ultrafiltered and concentrated to 10 L (121.4 g) using a 3K hollow fiber filter membrane cartridge. Solid calcium acetate was added to a concentration of 20 mM $Ca(CH_3COO)_2$. The pH was adjusted to 5.5 with concentrated acetic acid, as necessary. The mixture was heated to and maintained at a temperature of 30° C. Magnesium sulfate was added to a 0.2 M concentration, followed by glucopon to a 1% concentration. Isopropanol was then added to a final concentration of 23%. The resulting solution was mixed for 30 minutes at 30° C., then cooled from 30° C. to 12° C. over a 2 hour period. Crystallization was then allowed to proceed for 16 hours.

The crystals were allowed to settle and soluble protein was removed using a peristaltic pump with tygon tubing having a 10 ml pipette at its end. Fresh crystallization solution (23% isopropyl alcohol, 0.2 M $MgSO_4$, 1% glucopon, 20 mM $Ca(CH_3COO)_2$, pH 5.5) was added to bring the concentration of protein to 30 mg/ml (O.D. 280 of a 1 mg/ml solution=1.0, measured using a spectrophotometer at wavelength 280). The crystal yield was about 120 grams.

Crosslinked LPS Crystals

Crosslinked *Pseudomonas cepacia* lipase crystals, sold under the name ChiroCLEC-PC™, are available from Altus Biologics, Inc. (Cambridge, Mass.) were used to produce formulations according to Example 48. Alternatively, lipase crystals as prepared above may be crosslinked using any conventional method.

Example 44

Crosslinking of Glucose Oxidase Crystals

We then crosslinked the glucose oxidase crystals prepared in Example 21 as follows. The crosslinking procedure involved glutaraldehyde, or glutaraldehyde pretreated with either Tris buffer (2-amino-2-hydroxymethyl-1,3-propanediol), lysine or diaminooctane.

The crosslinking was performed using 60 mg of protein. Tris pretreated glutaraldehyde (48 mg Tris-base/g glutaraldehyde) was added to concentrations of 0.2 and 0.6 g/g GO crystals suspended in 0.2 M sodium phosphate at pH 7.0. Reactions were allowed to proceed for two hours at room temperature. After two hours, the crystals were filtered and washed over glass fiber paper.

Figure 21:
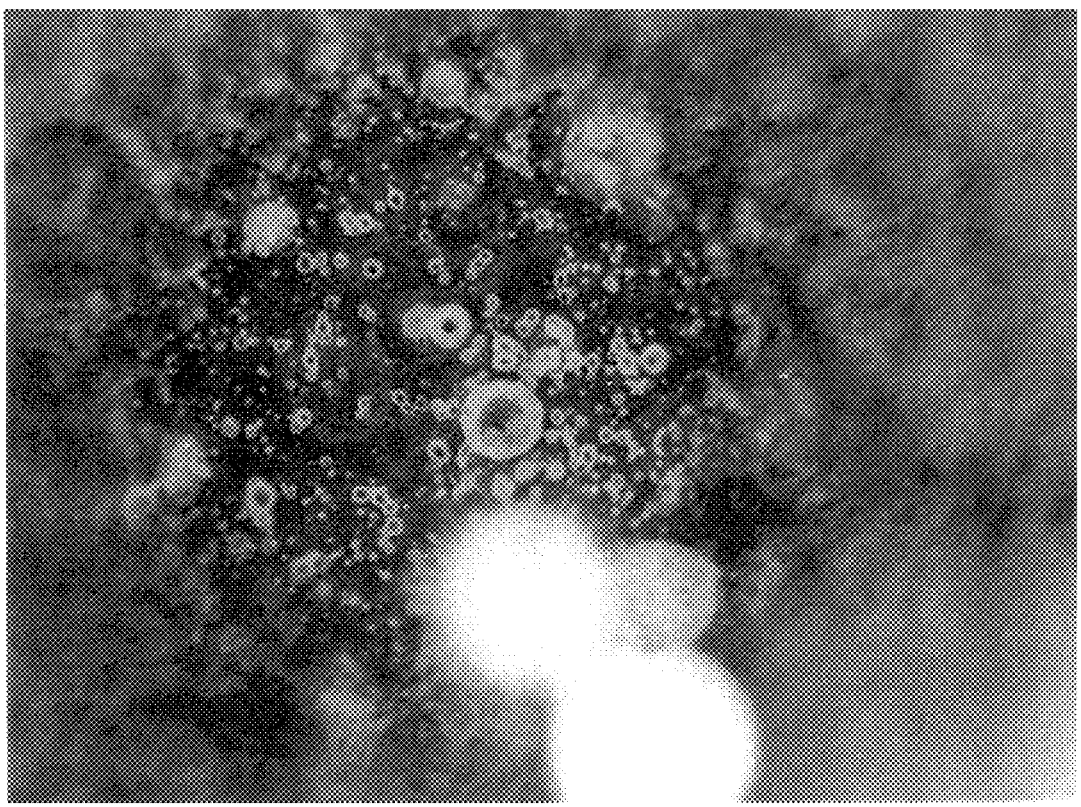
FIG. 21 depicts encapsulated crosslinked enzyme crystals of glucose oxidase from *Aspergillus niger*.

The crosslinked crystals were encapsulated as described in Example 48. No differences were encountered in the encapsulation process between the variously crosslinked crystals. A representative sample is shown in FIG. 21.

Example 45

Crosslinked *Candida Rugosa* Lipase Crystals

Crosslinked *Candida rugosa* lipase crystals, sold under the name ChiroCLEC-CR™, are available from Altus Biologics, Inc. (Cambridge, Mass.) and were used to produce formulations according to Example 48. Alternatively, lipase crystals as prepared above, may be crosslinked using any conventional method.

Example 46

Crosslinking of Human Serum Albumin Crystals

Crosslinking was performed on the human serum albumin crystals prepared in Example 10. The crosslinking reaction was performed at 4° C. in a stirred solution of crystals in the mother liquor containing 50% saturated ammonium sulfate. The crystals were not washed prior to crosslinking with borate-pretreated glutaraldehyde.

Pretreated glutaraldehyde was prepared by adding one volume of 50% glutaraldehyde ("GA") to an equal volume of 300 mM sodium borate at pH 9. The glutaraldehyde solution was then incubated at 60° C. for 1 hour. The solution was cooled to room temperature and the pH was adjusted to 5.5 with concentrated HCl. Next, the solution was rapidly cooled on ice to 4° C.

The pretreated glutaraldehyde (25%) was added to the crystallization solution in a stepwise fashion, using 0.05% increments (total concentration) at 15 minute intervals to a concentration of 2%. Aliquots of the crystallization solution used ranged between 1 ml and 500 ml volume. The crystals were then brought to 5% GA and incubated at 4° C. for 4 hours to allow crosslinking. Finally, albumin crosslinked crystals were collected by low speed centrifugation and washed repeatedly with pH 7.5, 100 mM Tris HCl. Washing was stopped when the crosslinked crystals could be centrifuged at high speed without aggregation.

Example 47

Crosslinking of Penicillin Acylase

Pretreated glutaraldehyde was prepared by the method of Example 46.

The pretreated glutaraldehyde (25%) was added to the crystallization solution in a stepwise fashion, using 0.05% increments (total concentration) at 15 minute intervals to a concentration of 1.5%. Aliquots of the crystallization solution used ranged between 1 ml and 500 ml volume. Finally, crosslinked crystals were collected by low speed centrifugation and washed repeatedly with pH 7.5, 100 mM Tris HCl. Washing was stopped when the crosslinked crystals could be centrifuged at high speed without aggregation.

Example 48

Microencapsulation of Protein Crystals in Polylactic-co-glycolic Acid (PLGA)

A. Glycoproteins, Proteins, Enzymes Hormones, Antibodies and Peptides

Microencapsulation was performed using uncrosslinked crystals of lipase from *Candida rugosa* and *Pseudomonas cepacia*, glucose oxidase from *Aspergillus niger* and Penicillin acylase from *Escherichia coli*. Further, microencapsulation was performed using crosslinked enzyme crystals of lipase from *Candida rugosa*, glucose oxidase from *Aspergillus niger* and Penicillin acylase from *Escherichia coli*. Table 13 shows the approximate average diameters of samples of the microspheres which were produced by this example. In addition, human serum albumin or any other protein crystals or protein crystal formulation produced may be encapsulated by this technique.

TABLE 13

Microspheres Produced

| Microspheres | Crosslinked Crystals Diameter μm | Crosslinked Crystals Diameter μm |
|---|---|---|
| *Candida rugosa* lipase | 90 | 90 |
| Glucose oxidase | 50 | 50 |
| Penicillin acylase | 90 | 70 |
| Lipase from *Pseudomonas cepacia* (slurry) | 60 | |

B. Preparation of Dry Crystals:

Crystals or crystal formulations dried according to Example 6 may each be used to produce the microspheres of this invention. One process for drying protein crystals for use in this invention involves air drying.

Approximately 500 mg each of *Candida rugosa* lipase crystals from Example 1 (uncrosslinked and crosslinked), glucose oxidase from Examples 21 and 44 (uncrosslinked and crosslinked) and Penicillin acylase from Examples 14 and 47 (uncrosslinked and crosslinked) were air dried. First, the mother liquor was removed by centrifugation at 3000 rpm for 5 minutes. Next, the crystals were at 25° C. in the fume hood for two days.

C. Polymer and Solvents

The polymer used to encapsulate the protein crystals was PLGA. PLGA was purchased as 50/50 Poly(DL-lactide-co-glycolide) from Birmingham Polymers, Inc. from Lot No. D97188. This lot had an inherent viscosity of 0.44 dl/g in HFIP@ 30° C.

The methylene chloride was spectroscopic grade and was purchased from Aldrich Chemical Co. Milwaukee, Wis. The poly vinyl alcohol was purchased from Aldrich Chemical Co. Milwaukee, Wis.

D. Encapsulation of Crystals in PLGA:

The crystals were encapsulated in PLGA using a double emulsion method. The general process was as follows, either dry protein crystals or a slurry of protein crystals was first added to a polymer solution in methylene chloride. The crystals were coated with the polymer and became nascent microspheres. Next, the polymer in organic solvent solution was transferred to a much larger volume of an aqueous solution containing a surface active agent. As a result, the organic solvent began to evaporate and the polymer hardened. In this example, two successive aqueous solutions of decreasing concentrations of emulsifier were employed for hardening of the polymer coat to form microspheres. The following procedure was one exemplification of this general process. Those of skill in the art of polymer science will appreciate that many variations of the procedure may be employed and the following example was not meant to limit the invention.

1.0 Use of Dry Protein Crystals

Dry crystals of crosslinked and uncrosslinked *Candida rugosa* lipase produced according to Example 1, crosslinked and uncrosslinked glucose oxidase produced according to Examples 21 and 45, crosslinked and uncrosslinked penicillin acylase produced according to Example 14 and 47, were weighed into 150 mg samples. The weighed protein crystals were then added directly into a 15 ml polypropylene centrifuge tube (Fisher Scientific) containing 2 ml of methylene chloride with PLGA at 0.6 g PLGA/ml solvent. The crystals were added directly to the surface of the solvent. Next, the tube was throughly mixed by vortexing for 2 minutes at room temperature to completely disperse the protein crystals in the solvent with PLGA. The crystals were allowed to become completely coated with polymer. Further vortexing or agitation may be used to keep the nascent microspheres suspended to allow further coating. The polymer may be hardened as described in section 3.0.

2.0 Use of a Protein Crystal Slurry

A crystal slurry of *Pseudomonas cepacia* lipase was produced using approximately 50 mg of crystals per 200 μl of mother liquor. The crystal slurry was rapidly injected into a 15 ml polypropylene centrifuge tube (Fisher Scientific) with 2 ml of a solution of methylene chloride and poly (lactic-co-glycolic acid) at 0.6 g PLGA/ml solvent. The needle was inserted below the surface of the solvent and injected into the solution. In this case, 150 mg of total protein, or 600 μl of aqueous solution, was injected. The injection was made using a plastic syringe Leur-lok (Becton-Dickinson & Company) and through a 22 gauge (Becton-Dickinson & Company) stainless steel needle. Next, the protein crystal-PLGA slurry was mixed thoroughly by vortexing for 2 minutes at room temperature. The crystals were allowed to be completely coated with polymer. Further vortexing or agitation was optionally used to keep the nascent microspheres suspended to allow further coating.

3.0 Hardening the Polymer Coating

A two step process was employed to facilitate the removal of methylene chloride from the liquid polymer coat and allow the polymer to harden onto the protein crystals. The difference between the steps is that the concentration of emulsifier was much higher in the first solution and the volume of the first solution is much smaller than the second.

In the first step, the polymer coated crystal and methylene chloride suspension was added dropwise to a stirred flask of 180 ml of 6% polyvinyl alcohol (hereinafter "PVA") in water with 0.5% methylene chloride at room temperature. This solution was mixed rapidly for 1 minute.

In step two, the first PVA solution containing the nascent microspheres was rapidly poured into 2.4 liters of cold (4° C.) distilled water. This final bath was mixed gently at 4° C. for 1 hr with the surface of the solution under nitrogen. After 1 hr, the microspheres were filtered using 0.22 μm filter and washed with 3 liters of distilled water containing 0.1% Tween 20 to reduce agglomeration.

Example 49

Production of Encapsulated Crystals

Encapsulated microspheres of *Pseudomonas cepacia* lipase are prepared by phase separation techniques. The crystalline LPS prepared in Example 43 is encapsulated in polylactic-co-glycolic acid ("PLGA") using a double emulsion method. A 700 mg aliquot of protein crystals is injected in methylene chloride containing PLGA (0.6 g PLGA/ml solvent; 10 ml). The mixture is homogenized for 30 sec at 3,000 rpm, using a homogenizer with a microfine tip. The resulting suspension is transferred to a stirred tank (900 ml) containing 6% poly (vinyl alcohol) ("PVA") and methylene chloride (4.5 ml). The solution is mixed at 1,000 rpm for 1 min. The microspheres in the PVA solution are precipitated by immersion in distilled water, washed and filtered. The microspheres are then washed with distilled water containing 0.1% Tween, to reduce agglomeration and dried with nitrogen for 2 days at 4° C.

Example 50

A. Protein Content of Microspheres

The total protein content of the microspheres prepared in Example 48 was measured. Triplicate samples of 25 mg of the PLGA/PVA microspheres were incubated in 1 N sodium hydroxide with mixing for 48 hrs. The protein content was then estimated using Bradford's method (M. M. Bradford, Analytical Biochemistry, vol. 72, page 248–254 (1976)) and a commercially available kit from BioRad Laboratories (Hercules, Calif.). The protein containing microspheres were compared to PLGA microspheres without any crystals and is shown in Table 14.

TABLE 14

Protein Content of Microspheres

| Microspheres | Protein (%) Crosslinked Crystals | Protein (%) Uncrosslinked Crystals |
|---|---|---|
| Unloaded PLGA Microspheres | 0 | |
| Candida rugosa lipase | 30 | 20 |
| Glucose oxidase | 35 | 28 |
| Penicillin acylase | 27 | 25 |
| Lipase from Pseudomonas cepacia (slurry) | 39 | |

The activity per milligram or specific activity of selected samples from Table 14 was determined and is shown in Table 15.

TABLE 15

Specific Activity

| Microspheres | Activity/mg Crosslinked Crystals | Activity/mg Uncrosslinked Crystals |
|---|---|---|
| Unloaded PLGA Microspheres | 0 | 0 |
| Candida rugosa lipase | | 413 |
| Penicillin acylase | | 9.63 |
| Lipase from Pseudomonas cepacia (slurry) | 1414 | |

Example 51

Protein Release from Microspheres

The release of protein from the PLGA microspheres prepared in Example 48 was measured by placing 50 mg of protein encapsulated PLGA microspheres in microcentrifuge filtration tubes containing 0.22 $\mu$m filters. Next, 600 $\mu$l of release buffer (phosphate buffered saline with 0.02% Tween 20 at pH 7.4) was added to the microspheres on the retentate side of the filter. The tubes were incubated at 37° C. to allow dissolution. To measure the amount of protein released with time, samples were taken at different time intervals. The tube was centrifuged at 3000 rpm for 1 minute and the filtrate was removed for protein activity and total protein measurements. The microspheres were then resuspended with another 600 $\mu$l of release buffer.

A. Total Protein Released From Microspheres

Table 16 shows that almost 90% of the input protein was recovered in all cases. In addition, the percentage of total Pseudomonas cepacia lipase released from the microencapsulated protein crystals was relatively constant for approximately 5.7 days or until more than 80% of the input protein had been released at a rate of 15.8%/day. This long rapid release was followed by eight days with a only 0.6% release per day.

In contrast, Table 16 further shows that Candida rugosa lipase crystals displayed the opposite profile, displaying first a slow release which was followed by a rapid release phase. In the first three days, about 10% of the protein was released with a shallow slope of 2.4%/day. From day 4 to day 14, another 80% of the protein was released in a linear fashion and a slope of 7.5%/day. The release profiles shown in Table 16 were obtained at 37° C. and at pH 7.4.

These data illustrate that the encapsulated proteins of this invention are suitable for biological delivery of therapeutic proteins. Various rates of delivery can be selected by manipulating the choice of protein crystal, size of the crystals, crosslinking of the crystals, the hydrophobic and hydrophilic characteristics of the encapsulating polymer, the number of encapsulations, dose of microspheres and other easily controllable variables.

TABLE 16

Protein Release From Microspheres

| Time (hr) | % Input Pseudomonas cepacia Lipase Released | % Input Candida rugosa lipase Released |
|---|---|---|
| 0 | 0 | 0 |
| 18 | 28 | 2 |
| 41 | 56 | 5 |
| 89 | 75 | 10 |
| 137 | 82 | 22 |
| 210 | 84 | 34 |
| 234 | 85 | 47 |
| 306 | 86 | 70 |
| 330 | 87 | 86 |

B. Protein Activity Released From Microspheres

The biological activity of the protein released with time was measured using the olive oil assay for lipase microspheres. These results are shown in Table 17.

The biological activity of the released protein, as shown in Table 17, demonstrates that the microspheres protect and release active protein. The cumulative percent activity released, calculated based on the amount of input protein, was closely correlated with the total protein released (compare Table 16 and Table 17). The two different crystal lipases released essentially 100% active protein. Even after 7 days of immersion at 37° C., the protein that was released from the microspheres was fully active.

TABLE 17

Activity of Released Protein

| Time (hr) | % Input Pseudomonas cepacia Lipase Activity Released | % Input Candida Rugosa lipase Activity Released |
|---|---|---|
| 0 | 0 | 0 |
| 18 | 28 | 2 |
| 41 | 56 | 5 |
| 89 | 75 | 10 |
| 137 | 82 | 22 |
| 210 | 84 | 34 |
| 234 | 85 | 47 |
| 306 | 86 | 70 |
| 330 | 87 | 86 |

The activity measurements set forth above were made using the olive oil assay described in Example 8.

Example 52

Microscopic Examination of PLGA Microspheres

In order to visualize whether the crystals were intact after encapsulation, PLGA microspheres prepared according to Example 48 were examined under an Olympus BX60 microscope equipped with DXC-970MD 3CCD Color Video Camera with Camera Adapter (CMA D2) with Image ProPlus software. Samples of dry microspheres were covered with a glass coverslip, mounted and examined under 10× magnification, using an Olympus microscope with an Olympus UPLAN F1 objective lens 10×/0.30 PH1 (phase contrast), the crystals were readily visualized and the crystal size determined. Microsphere and crystal sizes were determined using Image Pro Software from Olympus and 0.5–150 μm sizing beads provided by the manufacturer. The size of the outer PLGA microspheres was determined, as well as for the crystals.

Figure 17:
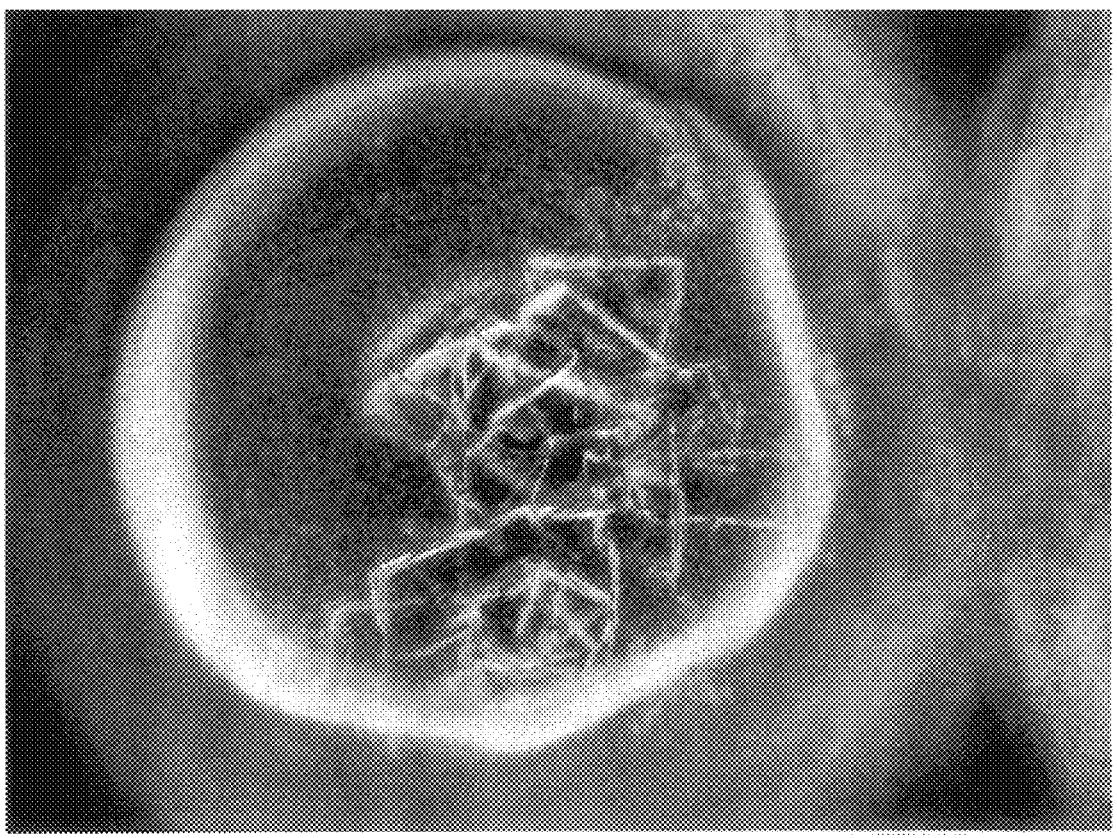
FIG. 17 depicts encapsulated crosslinked enzyme crystals of lipase from *Candida rugosa*.

FIG. 17 depicts crosslinked enzyme crystals of lipase from *Candida rugosa* encapsulated by the method of Example 48. The crystal size was approximately 25 μm and the microspheres were approximately 90 μm. The magnification was 250×.

Figure 18:
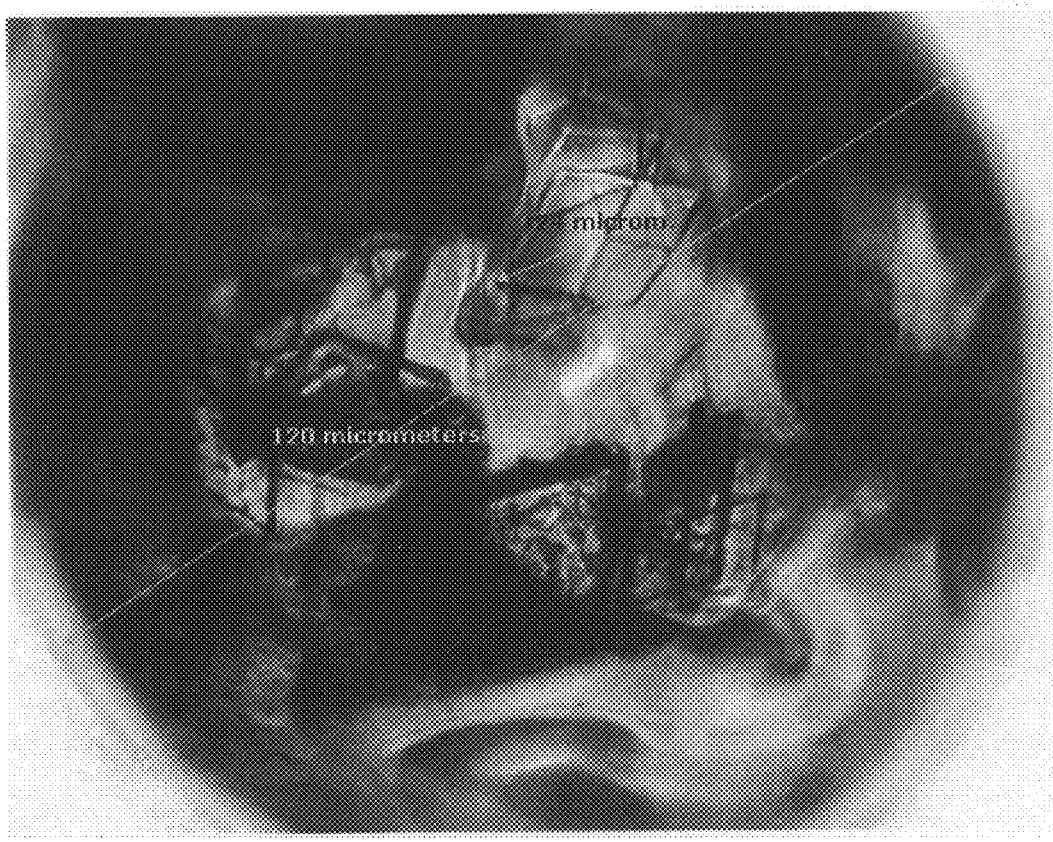
FIG. 18 depicts encapsulated uncrosslinked enzyme crystals of lipase from *Candida rugosa*.

FIG. 18 depicts uncrosslinked enzyme crystals of lipase from *Candida rugosa* encapsulated by the method of Example 48. The crystal size was approximately 25 μm and the microspheres were approximately 120 μm. The magnification was 250×.

Figure 19:
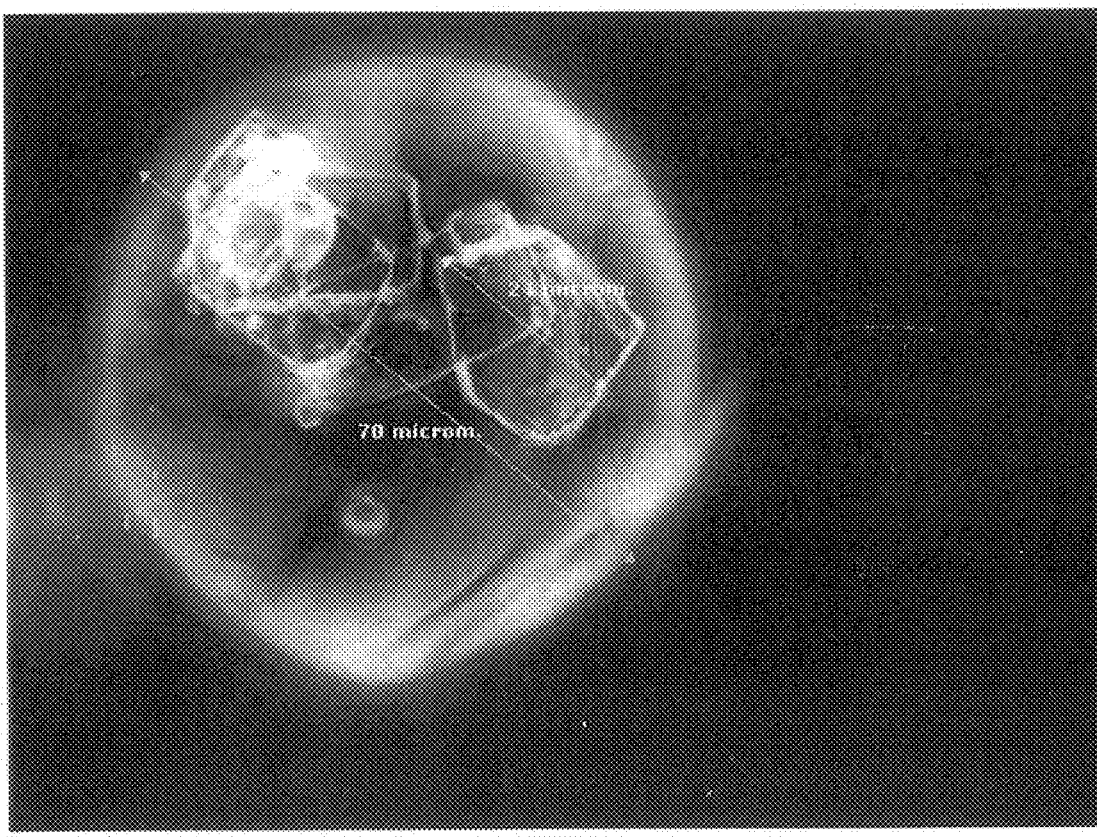
FIG. 19 depicts encapsulated crosslinked enzyme crystals of Penicillin acylase from *Escherichia coli*.

FIG. 19 depicts crosslinked enzyme crystals of Penicillin acylase from *Escherichia coli* encapsulated by the method of Example 48. The crystal size was approximately 25 μm and the microspheres were approximately 70 μm. The magnification was 250×.

Figure 20:
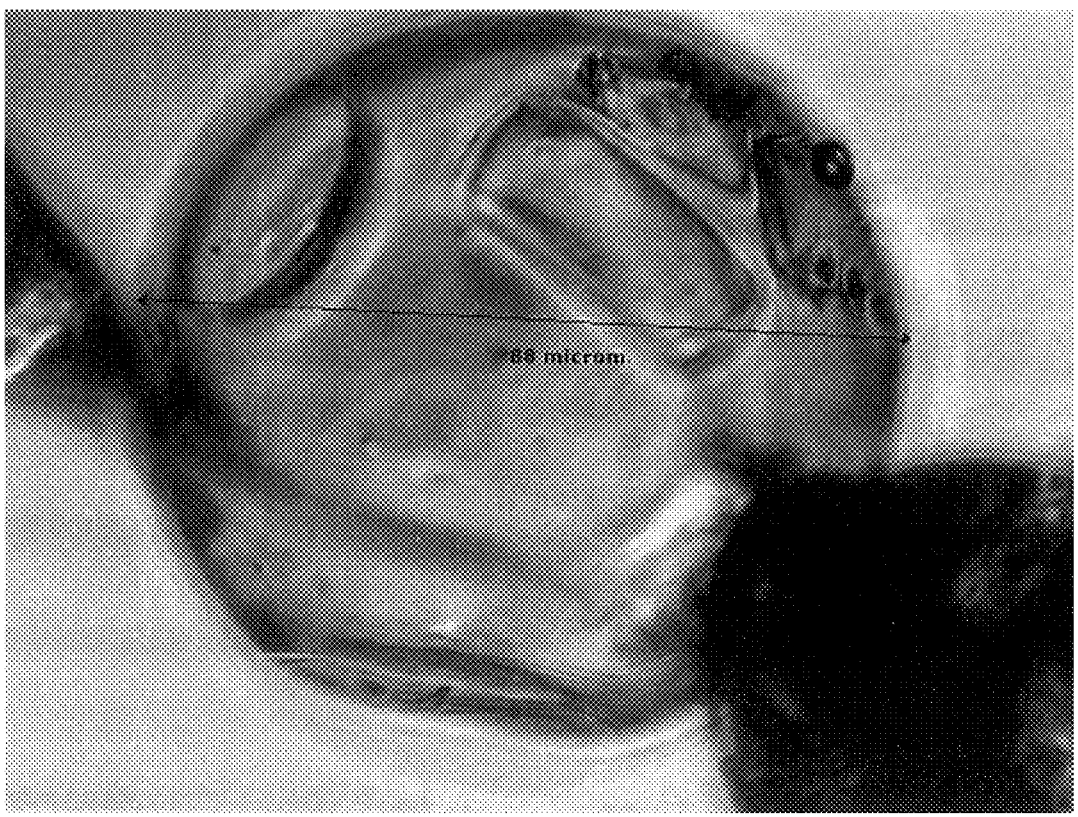
FIG. 20 depicts encapsulated uncrosslinked enzyme crystals of Penicillin acylase from *Escherichia coli*.

FIG. 20 depicts uncrosslinked enzyme crystals of Penicillin acylase from *Escherichia coli* encapsulated by the method of Example 48. The crystal size was approximately 50 μm and the microspheres were approximately 90 μm. The magnification was 250×.

FIG. 21 depicts crosslinked enzyme crystals of glucose oxidase from *Aspergillus niger* encapsulated by the method of Example 48. The crystal size ranged from 0.5 to 1 μm and the microspheres were approximately 50 μm. The magnification was 500×.

Figure 22:
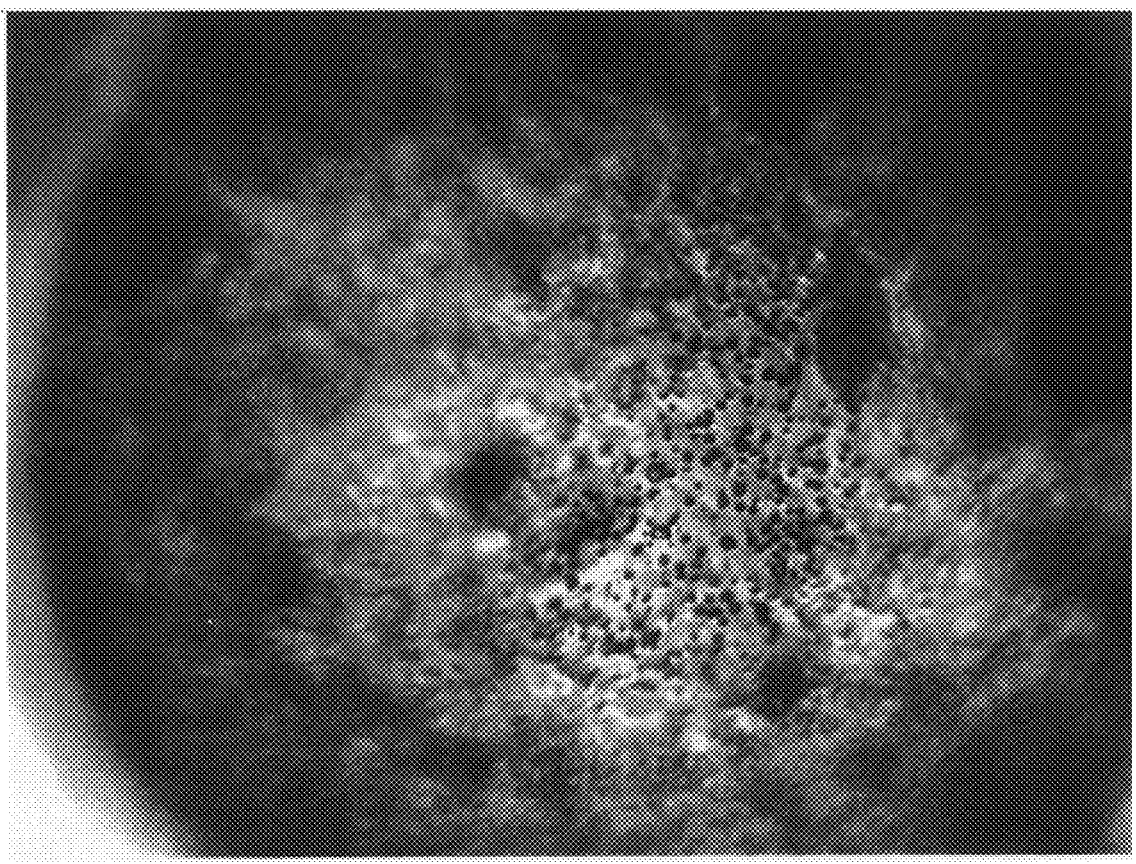
FIG. 22 depicts encapsulated uncrosslinked enzyme crystals of glucose oxidase from *Aspergillus niger*.

FIG. 22 depicts uncrosslinked enzyme crystals of glucose oxidase from *Aspergillus niger* encapsulated by the method of Example 48. The crystal size ranged from 0.5 to 1 μm and the microspheres were approximately 50 μm. The magnification was 500×.

Figure 23:
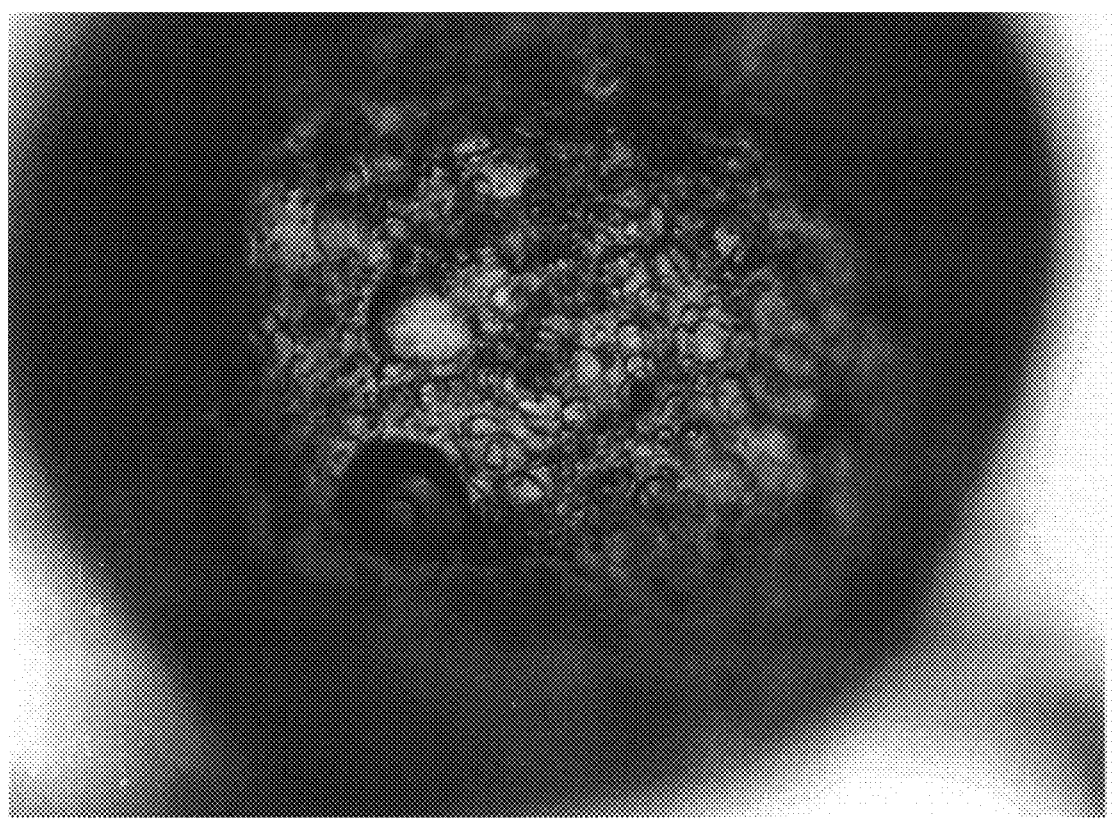
FIG. 23 depicts an encapsulated aqueous slurry of uncrosslinked enzyme crystals of lipase from *Pseudomonas cepacia*.

FIG. 23 depicts uncrosslinked enzyme crystals of lipase from *Pseudomonas cepacia*, encapsulated as a slurry in the mother liquor by the method of Example 48. The crystal size was approximately 2.5 μm and the microspheres were approximately 60 μm. The magnification was 500×.

Figure 24:
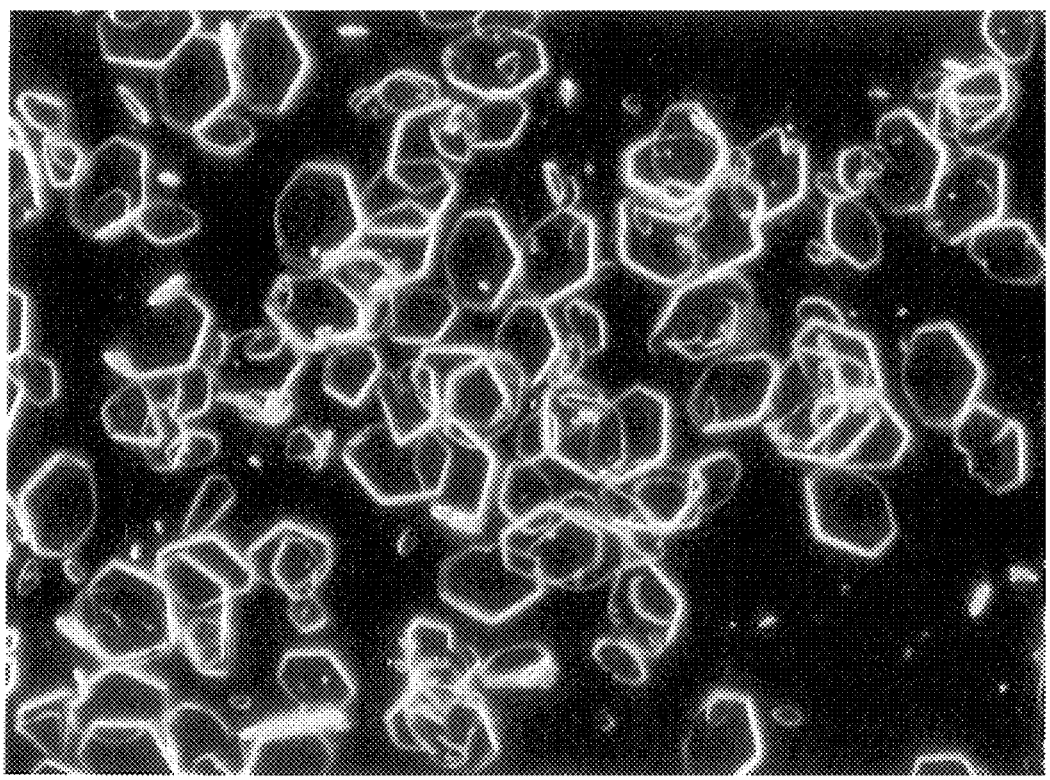
FIG. 24 depicts uncrosslinked enzyme crystals of lipase from *Pseudomonas cepacia*.

FIG. 24 depicts uncrosslinked enzyme crystals of lipase from *Pseudomonas cepacia*. The crystal size was approximately 2.5 μm. The magnification was 1000×.

Example 53

Protein Release

The release of proteins from the PLGA microspheres is measured by placing 50 mg of PLGA microspheres in micro-centrifuge filtration tubes containing 0.22 μm filters. A 600 μl aliquot of release buffer (10 mM HEPES, pH 7.4, 100 mM NaCl, 0.02% Tween, 0.02% azide) is added to suspend the microspheres on the retentate side of the filter. The tubes are sealed with 3 cc vial stoppers and covered by parafilm. The microspheres are then incubated at 37° C. Samples are taken over time by centrifugation (13,000 rpm, 1 min) of the tubes. The filtrate is removed and the microspheres are resuspended with 600 μl of the release buffer. The quality of the released protein is assayed by SEC-HPLC and enzymatic activity.

The shape and size of the protein crystals may be chosen to adjust the rate of dissolution or other properties of the protein crystal formulations of this invention.

Example 54

Encapsulation of Lipase Crystals Using a Biological Polymer

Biological polymers are also useful for encapsulating protein crystals. The present example demonstrates encapsulation of crosslinked and uncrosslinked crystals of *Candida rugosa* lipase crystals. The uncrosslinked and crosslinked crystals were prepared as described in Example 1 and 45. Antibodies and chemicals were purchased from Sigma.

1.0 Preparation of Coated Crystals

A solution of 1.5 ml of bovine serum albumin ("BSA") at 10 mg/ml was prepared, in 5 mM phosphate buffer adjusted to pH 7. Next, 15 ml of a 10 mg/ml suspension of *Candida rugosa* lipase crystals was prepared in 5 mM K/Na phosphate buffer, 1 M NaCl, at pH 7 ("buffer"). The BSA solution was added to the crystal solution and the two solutions were mixed thoroughly. The crystals were incubated in the BSA for 30 min with slow mixing using an orbital shaker. Following the incubation with BSA, the crystals were dryed overnight by vacuum filtration. The dryed crystals were resuspended in buffer without albumin. The crystals were washed with buffer until no protein could be detected in the wash as measured by absorbance at 280 nm or until the $A_{280nm}$ was <0.01. The crystals were recovered by low speed centrifugation.

2.0 Detection of the Albumin Coat

The coated crystals were evaluated by Western blotting to confirm the presence of the albumin layer Following washing, coated protein crystals were incubated in 100 mM NaOH overnight to dissolve the microspheres into the constituent proteins. The samples were neutralized, filtered and analyzed by SDS-PAGE immunoblot according to Sambrook et al. "Molecular Cloning: A Laboratory Manual", Cold Spring Harbor Laboratory Press, Cold Spring Harbor, N.Y. (1989).

The results of SDS-PAGE immunoblot of both albumin coated crosslinked and uncrosslinked crystal microspheres of *Candida rugosa* lipase revealed a single immunoreactive species having the same molecular weight as albumin.

Samples of the albumin coated crosslinked and uncrosslinked crystal microspheres of *Candida rugosa* lipase were incubated with a fluorescene-labeled anti-BSA antibodies which specifically recognize and bind to bovine serum albumin. Next, excess antibody was removed thorough washing with phosphate buffer. Microscopic examination of these fluorescently labeled albumin coated crystal microspheres under a fluorscent microscope revealed specific fluorescene-labeling of the microspheres. Uncoated lipase crystals were used as control and these showed no specific binding of the antibody.

While we have hereinbefore described a number of embodiments of this invention, it is apparent that our basic constructions can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

We claim:

1. A formulation comprising:
   a) a batch-processed protein crystal, wherein said protein is selected from the group consisting of hydrolases, lipases, bacterial proteins and human growth hormone; and
   b) an excipient, wherein said excipierit and said protein crystal are in a ratio between 0.01:99.99 and 30:70 (W/W);
   wherein said formulation has at least a 59 fold greater shelf life when stored at 40° C. and 75% humidity than a nonformulated form of said protein crystal when stored at 40° C. and 75% humidity, as measured by the time required for the specific activity of the protein to decrease by 50% ($T_{1/2}$).

2. A formulation comprising:
   a) a batch-processed protein crystal, wherein said protein is an oxidase enzyme; and
   b) an excipient, wherein said excipient and said protein crystal are in a ratio between 0.01:99.99 and 30:70 (W/W);
   wherein said formulation has at least a 59 fold greater shelf life when stored at 40° C. and 75% humidity than a nonformulated form of said protein crystal when stored at 40° C. and 75% humidity, as measured by the time required for the specific activity of the protein to decrease by 50% ($T_{1/2}$).

3. A formulation comprising:
   a) a batch-processed protein crystal, wherein said protein is human Serum albumin; and
   b) an excipient, wherein said excipient and said protein crystal are in a ratio between 0.01:99.99 and 30:70 (W/W);
   wherein said formulation has at least a 59 fold greater shelf life when stored at 40° C. and 75% humidity than a nonformulated form of said protein crystal when stored at 40° C. and 75% humidity, as measured by the time required for the specific activity of the protein to decrease by 50% ($T_{1/2}$).

4. A formulation comprising:
   a) a batch-processed protein crystal, wherein said protein is selected from the group consisting of hydrolases, lipases, bacterial proteins and human growth hormone; and
   b) an excipient, wherein said excipient and said protein crystal are in a ratio between 0.01:99.9 and 30:70 (W/W);
   wherein said formulation has at least a 60% greater shelf life when stored at 50° C. than a nonformulated form of said protein crystal when stored at 50° C., as measured by the time required for the specific activity of the protein to decrease by 50% ($T_{1/2}$).

5. A formulation comprising:
   a) a batch-processed protein crystal, wherein said protein is an oxidase enzyme; and
   b) an excipient, wherein said excipient and said protein crystal are in a ratio between 0.01:9.99 and 30:70 (W/W);
   wherein said formulation has at least a 60% greater shelf life when stored at 50° C. than a nonformulated form of said protein crystal when stored at 50° C., as measured by the time required for the specific activity of the protein to decrease by 50% ($T_{1/2}$).

6. A formulation comprising:
   a) a batch-processed protein Crystal, wherein said protein is human serum albumin; and
   b) an excipient, wherein said excipient and said protein crystal are in a ratio between 0.01:99.99 and 30:70 (W/W);
   wherein said formulation has at least a 60% greater shelf life when stored at 50° C. than a nonformulated form of said protein crystal when stored at 50° C., as measured by the time required for the specific activity of the protein to decrease by 50% ($T_{1/2}$).

7. A formulation comprising:
   a) a batch-processed protein crystal, wherein said protein is selected from the group consisting of hydrolases, lipases, bacterial proteins and human growth hormone; and
   b) an excipient, wherein said excipient and said protein crystal are in a ratio between 0.01:99.99 and 30:70 (W/W);
   wherein said formulation loses less than 20% α-helical structural content of the protein after storage for 4 days at 50° C., wherein a soluble form of said protein loses more than 50% of its α-helical structural content after storage for 6 hours at 50° C., as measured by fourier transform infrared (FTIR).

8. A formulation comprising:
   a) a batch-processed protein crystal, wherein said protein is an oxidase enzyme; and
   b) an excipient, wherein said excipient and said protein crystal are in a ratio between 0.01:99.99 and 30:70 (W/W);
   wherein said formulation loses less than 20% α-helical structural content of the protein after storage for 4 days at 50° C., wherein a soluble form of said protein loses more than 50% of its α-helical structural content after storage for 6 hours at 50° C., as measured by fourier transform infrared (FTIR).

9. A formulation comprising:
   a) a batch-processed protein crystal, wherein said protein is human serum albumin; and
   b) an excipient, wherein said excipient and said protein crystal are in a ratio between 0.01:99.99 and 30:70 (W/W);
   wherein said formulation loses less than 20% α-helical structural content of the protein after storage for 4 days at 50° C., wherein a soluble form of said protein loses more than 50% of its α-helical structural content after storage for 6 hours at 50° C., as measured by fourier transform infrared (FTIR).

10. The formulation according to any one of claims 1, 2, 3, 4, 5, 6, 7, 8 or 9, wherein said protein is greater than 10,000 Daltons in molecular weight.

11. The formulation according to any one of claims 1, 2, 3, 4, 5, 6, 7, 8 or 9, wherein said excipient is selected from the group consisting of sucrose, trehalose, lactitol, gelatin, hydroxypropyl-β-cyclodextrtn, methoxypolyethylene glycol and polyethylene glycol.

12. A microsphere comprising the formulation according to any one of claims 1, 2, 3, 4, 5, 6, 7, 8 or 9.

13. The formulation according to any one of claims 1, 4 or 7, wherein said ratio of said excipient to said protein crystal is between 0.1:99.9 and 10:90 (W/W).

14. The formulation according to claim 13, wherein said ratio of said excipient to said protein crystal is between 1:99 and 10:90 (W/W).

15. The formulation according to according to any one of claims 1, 4 or 7, wherein said lipase is *Candida rugosa* lipase.

16. The formulation according to according to any one of claims 1, 4 or 7, wherein said hydrolase is penicillin acylase.

17. The formulation according to any one of claims 1, 4 or 7, wherein said lipase is *Pseudomonas cepacia* lipase.

18. The formulation according to according to any one of claims 2, 5 or 8, wherein said oxidase enzyme is glucose oxidase.

19. The formulation according to any one of claims 2, 5 or 8, wherein said ratio of said excipient to said protein crystal is between 0.1:99.9 and 10:90 (W/W).

20. The formulation according to claim 19, wherein said ratio of said excipient to said protein crystal is between 1:99 and 10:90 (W/W).

21. The formulation according to any one of claims 3, 6 or 9, wherein said ratio of said excipient to said protein crystal is between 0.1:99.9 and 10:90 (W/W).

22. The formulation according to claim 21, wherein said ratio of said excipient to said protein crystal is between 1:99 and 10:90 (W/W).

* * * * *

UNITED STATES PATENT AND TRADEMARK OFFICE
CERTIFICATE OF CORRECTION

PATENT NO.   : 6,541,606 B2
DATED        : April 1, 2003
INVENTOR(S)  : Alexey L. Margolin et al.

It is certified that error appears in the above-identified patent and that said Letters Patent is hereby corrected as shown below:

Column 4,
Line 9, change "desribed" to -- described --;

Column 7,
Line 4, change "(ß-hydroxybutryate)" to -- (ß-hydroxybutyrate) --;
Line 13, change "Biodearadable" to -- Biodegradable --;

Column 8,
Line 20, change "Britian" to -- Britain --;

Column 9,
Line 24, insert -- . -- at end of line after "thereof";
Line 32, change "an" to -- a --;

Column 10,
Line 5, change "acorbyl" to -- ascorbyl --;
Line 9, change "sufur" to -- sulfur --;
Line 46, change "soritan" at end of line to -- sorbitan --;

Column 12,
Line 9, change "seame" to -- sesame --;
Line 55, change "potssium" to -- potassium --;

Column 17,
Line 26, change "CE20" to -- CD20 --;

Column 18,
Line 56, delete "which" at beginning of line;

UNITED STATES PATENT AND TRADEMARK OFFICE
CERTIFICATE OF CORRECTION

PATENT NO. : 6,541,606 B2
DATED : April 1, 2003
INVENTOR(S) : Alexey L. Margolin et al.

It is certified that error appears in the above-identified patent and that said Letters Patent is hereby corrected as shown below:

Column 26
Line 17, change "Cu Tb Rh)" to -- Cu TI Rh) --;
Lines 20-21, delete "DESYL groups in linker" from column labelled "Trigger" and add -- DESYL groups in linker -- under column labelled "Examples";
Line 66, change "[2-pyridyldlthio]" to -- [2-pyridyldithio] --;

Column 27,
Line 44, insert -- . -- at end of line after "crosslinking";

Column 28,
Line 50, change "biocompatinie" to -- biocompatible --;

Column 29,
Line 48, change "of, first occurence," to -- or --;
Line 65, change "a-helical" to -- α-helical --;

Column 30,
Line 11, change "matix" to -- matrix --;
Line 33, change "a-helical" to -- α-helical --;

Column 34,
Line 66, delete " were";

Column 35,
Line 46, change "$^{cmt-1}$)." to -- $cm^{-1}$). --;

Column 36,
Line 37, change "a-helical" to -- α-helical --;

Column 38,
Line 56, change "diafilration" to -- diafiltration --;
Line 63, delete "top of to";

UNITED STATES PATENT AND TRADEMARK OFFICE
CERTIFICATE OF CORRECTION

PATENT NO. : 6,541,606 B2
DATED : April 1, 2003
INVENTOR(S) : Alexey L. Margolin et al.

It is certified that error appears in the above-identified patent and that said Letters Patent is hereby corrected as shown below:

Column 39,
Line 20, change "Of" to -- of --;

Column 40,
Line 43, insert -- . -- at end of line after "substrate";

Column 41,
Line 45-46, change "stucture" to -- structure --;

Column 46,
Line 30, delete "after", second occurrence;
Line 34-35, change "stucture" to -- structure --;
Line 40, after "which" insert -- was --;

Column 48,
Line 36, after "number" insert -- of --;

Column 49,
Line 27, after "used" insert -- for --;

Column 54,
Line 4, change "thrughly" to -- thoroughly --;

Column 56,
Line 2, delete "a";

Column 58,
Line 56, delete "a";
Line 58, change "thorough" to -- through --;

UNITED STATES PATENT AND TRADEMARK OFFICE
CERTIFICATE OF CORRECTION

PATENT NO.    : 6,541,606 B2
DATED         : April 1, 2003
INVENTOR(S)   : Alexey L. Margolin et al.

It is certified that error appears in the above-identified patent and that said Letters Patent is hereby corrected as shown below:

Column 59,
Line 13, change "excipierit" to -- excipient --;
Line 37 change "Serum" to -- serum --;
Line 66, change "0.01:9.99" to -- 0.01:99.99 --;

Column 60,
Line 7, change upper case "Crystal" to -- crystal --;
Line 64, change "hydroxypropyl -β- cyclodextrtn" to -- hydroxypropyl-β-cyclodextrin --;

Column 61,
Line 10, delete second occurrence of "according to".
Line 14, delete second occurrence of "according to";

Signed and Sealed this

Twentieth Day of July, 2004

JON W. DUDAS
*Acting Director of the United States Patent and Trademark Office*